US008563746B2

(12) United States Patent
Dang et al.

(10) Patent No.: US 8,563,746 B2
(45) Date of Patent: Oct. 22, 2013

(54) CYCLIC BENZIMIDAZOLE DERIVATIVES USEFUL AS ANTI-DIABETIC AGENTS

(75) Inventors: Qun Dang, San Diego, CA (US); De Michael Chung, Rowland Heights, CA (US); Tony S. Gibson, San Diego, CA (US); Hongjian Jiang, San Diego, CA (US); Daniel K. Cashion, San Diego, CA (US); Jianming Bao, Princeton, NJ (US); Ping Lan, Dayton, NJ (US); Huagang Lu, Plainsboro, NJ (US); Gergely M. Makara, Budapest (HU); F. Anthony Romero, Westfield, NJ (US); Iyassu Sebhat, Jersey City, NJ (US); Dariusz Wodka, Monmouth Junction, NJ (US)

(73) Assignees: Merck Sharp & Dohme Corp, Rahway, NJ (US); Metabasis Therapeutics, Inc., La Jolla, CA (US)

( * ) Notice: Subject to any disclaimer, the term of this patent is extended or adjusted under 35 U.S.C. 154(b) by 0 days.

(21) Appl. No.: 13/125,329

(22) PCT Filed: Oct. 19, 2009

(86) PCT No.: PCT/US2009/061132
§ 371 (c)(1),
(2), (4) Date: Apr. 21, 2011

(87) PCT Pub. No.: WO2010/051176
PCT Pub. Date: May 6, 2010

(65) Prior Publication Data
US 2011/0195964 A1    Aug. 11, 2011

Related U.S. Application Data

(60) Provisional application No. 61/197,606, filed on Oct. 29, 2008.

(51) Int. Cl.
*A61K 31/4184* (2006.01)
*A61K 31/5377* (2006.01)
*A61K 31/497* (2006.01)
*C07D 235/26* (2006.01)
*C07D 235/28* (2006.01)
*C07D 401/10* (2006.01)
*C07D 401/06* (2006.01)
*C07D 409/04* (2006.01)
*C07D 403/10* (2006.01)
*C07D 413/10* (2006.01)
*C07D 413/14* (2006.01)
*C07D 417/04* (2006.01)

(52) U.S. Cl.
USPC ............ 548/306.4; 548/307.1; 548/181; 546/273.7; 546/199; 544/124; 544/139; 544/405; 514/231.5; 514/252.1; 514/235.5; 514/338; 514/322; 514/387; 514/394; 514/365

(58) Field of Classification Search
USPC ............................. 548/306.4, 307.1
See application file for complete search history.

(56) References Cited

U.S. PATENT DOCUMENTS

| | | | | |
|---|---|---|---|---|
| 3,558,775 A | * | 1/1971 | Fournier | 514/166 |
| 4,814,329 A | * | 3/1989 | Harsanyi et al. | 514/211.15 |
| 5,596,025 A | | 1/1997 | Oxman et al. | |
| 5,612,360 A | * | 3/1997 | Boyd et al. | 514/381 |
| 6,040,327 A | * | 3/2000 | De Nanteuil et al. | 514/394 |
| 6,051,570 A | * | 4/2000 | Lohray et al. | 514/217.04 |
| 6,969,712 B2 | | 11/2005 | Okamoto et al. | |
| 7,176,320 B2 | | 2/2007 | Tsuchiya et al. | |
| 7,268,145 B2 | | 9/2007 | Matsumoto et al. | |
| 2003/0083315 A1 | | 5/2003 | Tsuchiya et al. | |
| 2004/0122042 A1 | | 6/2004 | Urata et al. | |
| 2005/0113283 A1 | | 5/2005 | Solow-Cordero et al. | |
| 2005/0255415 A1 | | 11/2005 | Louwet et al. | |
| 2005/0272765 A1 | | 12/2005 | Feng et al. | |
| 2006/0160872 A1 | | 7/2006 | Norman et al. | |
| 2007/0032466 A1 | | 2/2007 | Urata et al. | |
| 2007/0161680 A1 | | 7/2007 | Alkawa et al. | |

FOREIGN PATENT DOCUMENTS

| | | |
|---|---|---|
| DE | 32 09 486 A1 | 9/1982 |
| DE | 33 16 095 A1 | 11/1983 |
| EP | 0 120 403 B1 | 10/1984 |
| EP | 0 126 030 A2 | 11/1984 |
| EP | 0 126 030 A3 | 11/1984 |
| EP | 0 128 862 B1 | 12/1984 |
| EP | 0 129 506 B1 | 12/1984 |
| EP | 0 161 219 B1 | 11/1985 |
| EP | 0 161 220 B1 | 11/1985 |
| EP | 0 161 222 B1 | 11/1985 |
| EP | 0 194572 B1 | 9/1986 |

(Continued)

OTHER PUBLICATIONS

Fujisawa Pharmaceutical Co., Ltd., CA 112:178987, 1990 (abstract of JP 01/258670 A).*
An English translation of JP 01-258670 A, Oct. 1989.*
Ram et al., Journal of Heterocyclic Chemistry, (1985), 22(5), pp. 1269-1274.*
Chemical Abstracts Registry No. 892674-27-0, indexed in the Registry file on STN Jul. 14, 2006.*
Charton, J. et al., "Synthesis and biological evaluation of benzimidazole derivatives as potent AMP-activated protein kinase activators", Bioorganic & Medicinal Chemistry, 2006, p. 4490-4518, vol. 14.

(Continued)

*Primary Examiner* — Laura L. Stockton
(74) *Attorney, Agent, or Firm* — Baerbel R. Brown; Catherine D. Fitch

(57) ABSTRACT

Novel compounds of the structural formula (I) are activators of AMP-protein kinase and are useful in the treatment, prevention and suppression of diseases mediated by the AMPK-activated protein kinase. The compounds of the present invention are useful in the treatment of Type 2 diabetes, hyperglycemia, metabolic syndrome, obesity, hypercholesterolemia, and hypertension.

13 Claims, No Drawings

(56) References Cited

FOREIGN PATENT DOCUMENTS

| | | |
|---|---|---|
| EP | 0 398 600 B1 | 11/1990 |
| EP | 0 637 585 A1 | 2/1995 |
| EP | 0 655 439 A2 | 5/1995 |
| EP | 0 655 439 A3 | 5/1995 |
| EP | 0 560 407 B1 | 5/1996 |
| JP | 01/258670 A * | 10/1989 |
| JP | 5-52065 A | 3/1993 |
| JP | 5-239036 A | 9/1993 |
| JP | 6-19066 A | 1/1994 |
| JP | 6-298731 A | 10/1994 |
| JP | 9-227854 A | 9/1997 |
| JP | 2002-141067 A | 5/2002 |
| JP | 2004-67629 A | 3/2004 |
| JP | 2007-39406 A | 2/2007 |
| WO | 92/20642 A1 | 11/1992 |
| WO | 93/07124 A1 | 4/1993 |
| WO | 94/08962 A1 | 4/1994 |
| WO | 95/29897 A1 | 11/1995 |
| WO | 98/08818 A1 | 3/1998 |
| WO | 98/39342 A1 | 9/1998 |
| WO | 98/39344 A1 | 9/1998 |
| WO | 98/56761 A2 | 12/1998 |
| WO | 98/56761 A3 | 12/1998 |
| WO | 99/43672 A1 | 9/1999 |
| WO | 00/03997 A1 | 1/2000 |
| WO | 00/14095 A1 | 3/2000 |
| WO | 00/52015 A2 | 9/2000 |
| WO | 00/52015 A3 | 9/2000 |
| WO | 01/25238 A2 | 4/2001 |
| WO | 01/25238 A3 | 4/2001 |
| WO | 01/53272 A1 | 7/2001 |
| WO | 01/53291 A1 | 7/2001 |
| WO | 02/40019 A1 | 5/2002 |
| WO | 02/092575 A1 | 11/2002 |
| WO | 03/024937 A1 | 3/2003 |
| WO | 03/062392 A2 | 7/2003 |
| WO | 03/062392 A3 | 7/2003 |
| WO | 2004/035740 A2 | 4/2004 |
| WO | 2004/035740 A3 | 4/2004 |
| WO | 2004/043913 A2 | 5/2004 |
| WO | 2004/043913 A3 | 5/2004 |
| WO | 2004/085425 A1 | 10/2004 |
| WO | 2004/106348 A1 | 12/2004 |
| WO | 2005/002520 A2 | 1/2005 |
| WO | 2005/002520 A3 | 1/2005 |
| WO | 2005/009389 A3 | 2/2005 |
| WO | 2005/009389 A2 | 5/2005 |
| WO | 2005/042518 A2 | 5/2005 |
| WO | 2005/042518 A3 | 5/2005 |
| WO | 2005/044793 A2 | 5/2005 |
| WO | 2005/044793 A3 | 5/2005 |
| WO | 2005/121132 A1 | 12/2005 |
| WO | 2006/047415 A2 | 5/2006 |
| WO | 2006/047415 A3 | 5/2006 |
| WO | 2006/048159 A1 | 5/2006 |
| WO | 2006/053342 A2 | 5/2006 |
| WO | 2006/053342 A3 | 5/2006 |
| WO | 2006/094209 A2 | 9/2006 |
| WO | 2006/094209 A3 | 9/2006 |
| WO | 2006/0099379 A2 | 9/2006 |
| WO | 2006/099379 A3 | 9/2006 |
| WO | 2006/116412 A2 | 11/2006 |
| WO | 2006/116412 A3 | 11/2006 |
| WO | 2007/007463 A1 | 1/2007 |
| WO | 2007/007464 A1 | 1/2007 |
| WO | 2007/063993 A1 | 7/2007 |
| WO | 2007/084390 A2 | 7/2007 |
| WO | 2007/091106 A2 | 8/2007 |
| WO | 2007/095124 A2 | 8/2007 |
| WO | 2007/095124 A3 | 8/2007 |
| WO | 2008/008551 A2 | 1/2008 |
| WO | 2008/008551 A3 | 1/2008 |
| WO | 2008/009348 A1 | 1/2008 |
| WO | 2008/062773 A1 | 5/2008 |
| WO | 2009/019504 A1 | 2/2009 |
| WO | 2009/100130 A1 | 8/2009 |
| WO | 2010/036613 A1 | 4/2010 |
| WO | 2010/047982 A1 | 4/2010 |
| WO | 2010/051176 A1 | 5/2010 |
| WO | 2010/051206 A1 | 5/2010 |

OTHER PUBLICATIONS

Pagano, M. A. et al., "Optimiaation of Protein Kinase CK2 Inhibitors Derived from 4,5,6,7-Tetrabromobenzimidazole", J. Med. Chem, 2004, p. 6239-6247, vol. 47.

Rudolph, M. J. et al., "Crystal structure of the protein kinase domain of yeast AMP-activated protein kinase Snf1", Biochemical and Biophysical Research Communications, 2005, p. 1224-1228, vol. 337.

Bindal, V. et al., "Heterocyclic Systems Containing Bridgehead Nitrogen Atom: Part LIV—Synthesis of Thiazolo[3,2-a]benzimidazol-3-(2H)-ones", Indian Journal of Chemistry, 1986, p. 807-811, vol. 25B.

Bortolato. A. et al., "In Silico Binding Free Energy Predictability by Using the Linear Interaction Energy (LIE) Method: Bromobenzimidazole CK2 Inhibitors as a Case Study", J. Chem. Inf. Model, 2007, p. 575-582, vol. 47.

Czarnocka-Janowicz, A. et al., "Derivatives of 4(7)-Methyl-and 5,6-Dimethyl-Benzimidazolyl-2-Mercaptoacetic Acids", Pol. J. Pharmacol. Pharm, 1977, p. 69-73, vol. 29.

Krasovakii, A. N. et al., "Studies in the Imidazole Series LVII. synthesis of 6,7-Dimethylbenzimidazo[2,1-b]-Thiazolid-3-One and its derivatives with respect to the methylene group", p. 767, Chemistry of Heterocyclic Compounds, 1971.

Labanauskas, L. et al., "Synthesis of 6,7-dialkoxy-2-arylmethylidene-2,3-dihydrobenzo[4,5]-imidazo[2,1-b][1,3]thiazol-3-ones exhibiting anti-inflammatory activity", Pharmazie, 2000, vol. 6, pp. 429-431.

Lan, P. et al., "An efficient method to access 2-substituted benzimidazoles under solvent-free conditions", Tetrahedron Letters, 2008, p. 1910-1914, vol. 49.

Narayan, S. et al., "heterocyclic Systems Containing Bridgehead Nitrogen Atom: Part LII—Synthesis of 6,7-Dimethoxy & 5,8-Dimethoxy Thiazolo[3,2-a]benzimidazol-3(2H)-ones, Thiazolo[3,2-a]benzimidazoles & 2,3-Dihydrothiazolo[3,2-a]benzimidazoles", Indian Journal of Chemistry, 1986, p. 267-270, vol. 25B.

Pagano, M. A. et al., "Optimization of Protein Kinase CK2 Inhibitors Derived from 4,5,6,7-Tetrabromobenzimidazole", J. Med. Chem, 2004, p. 6239-6247, vol. 47.

Rebstock, T. L. et al., "Efect of Chemical structure on the growth inhibition of Plants with some acid analogs of 2-Mercaptobenzimidazole", Plant Physiology, p. 19-22., vol. 32, No. 1, Jan. 1957.

Tunnicliff, G. et al., "The Action of Structural Analogues of—Aminobutyric Acid on Binding Sites in Mouse Brain", Drug Development Research, 1984, p. 51-59, vol. 4.

Chaudhary, H. S. et al., "Heterocyclic Systems Containing Bridgehead Nitrogen Atom: Part VII—Syntheses of 6-Methyl-, 8-Methyl-, 6,7-Dimethyl-, & 5,8-Dimethyl-Thiazolo[3,2-a]benzimidazol-3(2H)-ones & 2H-7,8-Dimethyl-[I,3] thiazino[3,2-a]benzimidazol-4(3H)-one", Indian Journal of Chemistry, 1970, p. 10-15, vol. 8.

* cited by examiner

CYCLIC BENZIMIDAZOLE DERIVATIVES USEFUL AS ANTI-DIABETIC AGENTS

CROSS-REFERENCE TO RELATED APPLICATIONS

This application is a U.S. National Phase application under 35 U.S.C. §371 of PCT Application No. PCT/US2009/061132, filed Oct. 19, 2009, which claims priority from and the benefit of U.S. Provisional Application No. 61/197,606, filed Oct. 29, 2008.

BACKGROUND OF THE INVENTION

Diabetes is characterized by elevated levels of plasma glucose (hyperglycemia) in the fasting state or after administration of glucose during an oral glucose tolerance test. In type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced by islet cells in the pancreas. Patients having Type 2 diabetes have a resistance to the effects of insulin in stimulating glucose and lipid metabolism in the main insulin-sensitive tissues, including muscle, liver and adipose tissues. These patients often have normal levels of insulin, and may have hyperinsulinemia (elevated plasma insulin levels), as they compensate for the reduced effectiveness of insulin by secreting increased amounts of insulin (Polonsky, *Int. J. Obey. Relat. Metab. Disord.* 24 *Suppl* 2:S29-31, 2000). Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver. Eventually, a patient may be become diabetic due to the inability to properly compensate for insulin resistance. In humans, the beta cells within the pancreatic islets initially compensate for insulin resistance by increasing insulin output. The onset of Type 2 diabetes due to insufficient increases (or actual declines) in beta cell mass is apparently due to increased beta cell apoptosis relative to non-diabetic insulin resistant individuals (Butler et al., *Diabetes* 52:102-110, 2003).

Persistent or uncontrolled hyperglycemia is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, effective therapeutic control of glucose homeostasis, lipid metabolism, obesity, and hypertension are critically important in the clinical management and treatment of diabetes mellitus.

Patients who have insulin resistance often exhibit several symptoms that together are referred to as syndrome X or metabolic syndrome. Patients with metabolic syndrome have an increased risk of developing atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide and liraglitide); and (5) inhibitors of incretin hormone degradation (DPP-4 inhibitors, such as sitagliptin).

Many of the current treatments for diabetes have unwanted side effects. Phenformin and metformin can induce lactic acidosis, nausea/vomiting, and diarrhea. Metformin has a lower risk of side effects than phenformin and is widely prescribed for the treatment of Type 2 diabetes. The currently marketed PPAR gamma agonists are modestly effective in reducing plasma glucose and hemoglobin A1C, and do not greatly improve lipid metabolism or the lipid profile. Sulfonylureas and related insulin secretagogues can cause insulin secretion even if the glucose level is low, resulting in hypoglycemia, which can be fatal in severe cases. The administration of insulin secretagogues must therefore be carefully controlled. There remains a need for treatments for diabetes that work by novel mechanisms of action and that exhibit fewer side effects.

AMP-activated protein kinase (AMPK) has been identified as a regulator of carbohydrate and fatty acid metabolism that helps maintain energy balance in response to environmental and nutritional stress. There is evidence that activation of AMPK results in a number of beneficial effects on lipid and glucose metabolism by reducing glucogenesis and de novo lipogenesis (fatty acid and cholesterol synthesis), and by increasing fatty acid oxidation and skeletal muscle glucose uptake. Inhibition of ACC, by phosphorylation by AMPK, leads to a decrease in fatty acid synthesis and to an increase in fatty acid oxidation, while inhibition of HMG-CoA reductase, by phosphorylation by AMPK, leads to a decrease in cholesterol synthesis (Carling, D. et. al., FEBS Letters 223: 217 (1987)).

In the liver, AMPK activation results in a decrease in fatty acid and cholesterol synthesis, inhibiting hepatic glucose production and increasing fatty acid oxidation. It has been shown that AMP-activated protein kinase regulates triacylglycerol synthesis and fatty acid oxidation in liver and muscle via glycerol-3-phosphate acyltransferase (Muoio, D. M. et. al., Biochem. J. 338:783 (1999)). Another substrate of AMPK, hepatocyte nuclear factor-4α, has been shown to be involved in type-1 maturity onset diabetes (Leclerc, I. et. al., Diabetes 50:1515 (2001)). Additional processes believed to be regulated through AMPK activation include the stimulation of glucose transport in skeletal muscle and the regulation of key genes in fatty acid and glucose metabolism in the liver (Hardie, D. G. and Hawley, S. A., Bioessays 23: 1112 (2001), Kemp, B. E. et al., Biochem. Soc. Transactions 31:162 (2003), Musi, N. and Goodyear, L. J. Current Drug Targets-Immune, Endocrine and Metabolic Disorders 2:119 (2002); Lochhead, P. A. et. al., Diabetes 49:896 (2000); and Zhou, G. et. al., J. of Clin. Invest. 108: 1167 (2001).

In vivo studies have demonstrated the following beneficial effects of both acute and chronic administration of AICAR, an AMPK activator, in rodent models of obesity and type 2 diabetes: 1) an improvement in glucose homeostasis in insulin-resistant diabetic (ob/ob) mice; 2) a decrease in blood glucose concentrations in ob/ob and db/db mice and a blood glucose reduction of 35% following 8 weeks of administration; and 3) a reduction in metabolic disturbances and a reduction of blood pressure in rats displaying characteristics of insulin resistance syndrome (Bergeron, R. et. al., Diabetes 50:1076 (2001); Song, S. M. et. al., Diabetologia 45:56 (2002); Halseth, A. E. et al., Biochem. and Biophys. Res. Comm. 294:798 (2002); and Buhl, E. S. et al., Diabetes 51: 2199 (2002)). A further study of 7 week AICAR administration in obese Zucker (fa/fa) rats lead to a reduction in plasma triglycerides and free fatty acids; an increase in HDL cholesterol; and a normalization of glucose metabolism as assessed by an oral glucose tolerance test (Minokoshi, Y. et. al., Nature 415: 339 (2002)). Expression of dominant negative AMPK in skeletal muscle of transgenic mice has demonstrated that the AICAR effect on stimulation of glucose transport is dependent on AMPK activation (Mu, J. et. al., Molecular Cell 7: 1085 (2001)).

Recent data also suggest that AMPK activation is involved in the glucose and lipid-lowering effects of the anti-diabetic drug metformin. It has been shown that the diabetes drug metformin can activate AMPK in vivo at high concentrations (Zhou, G. et. al., J. of Clin. Invest. 108: 1167 (2001); Musi, N. et. al. Diabetes 51: 2074 (2002)).

Based on these studies, it is expected that the in vivo activation of AMPK in the liver may result in the reduction of hepatic glucose output, an improvement in overall glucose homeostasis, a decrease in fatty acid and cholesterol synthesis, and an increase in fatty acid oxidation. Stimulation of AMPK in skeletal muscle is expected to result in an increase in glucose uptake and fatty acid oxidation with resulting improvement of glucose homeostasis, and an improvement in insulin action. Finally, the resulting increase in energy expenditure should lead to a decrease in body weight. The lowering of blood pressure has also been reported to be a consequence of AMPK activation.

Increased fatty acid synthesis is a characteristic of many tumor cells, therefore decreasing the synthesis of fatty acids via AMPK activation may also be useful as a cancer therapy. Activation of AMPK may also be useful to treat ischemic events in the brain (Blazquez, C. et. al., J. Neurochem. 73: 1674 (1999)); to prevent damage from reactive oxygen species (Zhou, M. et. al., Am. J. Physiol. Endocrinol. Metab. 279: E622 (2000)); and to improve local circulatory systems (Chen, Z.-P., et. al. AMP-activated protein kinase phosphorylation of endothelial NO synthase. FEBS Letters 443: 285 (1999)).

Compounds that activate AMPK are expected to be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent AMPK activators that have pharmacokinetic and pharmacodynamic properties suitable for use as human pharmaceuticals.

Benzimidazole compounds are disclosed in WO 93/07124; WO 95/29897; WO 98/39342; WO 98/39343; WO 00/14095; WO 00/03997; WO 01/53272; WO 01/53291; WO 02/092575; WO 02/40019; WO 03/018061; WO 05/002520; WO 05/018672; WO 06/094209; U.S. Pat. No. 6,312,662; U.S. Pat. No. 6,489,476; US 2005/0148643; DE 3 316 095; JP 6 298 731; EP 0 126 030; EP 0 128 862; EP 0 129 506; and EP 0 120 403. AMPK activators are disclosed in WO 08/006,432; WO 05/051298; WO 05/020892; US 2007/015665; US 2007/032529; US 2006/287356; and US 2005/038068.

SUMMARY OF THE INVENTION

The present invention is concerned with novel benzimidazole derivatives of structural Formula I:

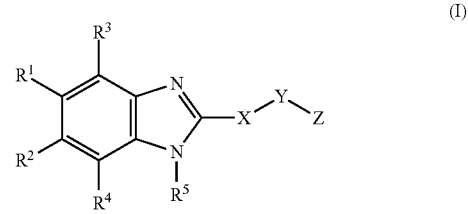

and pharmaceutically acceptable salts thereof. The compounds of structural formula I, and embodiments thereof, are activators of AMP-activated protein kinase (AMPK) and are useful in the treatment, prevention and suppression of diseases, disorders and conditions mediated by activation of AMP-activated protein kinase, such as Type 2 diabetes mellitus, insulin resistance, hyperglycemia, dyslipidemia, lipid disorders, obesity, hypertension, metabolic syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions responsive to activation of AMP-activated protein kinase in a subject in need thereof by administering the compounds and pharmaceutical compositions of the present invention. The present invention also relates to the use of compounds of the present invention for manufacture of a medicament useful in treating diseases, disorders and conditions responsive to the activation of AMP-activated protein kinase. The present invention is also concerned with treatment of these diseases, disorders and conditions by administering the compounds of the present invention in combination with a therapeutically effective amount of another agent known to be useful to treat the disease, disorder and condition. The invention is further concerned with processes for preparing the compounds of this invention.

DETAILED DESCRIPTION OF THE INVENTION

The present invention is concerned with novel compounds of structural Formula I:

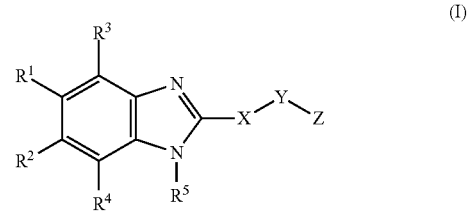

or a pharmaceutically acceptable salt thereof, wherein:
X is absent or selected from:
(1) —S—,
(2) —O—,
(3) —NH—, (4) —C(O)—,
(5) —NHC(O)—,
(6) —C(O)NH—,
(7) —NHSO$_2$—,
(8) —SO$_2$NH—, and
(9) —CO$_2$—,
wherein NH is unsubstituted or substituted with 1 substituent selected from: —C$_{1-6}$alkyl, —CO$_2$H, —CO$_2$C$_{1-6}$alkyl, —COC$_{1-6}$alkyl, phenyl and —CH$_2$phenyl;
Y is selected from:
(1) —CH$_2$—,
(2) —CH$_2$—CH$_2$—,
(3) —CH$_2$—CH$_2$—CH$_2$—,
(4) —CHF—, and
(5) —CF$_2$—,
wherein each CH$_2$ and CHF is unsubstituted or substituted with 1 or 2 substituents selected from R$^b$;
Z is selected from:
(1) —CN,
(2) —(CH$_2$)$_n$CO$_2$H,
(3) —(CH$_2$)$_n$CO$_2$R$^i$,
(4) —(CH$_2$)$_n$OH,
(5) —(CH$_2$)$_n$C(O)NHR$^g$,
(6) —(CH$_2$)$_n$NHC(O)C$_{1-6}$alkyl,
(7) —(CH$_2$)$_n$NHSO$_2$R$^i$,
(8) —(CH$_2$)$_n$SO$_2$NHR$^g$,
(9) —(CH$_2$)$_n$SO$_2$NHC(O)R$^i$,
(10) —(CH$_2$)$_n$SO$_2$NHCO$_2$R$^i$,
(11) —(CH$_2$)$_n$SO$_2$NHCON(R$^g$)$_2$,
(12) —(CH$_2$)$_n$C(O)NHSO$_2$R$^i$,
(13) —(CH$_2$)$_n$NHC(O)N(R$^g$)$_2$,
(14) —(CH$_2$)$_n$C$_{3-10}$cycloalkyl-CO$_2$R$^e$,
(15) heteroaryl,
(16) —C$_{2-10}$cycloheteroalkenyl, and
(17) —C$_{2-10}$cycloheteroalkyl,
wherein each CH$_2$ is unsubstituted or substituted with 1 or 2 substituents selected from C$_{1-6}$alkyl, —OH and —NH$_2$, wherein each NH is unsubstituted or substituted with 1 substituent selected from R$^c$, and wherein each alkyl, cycloalkyl, cycloheteroalkyl, cycloheteroalkenyl, aryl and heteroaryl is unsubstituted or substituted with 1, 2, 3 or 4 substituents selected from R$^c$;
each R$^1$ and R$^2$ is independently selected from:
(1) hydrogen,
(2) halogen,
(3) —CN,
(4) —CF$_3$,
(5) —C$_{1-6}$alkyl,
(6) —C$_{2-6}$alkenyl,
(7) —C$_{2-6}$alkynyl,
(8) —(CH$_2$)$_p$C$_{3-10}$cycloalkyl,
(9) —(CH$_2$)$_p$C$_{3-7}$cycloalkyl-aryl,
(10) —(CH$_2$)$_p$C$_{3-7}$cycloalkyl-heteroaryl,
(11) —(CH$_2$)$_p$C$_{4-10}$cycloalkenyl,
(12) —(CH$_2$)$_p$C$_{4-7}$cycloalkenyl-aryl,
(13) —(CH$_2$)$_p$C$_{4-7}$cycloalkenyl-heteroaryl,
(14) aryl,
(15) biphenyl,
(16) —(CH$_2$)$_p$heteroaryl,
(17) —C$_{2-6}$alkenyl-alkyl,
(18) —C$_{2-6}$alkenyl-aryl,
(19) —C$_{2-6}$alkenyl-heteroaryl,
(20) —C$_{2-6}$alkenyl-C$_{3-7}$cycloalkyl,
(21) —C$_{2-6}$alkenyl-C$_{3-7}$cycloalkenyl,
(22) —C$_{2-6}$alkenyl-C$_{2-7}$cycloheteroalkyl,
(23) —C$_{2-6}$alkenyl-C$_{2-7}$cycloheteroalkenyl,
(24) —C$_{2-6}$alkynyl-(CH$_2$)$_{1-3}$—O-aryl,
(25) —C$_{2-6}$alkynyl-alkyl,
(26) —C$_{2-6}$alkynyl-aryl,
(27) —C$_{2-6}$alkynyl-heteroaryl,
(28) —C$_{2-6}$alkynyl-C$_{3-7}$cycloalkyl,
(29) —C$_{2-6}$alkynyl-C$_{3-7}$cycloalkenyl,
(30) —C$_{2-6}$alkynyl-C$_{2-7}$cycloheteroalkyl,
(31) —C$_{2-6}$alkynyl-C$_{2-7}$cycloheteroalkenyl, and
(32) —(CH$_2$)$_p$C(O)phenyl,
wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each alkyl, alkenyl and alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and
wherein each cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$, provided that at least one of and only one of R$^1$ and R$^2$ is selected from the group consisting of: hydrogen, halogen, —CN, —CF$_3$, —C$_{1-6}$alkyl, —C$_{2-6}$alkenyl and —C$_{2-6}$alkynyl, and provided that if R$^1$ or R$^2$ is hydrogen, then at least one of R$^3$ and R$^4$ is not hydrogen;
R$^3$ and R$^4$ are each independently selected from:
(1) hydrogen,
(2) halogen,
(3) —C$_{1-6}$alkyl,
(4) —C$_{2-6}$alkenyl,
(5) —C$_{2-6}$alkynyl,
(6) —C$_{3-10}$cycloalkyl,
(7) —C$_{3-10}$cycloalkenyl,
(8) aryl,
(9) heteroaryl,
(10) —CN,
(11) —CF$_3$,
(12) —OH,
(13) —OC$_{1-6}$alkyl,
(14) —NH$_2$,
(15) —NHC$_{1-6}$alkyl,
(16) —N(C$_{1-6}$alkyl)$_2$,
(17) —SC$_{1-6}$alkyl,
(18) —SOC$_{1-6}$alkyl,
(19) —SO$_2$C$_{1-6}$alkyl,
(20) —NHSO$_2$C$_{1-6}$alkyl,
(21) —NHC(O)C$_{1-6}$alkyl,
(22) —SO$_2$NHC$_{1-6}$alkyl, and
(23) —C(O)NHC$_{1-6}$alkyl;
R$^5$ is selected from:
(1) hydrogen,
(2) —C$_{1-6}$alkyl,
(3) —CH$_2$CO$_2$H, and
(4) —CH$_2$CO$_2$C$_{1-6}$alkyl;
each R$^a$ is independently selected from the group consisting of:
(1) halogen,
(2) oxo,
(3) —(CH$_2$)$_m$OH,
(4) —(CH$_2$)$_m$N(R$^j$)$_2$,
(5) —(CH$_2$)$_m$NO$_2$,
(6) —(CH$_2$)$_m$CN,
(7) —C$_{1-6}$alkyl,
(8) —(CH$_2$)$_m$CF$_3$,
(9) —(CH$_2$)$_m$OCF$_3$,
(10) —OCH$_2$OC$_{1-6}$alkyl,
(11) —O-aryl,
(12) —OCH$_2$-aryl,
(13) —(CH$_2$)$_m$C(=N—OH)N(R$^j$)$_2$,

(14) —(CH$_2$)$_m$OC$_{1-6}$alkyl,
(15) —(CH$_2$)$_m$—O-aryl,
(16) —(CH$_2$)$_m$SC$_{1-6}$alkyl,
(17) —(CH$_2$)$_m$S(O)C$_{1-6}$alkyl,
(18) —(CH$_2$)$_m$S(O)$_2$C$_{1-6}$alkyl,
(19) —(CH$_2$)$_m$NHS(O)$_2$C$_{1-6}$alkyl,
(20) —(CH$_2$)$_m$C(O)R$^f$,
(21) —(CH$_2$)$_m$C(O)N(R$^j$)$_2$,
(22) —(CH$_2$)$_m$N(R$^j$)C(O)R$^f$,
(23) —(CH$_2$)$_m$N(R$^j$)C(O)N(R$^j$)$_2$,
(24) —(CH$_2$)$_m$CO$_2$H,
(25) —(CH$_2$)$_m$OC(O)H,
(26) —(CH$_2$)$_m$CO$_2$R$^f$,
(27) —(CH$_2$)$_m$OC(O)R$^f$,
(28) —(CH$_2$)$_m$C$_{3-7}$cycloalkyl,
(29) —(CH$_2$)$_m$C$_{3-7}$cycloalkenyl,
(30) —(CH$_2$)$_m$C$_{2-6}$cycloheteroalkyl,
(31) —(CH$_2$)$_m$C$_{2-6}$cycloheteroalkenyl,
(32) —(CH$_2$)$_m$aryl, and
(33) —(CH$_2$)$_m$heteroaryl,
wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl;
each R$^b$ is independently selected from:
(1) hydrogen,
(2) —C$_{1-6}$alkyl,
(3) halogen,
(4) —OH,
(5) —NO$_2$,
(6) —NH$_2$,
(7) —NH(C$_{1-6}$alkyl),
(8) —N(C$_{1-6}$alkyl)$_2$,
(9) —OC$_{1-6}$alkyl,
(10) —(CH$_2$)$_q$CO$_2$H,
(11) —(CH$_2$)$_q$CO$_2$C$_{1-6}$alkyl,
(12) —CF$_3$,
(13) —CN,
(14) —SO$_2$C$_{1-6}$alkyl, and
(15) —(CH$_2$)$_q$CON(R$^e$)$_2$,
wherein each CH$_2$ is unsubstituted or substituted with 1 or 2 halogens, and wherein each alkyl, cycloalkyl, cycloalkenyl, cycloheteroalkyl, aryl and heteroaryl is unsubstituted or substituted with 1, 2 or 3 halogens;
each R$^c$ is independently selected from:
(1) halogen,
(2) oxo,
(3) —(CH$_2$)$_r$OH,
(4) —(CH$_2$)$_r$N(R$^e$)$_2$,
(5) —(CH$_2$)$_r$CN,
(6) —C$_{1-6}$alkyl,
(7) —CF$_3$,
(8) —C$_{1-6}$alkyl-OH,
(9) —OCH$_2$OC$_{1-6}$alkyl,
(10) —(CH$_2$)$_r$OC$_{1-6}$alkyl,
(11) —OCH$_2$aryl,
(12) —(CH$_2$)$_r$SC$_{1-6}$alkyl,
(13) —(CH$_2$)$_r$C(O)R$^f$,
(14) —(CH$_2$)$_r$C(O)N(R$^e$)$_2$,
(15) —(CH$_2$)$_r$CO$_2$H,
(16) —(CH$_2$)$_r$CO$_2$R$^f$,
(17) —(CH$_2$)$_r$C$_{3-7}$cycloalkyl,
(18) —(CH$_2$)$_r$C$_{2-6}$cycloheteroalkyl,
(19) —(CH$_2$)$_r$aryl, and
(20) —(CH$_2$)$_r$heteroaryl,
wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl;
each R$^e$, R$^g$ and R$^h$ is independently selected from:
(1) hydrogen, and
(2) C$_{1-6}$alkyl,
wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;
each R$^j$ is independently selected from:
(1) hydrogen,
(2) C$_{1-6}$alkyl,
(3) C$_{3-6}$cycloalkyl,
(4) —C(O)R$^i$, and
(5) —SO$_2$R$^i$,
wherein alkyl and cycloalkyl are unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;
each R$^f$ and R$^i$ is independently selected from:
(1) C$_{1-6}$alkyl,
(2) C$_{4-7}$cycloalkyl,
(3) C$_{4-7}$cycloalkenyl,
(4) C$_{3-7}$cycloheteroalkyl,
(5) C$_{3-7}$cycloheteroalkenyl,
(6) aryl, and
(7) heteroaryl,
wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl;
n is 0, 1, 2, 3 or 4;
m is 0, 1, 2, 3 or 4;
p is 0, 1, 2, or 3;
q is 0, 1, 2, 3 or 4; and
r is 0, 1 or t.

In one embodiment X is absent or selected from: —S—, —O—, —NH—, —C(O)—, —NHC(O)—, —C(O)NH—, —NHSO$_2$—, —SO$_2$NH—, and —CO$_2$—, wherein NH is unsubstituted or substituted with 1 substituent selected from: —C$_{1-6}$alkyl, —CO$_2$H, —CO$_2$C$_{1-6}$alkyl, —COC$_{1-6}$alkyl, phenyl and —CH$_2$phenyl. In a class of this embodiment, X is absent or selected from: —S—, —O—, —NH—, —C(O)—, —NHC(O)—, —C(O)NH—, —NHSO$_2$—, —SO$_2$NH—, and —CO$_2$—. In another embodiment, X is absent. In another embodiment, X is absent or selected from: —S—, —O—, and —C(O)NH—, wherein NH is unsubstituted or substituted with 1 substituent selected from: —C$_{1-6}$alkyl, —CO$_2$H, —CO$_2$C$_{1-6}$alkyl, —COC$_{1-6}$alkyl, phenyl and —CH$_2$phenyl. In a class of this embodiment, X is selected from: —S—, —O—, and —C(O)NH—, wherein NH is unsubstituted or substituted with 1 substituent selected from: —$C_{1-6}$alkyl, —$CO_2H$, —$CO_2C_{1-6}$alkyl, —$COC_{1-6}$alkyl, phenyl and —$CH_2$phenyl. In another class of this embodiment, X is selected from: —S—, —O—, and —C(O)NH—. In another embodiment, X is absent or selected from: —S— and —O—. In another embodiment, X is absent or —S—. In another embodiment, X is —S—. In another embodiment, X is absent or —O—. In another embodiment, X is —O—. In another embodiment of the present invention, Y is selected from: —$CH_2$—, —$CH_2$—$CH_2$—, —$CH_2$—$CH_2$—$CH_2$—, —CHF—, and —$CF_2$—, wherein each —$CH_2$ and —CHF is unsubstituted or substituted with 1 or 2 substituents selected from $R^b$. In a class of this embodiment, Y is selected from: —$CH_2$—, —$CH_2$—$CH_2$—, —$CH_2$—$CH_2$—$CH_2$—, —CHF—, and —$CF_2$—.

In another embodiment of the present invention, Y is selected from: —$CH_2$—, —$CH_2$—$CH_2$—, and —$CH_2$—$CH_2$—$CH_2$—, wherein each —$CH_2$ is unsubstituted or substituted with 1 or 2 substituents selected from $R^b$. In a class of this embodiment, Y is selected from: —$CH_2$—, —$CH_2$—$CH_2$—, and —$CH_2$—$CH_2$—$CH_2$—. In another class of this embodiment, Y is —$CH_2$—. In another class of this embodiment, Y is —$CH_2$—$CH_2$—. In another class of this embodiment, Y is —$CH_2$—$CH_2$—$CH_2$—. In another embodiment of the present invention, Y is selected from: —$CH_2$— and —$CH_2$—$CH_2$—, wherein each —$CH_2$ is unsubstituted or substituted with 1 or 2 substituents selected from $R^b$. In a class of this embodiment, Y is selected from: —$CH_2$—, wherein $CH_2$ is unsubstituted or substituted with 1 or 2 substituents selected from $R^b$. In another class of this embodiment, Y is —$CH_2$—$CH_2$—, wherein each —$CH_2$ is unsubstituted or substituted from $R^b$. In another class of this embodiment, Y is selected from: —$CH_2$— and —$CH_2$—$CH_2$—. In another class of this embodiment, Y is —$CH_2$—. In another class of this embodiment, Y is —$CH_2$—$CH_2$—. In another embodiment of the present invention, Y is —$CH_2$—, wherein each —$CH_2$ is unsubstituted or substituted with 1 or 2 substituents selected from $R^b$. In a class of this embodiment, Y is —$CH_2$—. In another embodiment of the present invention, Y is —$CH_2$—$CH_2$—, wherein each —$CH_2$ is unsubstituted or substituted with 1 or 2 substituents selected from $R^b$. In a class of this embodiment, Y is —$CH_2$—$CH_2$—.

In another embodiment of the present invention, Z is selected from: —CN, —$(CH_2)_nCO_2H$, —$(CH_2)_nCO_2R^i$, —$(CH_2)_nOH$, —$(CH_2)_nC(O)NHR^g$, —$(CH_2)_nNHC(O)C_{1-6}$alkyl, —$(CH_2)_nNHSO_2R^i$, —$(CH_2)_nSO_2NHR^g$, —$(CH_2)_nSO_2NHC(O)R^i$, —$(CH_2)_nSO_2NHCO_2R^i$, —$(CH_2)_nSO_2NHCON(R^g)_2$, —$(CH_2)_nC(O)NHSO_2R^i$, —$(CH_2)_nNHC(O)N(R^g)_2$, —$(CH_2)_nC_{3-10}$cycloalkyl-$CO_2R^e$, heteroaryl, —$C_{2-10}$cycloheteroalkenyl, and —$C_{2-10}$cycloheteroalkyl, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl, cycloalkyl, cycloheteroalkyl, cycloheteroalkenyl, aryl and heteroaryl is unsubstituted or substituted with 1, 2, 3 or 4 substituents selected from $R^c$. In another embodiment of the present invention, Z is selected from: —CN, —$(CH_2)_nCO_2H$, —$CO_2R^i$, —OH, —$(CH_2)_nC(O)NHR^g$, —$NHC(O)C_{1-6}$alkyl, —$NHSO_2R^i$, —$SO_2NHR^g$, —$SO_2NHC(O)R^i$, —$SO_2NHCO_2R^i$, —$SO_2NHCON(R^g)_2$, —$C(O)NHSO_2R^i$, $NHC(O)N(R^g)_2$, —$C_{3-10}$cycloalkyl-$CO_2R^e$, heteroaryl, —$C_{2-10}$cycloheteroalkenyl, and —$C_{2-10}$cycloheteroalkyl, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl, cycloalkyl, cycloheteroalkyl, cycloheteroalkenyl, aryl and heteroaryl is unsubstituted or substituted with 1, 2 or 3 substituents selected from $R^c$. In another embodiment of the present invention, Z is selected from: —CN, —$(CH_2)_nCO_2H$, —$(CH_2)_nCO_2R^i$, —$(CH_2)_nOH$, —$(CH_2)_nC(O)NHR^g$, heteroaryl, and —$C_{2-10}$cycloheteroalkenyl, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl, cycloalkyl, cycloheteroalkyl, cycloheteroalkenyl, aryl and heteroaryl is unsubstituted or substituted with 1, 2, 3 or 4 substituents selected from $R^c$. In a class of this embodiment, Z is selected from: —CN, —$CO_2H$, —$CO_2R^i$, —OH, —$C(O)NHR^g$, heteroaryl, and —$C_{2-10}$cycloheteroalkenyl, wherein each NH is unsubstituted or substituted with 1 substituent selected from $R^c$, and wherein each alkyl, cycloalkyl, cycloheteroalkyl, cycloheteroalkenyl, aryl and heteroaryl is unsubstituted or substituted with 1, 2 or 3 substituents selected from $R^c$. In another class of this embodiment, Z is selected from: —CN, —$CO_2H$, —$CO_2R^i$, —OH, —$C(O)NH_2$, heteroaryl, and —$C_{2-10}$cycloheteroalkenyl, wherein each NH is unsubstituted or substituted with 1 substituent selected from $R^c$, and wherein each cycloheteroalkenyl and heteroaryl is unsubstituted or substituted with 1, 2 or 3 substituents selected from $R^c$. In another class of this embodiment, Z is selected from: —CN, —$CO_2H$, —$CO_2R^i$, —OH, —$C(O)NH_2$, tetrazole, and dihydrooxadiazole, wherein each cycloheteroalkenyl and heteroaryl is unsubstituted or substituted with 1, 2 or 3 substituents selected from $R^c$.

In another embodiment of the present invention, Z is selected from: —$(CH_2)_nCO_2H$, —$(CH_2)_nCO_2R^i$, —$(CH_2)_nC(O)NHR^g$, heteroaryl, and —$C_{2-10}$cycloheteroalkenyl, wherein each $CH_2$ is unsubstituted or substituted with 1 or 2 substituents selected from $C_{1-6}$alkyl, —OH and —$NH_2$, wherein each NH is unsubstituted or substituted with 1 substituent selected from $R^c$, and wherein each alkyl, cycloalkyl, cycloheteroalkyl, cycloheteroalkenyl, aryl and heteroaryl is unsubstituted or substituted with 1, 2, 3 or 4 substituents selected from $R^c$. In a class of this embodiment, Z is selected from: —$CO_2H$, —$CO_2R^i$, —$C(O)NHR^g$, heteroaryl, and —$C_{2-10}$cycloheteroalkenyl, wherein each NH is unsubstituted or substituted with 1 substituent selected from $R^c$, and wherein each cycloheteroalkenyl and heteroaryl is unsubstituted or substituted with 1, 2 or 3 substituents selected from $R^c$. In a class of this embodiment, Z is selected from: —$CO_2H$, —$C(O)NHR^g$, heteroaryl, and —$C_{2-10}$cycloheteroalkenyl, wherein each NH is unsubstituted or substituted with 1 substituent selected from $R^c$, and wherein each cycloheteroalkenyl and heteroaryl is unsubstituted or substituted with 1, 2 or 3 substituents selected from $R^c$. In another class of this embodiment, Z is selected from: —$CO_2H$, —$C(O)NH_2$, heteroaryl, and —$C_{2-10}$cycloheteroalkenyl, wherein each cycloheteroalkenyl and heteroaryl is unsubstituted or substituted with 1, 2 or 3 substituents selected from $R^c$. In a subclass of this class, Z is selected from: —$CO_2H$, —$C(O)NH_2$, tetrazole, and dihydrooxadiazole, wherein each cycloheteroalkenyl and heteroaryl is unsubstituted or substituted with 1, 2, or 3 substituents selected from $R^c$. In another class of this embodiment, Z is selected from: heteroaryl, and —$C_{2-10}$cycloheteroalkenyl, wherein each cycloheteroalkenyl and heteroaryl is unsubstituted or substituted with 1, 2 or 3 substituents selected from $R^c$. In a subclass of this class, Z is selected from: tetrazole, and dihydrooxadiazole, wherein each cycloheteroalkenyl and heteroaryl is unsubstituted or substituted with 1, 2, or 3 substituents selected from $R^c$.

In another embodiment of the present invention, Z is selected from: —$(CH_2)_nCO_2H$, and —$(CH_2)_nC(O)NHR^g$, wherein each $CH_2$ is unsubstituted or substituted with 1 or 2 substituents selected from $C_{1-6}$alkyl, —OH and —$NH_2$, and wherein each NH is unsubstituted or substituted with 1 substituent selected from $R^c$. In a class of this embodiment, Z is selected from: —$CO_2H$, and —$C(O)NH_2$. In another embodiment of the present invention, Z is —$(CH_2)_nCO_2H$, wherein each $CH_2$ is unsubstituted or substituted with 1 or 2 substituents selected from $C_{1-6}$alkyl, —OH and —$NH_2$. In another embodiment of the present invention, Z is —$(CH_2)_nCO_2H$. In another embodiment of the present invention, Z is —$CO_2H$.

In another embodiment of the present invention, each $R^1$ and $R^2$ is independently selected from: hydrogen, halogen, —CN, —$CF_3$, —$C_{1-6}$alkyl, —$C_{2-6}$alkenyl, —$C_{2-6}$alkynyl, —$C_{3-10}$cycloalkyl, —$C_{3-7}$cycloalkyl-aryl, —$C_{3-7}$cycloalkyl-heteroaryl, —$C_{4-10}$cycloalkenyl, —$C_{4-7}$cycloalkenyl-aryl, —$C_{4-7}$cycloalkenyl-heteroaryl, aryl, biphenyl, -heteroaryl, —$C_{2-6}$alkenyl-alkyl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$alkynyl-$(CH_2)_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$ cycloheteroalkyl, —$C_{2-6}$alkynyl-$C_{2-7}$cycloheteroalkenyl, and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each alkyl, alkenyl and alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl, and provided that if $R^1$ or $R^2$ is hydrogen, then at least one of $R^3$ and $R^4$ is not hydrogen. In a class of this embodiment, $R^1$ is selected from: —$C_{3-10}$cycloalkyl, —$C_{3-7}$cycloalkyl-aryl, —$C_{3-7}$cycloalkyl-heteroaryl, —$C_{4-10}$cycloalkenyl, —$C_{4-7}$cycloalkenyl-aryl, —$C_{4-7}$cycloalkenyl-heteroaryl, aryl, biphenyl, -heteroaryl, —$C_{2-6}$alkenyl-alkyl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$alkynyl-$(CH_2)_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$ cycloheteroalkyl, —$C_{2-6}$alkynyl-$C_{2-7}$cycloheteroalkenyl and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each alkyl, alkenyl and alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, and $R^2$ is selected from the group consisting of: hydrogen, halogen, —CN, —$CF_3$, —$C_{1-6}$alkyl, —$C_{2-6}$alkenyl and —$C_{2-6}$alkynyl, wherein each alkyl, alkenyl and alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, provided that if $R^2$ is hydrogen, then at least one of $R^3$ and $R^4$ is not hydrogen. In another class of this embodiment, each $R^1$ and $R^2$ is independently selected from: hydrogen, halogen, aryl, biphenyl, -heteroaryl, —$C_{2-6}$alkynyl-$(CH_2)_{1-3}$—O-aryl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{2-7}$cycloheteroalkyl, and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$ alkyl, —$OC_{1-6}$ alkyl, —$NHC_{1-6}$alkyl, and —$(C_{1-6}$alkyl$)_2$, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$ alkyl$)_2$, and wherein each cycloalkyl, cycloheteroalkyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen and halogen, and provided that if $R^1$ or $R^2$ is hydrogen, then at least one of $R^3$ and $R^4$ is not hydrogen. In a subclass of this class, $R^1$ is selected from: aryl, biphenyl, -heteroaryl, —$C_{2-6}$alkynyl-$(CH_2)_{1-3}$—O-aryl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{2-7}$cycloheteroalkyl, and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$ alkyl, and —$N(C_{1-6}$alkyl$)_2$, wherein each alkynyl is unsubstituted or substituted with 1, 2 or 3 substituents selected from: halogen, $CF_3$, —OH, —$NH_2$, —$C_{1-6}$alkyl, —$OC_{1-6}$ alkyl, —$NHC_{1-6}$alkyl, and —$N(C_{1-6}$alkyl$)_2$, and wherein each cycloalkyl, cycloheteroalkyl, phenyl, aryl and heteroaryl is unsubstituted or substituted with 1, 2, 3 or 4 substituents independently selected from $R^a$, and $R^2$ is selected from the group consisting of: hydrogen and halogen, provided that if $R^2$ is hydrogen, then at least one of $R^3$ and $R^4$ is not hydrogen. In another subclass of this class, each $R^1$ and $R^2$ is independently selected from: hydrogen, Cl, Br, F phenyl, biphenyl, pyridine, thiophene, thiazole, indole, indazole, benzofuran, benzodioxole, benzothiophene, —$C_2$alkynyl-$CH_2$—O-phenyl, —$C_2$alkynyl-phenyl, —$C_2$alkynyl-naphthalene, —$C_2$alkynyl-pyridine, —$C_2$alkynyl-thiophene, —$C_2$alkynyl-cyclopentane, —$C_2$alkynyl-piperidine, and —$CH_2C(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$ alkyl, and —$N(C_{1-6}$alkyl$)_2$, and wherein each cycloalkyl, cycloheteroalkyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, Br, Cl and F, and provided that if $R^1$ or $R^2$ is hydrogen, then at least one of $R^3$ and $R^4$ is not hydrogen. In a subclass of this subclass, $R^1$ is selected from: phenyl, biphenyl, pyridine, thiophene, thiazole, indole, indazole, benzofuran, benzodioxole, benzothiophene, —$C_2$alkynyl-$CH_2$—O-phenyl, —$C_2$alkynyl-phenyl, —$C_2$alkynyl-naphthalene, —$C_2$alkynyl-pyridine, —$C_2$alkynyl-thiophene, —$C_2$alkynyl-cyclopentane, —$C_2$alkynyl-piperidine, and —$CH_2C(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$ alkyl, and —$N(C_{1-6}$alkyl$)_2$, and wherein each cycloalkyl, cycloheteroalkyl, phenyl, aryl and heteroaryl is unsubstituted or substituted with 1, 2, 3 or 4 substituents independently selected from $R^a$, and $R^2$ is selected from the group consisting of: hydrogen, Br, Cl and F, and provided that if $R^2$ is hydrogen, then at least one of $R^3$ and $R^4$ is not hydrogen.

In another embodiment of the present invention, each $R^1$ and $R^2$ is independently selected from: hydrogen, halogen, —CN, —CF$_3$, —C$_{1-6}$alkyl, —C$_{2-6}$alkenyl, —C$_{2-6}$alkynyl, aryl, biphenyl, heteroaryl, —C$_{2-6}$alkynyl-(CH$_2$)$_{1-3}$—O-aryl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{2-7}$cycloheteroalkyl, —(CH$_2$)$_p$C(O)phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each alkyl, alkenyl and alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloheteroalkyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, halogen, —CN, —CF$_3$, —C$_{1-6}$ alkyl, —C$_{2-6}$alkenyl and —C$_{2-6}$alkynyl, and provided that if $R^1$ or $R^2$ is hydrogen, then at least one of $R^3$ and $R^4$ is not hydrogen. In a class of this embodiment, $R^1$ is selected from: aryl, biphenyl, heteroaryl, —C$_{2-6}$alkynyl-(CH$_2$)$_{1-3}$—O-aryl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{2-7}$cycloheteroalkyl, —(CH$_2$)$_p$C(O)phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$ alkyl, —NHC$_{1-6}$alkyl, and —N(C$_{1-6}$alkyl)$_2$, wherein each alkyl, alkenyl and alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloheteroalkyl, phenyl, aryl and heteroaryl is unsubstituted or substituted with 1, 2, 3 or 4 substituents independently selected from $R^a$, and $R^2$ is selected from the group consisting of: hydrogen, halogen, —CN, —CF$_3$, —C$_{1-6}$alkyl, —C$_{2-6}$alkenyl and —C$_{2-6}$alkynyl, and provided that if $R^2$ is hydrogen, then at least one of $R^3$ and $R^4$ is not hydrogen. In another class of this embodiment, each $R^1$ and $R^2$ is independently selected from: hydrogen, halogen, aryl, biphenyl, heteroaryl, —C$_{2-6}$alkynyl-(CH$_2$)$_{1-3}$—O-aryl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{2-7}$cycloheteroalkyl, and —(CH$_2$)$_p$C(O)phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$ alkyl, —NHC$_{1-6}$alkyl, and —N(C$_{1-6}$alkyl)$_2$, wherein each alkynyl is unsubstituted or substituted with 1, 2 or 3 substituents selected from: halogen, CF$_3$, —OH, —NH$_2$, —C$_{1-6}$ alkyl, —OC$_{1-6}$alkyl, —NHC$_{1-6}$alkyl, and —N(C$_{1-6}$alkyl)$_2$, and wherein each cycloalkyl, cycloheteroalkyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen and halogen, and provided that if $R^1$ or $R^2$ is hydrogen, then at least one of $R^3$ and $R^4$ is not hydrogen. In a subclass of this class, $R^1$ is selected from: aryl, biphenyl, heteroaryl, —C$_{2-6}$alkynyl-(CH$_2$)$_{1-3}$—O-aryl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{2-7}$cycloheteroalkyl, and —(CH$_2$)$_p$C(O)phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$ alkyl, —NHC$_{1-6}$alkyl, and —N(C$_{1-6}$alkyl)$_2$, wherein each alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloheteroalkyl, phenyl, aryl and heteroaryl is unsubstituted or substituted with 1, 2, 3 or 4 substituents independently selected from $R^a$, and $R^2$ is selected from the group consisting of: hydrogen and halogen, and provided that if $R^2$ is hydrogen, then at least one of $R^3$ and $R^4$ is not hydrogen. In another subclass of this class, each $R^1$ and $R^2$ is independently selected from: hydrogen, Cl, phenyl, biphenyl, pyridine, thiophene, thiazole, indole, indazole, benzofuran, benzodioxole, benzothiophene, —C$_2$alkynyl-CH$_2$—O-phenyl, —C$_2$alkynyl-phenyl, —C$_2$alkynyl-naphthalene, —C$_2$alkynyl-pyridine, —C$_2$alkynyl-thiophene, —C$_2$alkynyl-cyclopentane, —C$_2$alkynyl-piperidine, —CH$_2$C(O)phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$ alkyl, and —N(C$_{1-6}$alkyl)$_2$, and wherein each cycloalkyl, cycloheteroalkyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen and Cl, and provided that if $R^1$ or $R^2$ is hydrogen, then at least one of $R^3$ and $R^4$ is not hydrogen. In a subclass of this subclass, $R^1$ is selected from: phenyl, biphenyl, pyridine, thiophene, thiazole, indole, indazole, benzofuran, benzodioxole, benzothiophene, —C$_2$alkynyl-CH$_2$—O-phenyl, —C$_2$alkynyl-phenyl, —C$_2$alkynyl-naphthalene, —C$_2$alkynyl-pyridine, —C$_2$alkynyl-thiophene, —C$_2$alkynyl-cyclopentane, —C$_2$alkynyl-piperidine, —CH$_2$C(O)phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$ alkyl, and —N(C$_{1-6}$alkyl)$_2$, and wherein each cycloalkyl, cycloheteroalkyl, phenyl, aryl and heteroaryl is unsubstituted or substituted with 1, 2, 3 or 4 substituents independently selected from $R^a$, and $R^2$ is selected from the group consisting of hydrogen and Cl, and provided that if $R^2$ is hydrogen, then at least one of $R^3$ and $R^4$ is not hydrogen.

In another embodiment of the present invention, each $R^1$ and $R^2$ is independently selected from: halogen, —CN, —CF$_3$, —C$_{1-6}$alkyl, —C$_{2-6}$alkenyl, —C$_{2-6}$alkynyl, —C$_{3-10}$cycloalkyl, —C$_{3-7}$cycloalkyl-aryl, —C$_{3-7}$cycloalkyl-heteroaryl, —C$_{4-10}$cycloalkenyl, —C$_{4-7}$cycloalkenyl-aryl, —C$_{4-7}$cycloalkenyl-heteroaryl, aryl, biphenyl, -heteroaryl, —C$_{2-6}$alkenyl-alkyl, —C$_{2-6}$alkenyl-aryl, —C$_{2-6}$alkenyl-heteroaryl, —C$_{2-6}$alkenyl-C$_{3-7}$cycloalkyl, —C$_{2-6}$alkenyl-C$_{3-7}$cycloalkenyl, —C$_{2-6}$alkenyl-C$_{2-7}$cycloheteroalkyl, —C$_{2-6}$alkenyl-C$_{2-7}$cycloheteroalkenyl, —C$_{2-6}$alkynyl-(CH$_2$)$_{1-3}$—O-aryl, —C$_{2-6}$alkynyl-alkyl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{3-7}$cycloalkenyl, —C$_{2-6}$alkynyl-C$_{2-7}$ cycloheteroalkyl, —C$_{2-6}$alkynyl-C$_{2-7}$cycloheteroalkenyl, and —(CH$_2$)$_p$C(O)phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$ alkyl, and —N(C$_{1-6}$alkyl)$_2$, wherein each alkyl, alkenyl and alkynyl is unsubstituted or substituted with 1, 2 or 3 substituents selected from: halogen, CF$_3$, —OH, —NH$_2$, —C$_{1-6}$ alkyl, —OC$_{1-6}$alkyl, —NHC$_{1-6}$alkyl, and —N(C$_{1-6}$alkyl)$_2$, and wherein each cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: halogen, —CN, —CF$_3$, —C$_{1-6}$alkyl, —C$_{2-6}$alkenyl and —$C_{2-6}$alkynyl. In a class of this embodiment, $R^1$ is independently selected from: —$C_{3-10}$cycloalkyl, —$C_{3-7}$cycloalkyl-aryl, —$C_{3-7}$cycloalkyl-heteroaryl, —$C_{4-10}$cycloalkenyl, —$C_{4-7}$cycloalkenyl-aryl, —$C_{4-7}$cycloalkenyl-heteroaryl, aryl, biphenyl, -heteroaryl, —$C_{2-6}$alkenyl-alkyl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$alkynyl-$(CH_2)_{1-3}$—O-aryl, —$C_{2-6}$ alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$ cycloalkenyl, —$C_{2-6}$alkynyl-$C_{2-7}$cycloheteroalkyl, —$C_{2-6}$ alkynyl-$C_{2-7}$cycloheteroalkenyl, and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$ alkyl$)_2$, wherein each alkyl, alkenyl and alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, and $R^2$ is selected from the group consisting of: halogen, —CN, —$CF_3$, —$C_{1-6}$alkyl, —$C_{2-6}$alkenyl and —$C_{2-6}$alkynyl, wherein each alkyl, alkenyl and alkynyl is unsubstituted or substituted with 1, 2 or 3 substituents selected from: halogen, $CF_3$, —OH, —$NH_2$, —$C_{1-6}$ alkyl, —$OC_{1-6}$alkyl, —$NHC_{1-6}$alkyl, and —$N(C_{1-6}$alkyl$)_2$. In another class of this embodiment, each $R^1$ and $R^2$ is independently selected from: halogen, aryl, biphenyl, -heteroaryl, —$C_{2-6}$alkynyl-$(CH_2)_{1-3}$—O-aryl, —$C_{2-6}$alkynyl-aryl, —$C_{2-6}$ alkynyl-heteroaryl, —$C_{2-6}$alkynyl-$C_{3-7}$cycloalkyl, —$C_{2-6}$ alkynyl-$C_{2-7}$cycloheteroalkyl, and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$ alkyl$)_2$, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$ alkyl, and —$N(C_{1-6}$alkyl$)_2$, and wherein each cycloalkyl, cycloheteroalkyl, phenyl, aryl and heteroaryl is unsubstituted or substituted with 1, 2, 3 or 4 substituents independently selected from $R^a$, provided that at least one of and only one of $R^1$ and $R^2$ is halogen. In a subclass of this class, $R^1$ is selected from: aryl, biphenyl, -heteroaryl, —$C_{2-6}$alkynyl-$(CH_2)_{1-3}$—O-aryl, —$C_{2-6}$alkynyl-aryl, —$C_{2-6}$alkynyl-heteroaryl, —$C_{2-6}$ alkynyl-$C_{3-7}$cycloalkyl, —$C_{2-6}$alkynyl-$C_{2-7}$cycloheteroalkyl, and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$ alkyl, —$NHC_{1-6}$alkyl, and —$N(C_{1-6}$alkyl$)_2$, wherein each alkynyl is unsubstituted or substituted with 1, 2 or 3 substituents selected from: halogen, $CF_3$, —OH, —$NH_2$, —$C_{1-6}$ alkyl, —$OC_{1-6}$alkyl, —$NHC_{1-6}$alkyl, and —$N(C_{1-6}$alkyl$)_2$, and wherein each cycloalkyl, cycloheteroalkyl, phenyl, aryl and heteroaryl is unsubstituted or substituted with 1, 2, 3 or 4 substituents independently selected from $R^a$, and $R^2$ is halogen. In another subclass of this class, each $R^1$ and $R^2$ is independently selected from: Cl, Br, F phenyl, biphenyl, pyridine, thiophene, thiazole, indole, indazole, benzofuran, benzodioxole, benzothiophene, —$C_2$alkynyl-$CH_2$—O-phenyl, —$C_2$alkynyl-phenyl, —$C_2$alkynyl-naphthalene, —$C_2$alkynyl-pyridine, —$C_2$alkynyl-thiophene, —$C_2$alkynyl-cyclopentane, —$C_2$alkynyl-piperidine, and —$CH_2C(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$ alkyl, and —$N(C_{1-6}$alkyl$)_2$, and wherein each cycloalkyl, cycloheteroalkyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: Br, Cl and F. In a subclass of this subclass, $R^1$ is independently selected from: phenyl, biphenyl, pyridine, thiophene, thiazole, indole, indazole, benzofuran, benzodioxole, benzothiophene, —$C_2$alkynyl-$CH_2$—O-phenyl, —$C_2$alkynyl-phenyl, —$C_2$alkynyl-naphthalene, —$C_2$alkynyl-pyridine, —$C_2$alkynyl-thiophene, —$C_2$alkynyl-cyclopentane, —$C_2$alkynyl-piperidine, and —$CH_2C(O)$phenyl, wherein each $CH_2$ is unsubstituted or substituted with 1 or 2 substituents selected from: halogen, $CF_3$, —OH, —$NH_2$, —$C_{1-6}$ alkyl, —$OC_{1-6}$alkyl, —$NHC_{1-6}$alkyl, and —$N(C_{1-6}$alkyl$)_2$, and wherein each cycloalkyl, cycloheteroalkyl, phenyl, aryl and heteroaryl is unsubstituted or substituted with 1, 2, 3 or 4 substituents independently selected from $R^a$, and $R^2$ is selected from the group consisting of Br, Cl and F.

In another embodiment of the present invention, each $R^1$ and $R^2$ is independently selected from: halogen, —CN, —$CF_3$, —$C_{1-6}$alkyl, —$C_{2-6}$alkenyl, —$C_{2-6}$alkynyl, aryl, biphenyl, heteroaryl, —$C_{2-6}$alkynyl-$(CH_2)_{1-3}$—O-aryl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{2-7}$cycloheteroalkyl, —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$ alkyl, and —$N(C_{1-6}$alkyl$)_2$, wherein each alkyl, alkenyl and alkynyl is unsubstituted or substituted with 1, 2 or 3 substituents selected from: halogen, $CF_3$, —OH, —$NH_2$, —$C_{1-6}$ alkyl, —$OC_{1-6}$alkyl, —$NHC_{1-6}$alkyl, and —$N(C_{1-6}$alkyl$)_2$, and wherein each cycloalkyl, cycloheteroalkyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of halogen, —CN, —$CF_3$, —$C_{1-6}$alkyl, —$C_{2-6}$alkenyl and —$C_{2-6}$alkynyl. In a class of this embodiment, $R^1$ is selected from: aryl, biphenyl, heteroaryl, —$C_{2-6}$ alkynyl-$(CH_2)_{1-3}$—O-aryl, —$C_{2-6}$alkynyl-aryl, —$C_{2-6}$alkynyl-heteroaryl, —$C_{2-6}$alkynyl-$C_{3-7}$cycloalkyl, —$C_{2-6}$ alkynyl-$C_{2-7}$cycloheteroalkyl, —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$ alkyl, —$OC_{1-6}$alkyl, —$NHC_{1-6}$alkyl, and —$N(C_{1-6}$alkyl$)_2$, wherein each alkyl, alkenyl and alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$ alkyl, and —$N(C_{1-6}$alkyl$)_2$, and wherein each cycloalkyl, cycloheteroalkyl, phenyl, aryl and heteroaryl is unsubstituted or substituted with 1, 2, 3 or 4 substituents independently selected from $R^a$, and $R^2$ is selected from the group consisting of: halogen, —CN, —$CF_3$, —$C_{1-6}$alkyl, —$C_{2-6}$alkenyl and —$C_{2-6}$alkynyl. In another class of this embodiment, each $R^1$ and $R^2$ is independently selected from: halogen, aryl, biphenyl, heteroaryl, —$C_{2-6}$alkynyl-$(CH_2)_{1-3}$—O-aryl, —$C_{2-6}$ alkynyl-aryl, —$C_{2-6}$alkynyl-heteroaryl, —$C_{2-6}$alkynyl-$C_{3-7}$ cycloalkyl, —$C_{2-6}$alkynyl-$C_{2-7}$cycloheteroalkyl, and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$ alkyl, and —$N(C_{1-6}$alkyl$)_2$, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloalkyl, cycloheteroalkyl, phenyl, aryl and heteroaryl is unsubstituted or substituted with 1, 2 or 3 substituents independently selected from $R^a$, provided that at least one of and only one of $R^1$ and $R^2$ is halogen. In a subclass of this class, $R^1$ is selected from: aryl, biphenyl, heteroaryl, $—C_{2-6}$alkynyl-$(CH_2)_{1-3}$—O-aryl, $—C_{2-6}$alkynyl-aryl, $—C_{2-6}$alkynyl-heteroaryl, $—C_{2-6}$alkynyl-$C_{3-7}$cycloalkyl, $—C_{2-6}$ alkynyl-$C_{2-7}$ cycloheteroalkyl, and $—(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$ alkyl$)_2$, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$ alkyl, and —$N(C_{1-6}$ alkyl$)_2$, and wherein each cycloalkyl, cycloheteroalkyl, phenyl, aryl and heteroaryl is unsubstituted or substituted with 1, 2 or 3 substituents independently selected from $R^a$, and $R^2$ is halogen. In another subclass of this class, each $R^1$ and $R^2$ is independently selected from: Cl, phenyl, biphenyl, pyridine, thiophene, thiazole, indole, indazole, benzofuran, benzodioxole, benzothiophene, $—C_2$alkynyl-$CH_2$—O-phenyl, $—C_2$alkynyl-phenyl, $—C_2$alkynyl-naphthalene, $—C_2$alkynyl-pyridine, $—C_2$alkynyl-thiophene, $—C_2$alkynyl-cyclopentane, $—C_2$alkynyl-piperidine, $—CH_2C(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$ alkyl, and —$N(C_{1-6}$alkyl$)_2$, and wherein each cycloalkyl, cycloheteroalkyl, phenyl, aryl and heteroaryl is unsubstituted or substituted with 1, 2 or 3 substituents independently selected from $R^a$, provided that at least one of and only one of $R^1$ and $R^2$ is Cl. In a subclass of this subclass, $R^1$ is selected from: phenyl, biphenyl, pyridine, thiophene, thiazole, indole, indazole, benzofuran, benzodioxole, benzothiophene, $—C_2$alkynyl-$CH_2$—O-phenyl, $—C_2$alkynyl-phenyl, $—C_2$alkynyl-naphthalene, $—C_2$alkynyl-pyridine, $—C_2$alkynyl-thiophene, $—C_2$alkynyl-cyclopentane, $—C_2$alkynyl-piperidine, $—CH_2C(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$ alkyl, and —$N(C_{1-6}$alkyl$)_2$, and wherein each cycloalkyl, cycloheteroalkyl, phenyl, aryl and heteroaryl is unsubstituted or substituted with 1, 2 or 3 substituents independently selected from $R^a$, and $R^2$ is Cl.

In another embodiment of the present invention, each $R^1$ and $R^2$ is independently selected from: hydrogen, halogen, aryl, biphenyl, $—(CH_2)_p$heteroaryl, $—C_{2-6}$alkynyl-$(CH_2)_{1-3}$—O-aryl, $—C_{2-6}$alkynyl-aryl, $—C_{2-6}$alkynyl-heteroaryl, $—C_{2-6}$alkynyl-$C_{3-7}$cycloalkyl, $—C_{2-6}$alkynyl-$C_{2-7}$cycloheteroalkyl, and $—(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloalkyl, cycloheteroalkyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen and halogen, and provided that if $R^1$ or $R^2$ is hydrogen, then at least one of $R^3$ and $R^4$ is not hydrogen. In a class of this embodiment, $R^1$ is selected from: aryl, biphenyl, $—(CH_2)_p$heteroaryl, $—C_{2-6}$alkynyl-$(CH_2)_{1-3}$—O-aryl, $—C_{2-6}$alkynyl-aryl, $—C_{2-6}$alkynyl-heteroaryl, $—C_{2-6}$alkynyl-$C_{3-7}$cycloalkyl, $—C_{2-6}$alkynyl-$C_{2-7}$cycloheteroalkyl, and $—(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloalkyl, cycloheteroalkyl, phenyl, aryl and heteroaryl is unsubstituted or substituted with 1, 2 or 3 substituents independently selected from $R^a$, and $R^2$ is selected from the group consisting of: hydrogen and halogen, and provided that if $R^2$ is hydrogen, then at least one of $R^3$ and $R^4$ is not hydrogen. In another class of this embodiment, each $R^1$ and $R^2$ is independently selected from: hydrogen, halogen, aryl, biphenyl, heteroaryl, $—C_{2-6}$alkynyl-$CH_2$—O-phenyl, $—C_{2-6}$alkynyl-phenyl, $—C_{2-6}$alkynyl-naphthalene, $—C_{2-6}$alkynyl-heteroaryl, $—C_{2-6}$alkynyl-$C_{3-7}$cycloalkyl, $—C_{2-6}$alkynyl-$C_{2-7}$cycloheteroalkyl, and $—(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloalkyl, cycloheteroalkyl, phenyl, aryl and heteroaryl is unsubstituted or substituted with 1, 2 or 3 substituents independently selected from $R^a$, provided that at least one of and only one of $R^1$ and $R^2$ is selected from the group consisting of: hydrogen and halogen, and provided that if $R^1$ or $R^2$ is hydrogen, then at least one of $R^3$ and $R^4$ is not hydrogen. In a subclass of this class, $R^1$ is selected from: aryl, biphenyl, heteroaryl, $—C_{2-6}$alkynyl-$CH_2$—O-phenyl, $—C_{2-6}$alkynyl-phenyl, $—C_{2-6}$alkynyl-naphthalene, $—C_{2-6}$alkynyl-heteroaryl, $—C_{2-6}$alkynyl-$C_{3-7}$cycloalkyl, $—C_{2-6}$alkynyl-$C_{2-7}$ cycloheteroalkyl, and $—(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloalkyl, cycloheteroalkyl, phenyl, aryl and heteroaryl is unsubstituted or substituted with 1, 2 or 3 substituents independently selected from $R^a$, provided that at least one of and only one of $R^1$ and $R^2$ is selected from the group consisting of: hydrogen and halogen, and provided that if $R^1$ or $R^2$ is hydrogen, then at least one of $R^3$ and $R^4$ is not hydrogen. In a subclass of this class, $R^1$ is selected from: aryl, biphenyl, heteroaryl, $—C_{2-6}$alkynyl-$CH_2$—O-phenyl, $—C_{2-6}$alkynyl-phenyl, $—C_{2-6}$alkynyl-naphthalene, $—C_{2-6}$alkynyl-pyridine, $—C_{2-6}$alkynyl-thiophene, $—C_2$alkynyl-$C_{3-7}$cycloalkyl, $—C_2$alkynyl-$C_{2-7}$cycloheteroalkyl, and $—(CH_2)_pC(O)$phenyl, wherein each $CH_2$ is unsubstituted or substituted with 1 or 2 substituents selected from: halogen, $CF_3$, —OH, —$NH_2$, —$C_{1-6}$ alkyl, —$OC_{1-6}$alkyl, —$NHC_{1-6}$alkyl, and —$N(C_{1-6}alkyl)_2$, and wherein each cycloalkyl, cycloheteroalkyl, phenyl, aryl and heteroaryl is unsubstituted or substituted with 1, 2 or 3 substituents independently selected from $R^a$, and $R^2$ is selected from the group consisting of: hydrogen and halogen, and provided that if $R^2$ is hydrogen, then at least one of $R^3$ and $R^4$ is not hydrogen. In another class of this embodiment, each $R^1$ and $R^2$ is independently selected from: hydrogen, Cl, phenyl, biphenyl, pyridine, thiophene, thiazole, indole, indazole, benzofuran, benzodioxole, benzothiophene, —$C_2$alkynyl-$CH_2$—O-phenyl, —$C_2$alkynyl-phenyl, —$C_2$alkynyl-naphthalene, —$C_2$alkynyl-pyridine, —$C_2$alkynyl-thiophene, —$C_2$alkynyl-cyclopentane, —$C_2$alkynyl-piperidine, and —$CH_2C(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloheteroalkyl, phenyl, aryl and heteroaryl is unsubstituted or substituted with 1, 2 or 3 substituents independently selected from $R^a$, provided that at least one of and only one of $R^1$ and $R^2$ is selected from the group consisting of: hydrogen and Cl, and provided that if $R^1$ or $R^2$ is hydrogen, then at least one of $R^3$ and $R^4$ is not hydrogen. In a subclass of this class, $R^1$ is selected from: phenyl, biphenyl, pyridine, thiophene, thiazole, indole, indazole, benzofuran, benzodioxole, benzothiophene, —$C_2$alkynyl-$CH_2$—O-phenyl, —$C_2$alkynyl-phenyl, —$C_2$alkynyl-naphthalene, —$C_2$alkynyl-pyridine, —$C_2$alkynyl-thiophene, —$C_2$alkynyl-cyclopentane, —$C_2$alkynyl-piperidine, and —$CH_2C(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloheteroalkyl, phenyl, aryl and heteroaryl is unsubstituted or substituted with 1, 2 or 3 substituents independently selected from $R^a$, and $R^2$ is selected from the group consisting of: hydrogen and Cl, and provided that if $R^2$ is hydrogen, then at least one of $R^3$ and $R^4$ is not hydrogen.

In another embodiment of the present invention, each $R^1$ and $R^2$ is independently selected from: halogen, aryl, biphenyl, —$(CH_2)_p$heteroaryl, —$C_{2-6}$alkynyl-$(CH_2)_{1-3}$—O-aryl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{2-7}$cycloheteroalkyl, and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloheteroalkyl, phenyl, aryl and heteroaryl is unsubstituted or substituted with 1, 2, 3 or 4 substituents independently selected from $R^a$, provided that at least one of and only one of $R^1$ and $R^2$ is halogen. In a class of this embodiment, $R^1$ is selected from: aryl, biphenyl, —$(CH_2)_p$heteroaryl, —$C_{2-6}$alkynyl-$(CH_2)_{1-3}$—O-aryl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{2-7}$cycloheteroalkyl, and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkynyl is unsubstituted or substituted with 1, 2 or 3 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloheteroalkyl, phenyl, aryl and heteroaryl is unsubstituted or substituted with 1, 2, 3 or 4 substituents independently selected from $R^a$, and $R^2$ is halogen. In another class of this embodiment, each $R^1$ and $R^2$ is independently selected from: halogen, aryl, biphenyl, heteroaryl, —$C_{2-6}$alkynyl-$CH_2$—O-phenyl, —$C_{2-6}$alkynyl-phenyl, —$C_{2-6}$alkynyl-naphthalene, —$C_{2-6}$alkynyl-heteroaryl, —$C_{2-6}$alkynyl-$C_{3-7}$cycloalkyl, —$C_{2-6}$alkynyl-$C_{2-7}$cycloheteroalkyl, and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloheteroalkyl, phenyl, aryl and heteroaryl is unsubstituted or substituted with 1, 2 or 3 substituents independently selected from $R^a$, provided that at least one of and only one of $R^1$ and $R^2$ is halogen. In a subclass of this class, $R^1$ is selected from: aryl, biphenyl, heteroaryl, —$C_{2-6}$alkynyl-$CH_2$—O-phenyl, —$C_{2-6}$alkynyl-phenyl, —$C_{2-6}$alkynyl-naphthalene, —$C_{2-6}$alkynyl-heteroaryl, —$C_{2-6}$alkynyl-$C_{3-7}$cycloalkyl, —$C_{2-6}$alkynyl-$C_{2-7}$cycloheteroalkyl, and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloheteroalkyl, phenyl, aryl and heteroaryl is unsubstituted or substituted with 1, 2 or 3 substituents independently selected from $R^a$, and $R^2$ is halogen. In another class of this embodiment, each $R^1$ and $R^2$ is independently selected from: halogen, aryl, biphenyl, heteroaryl, —$C_{2-6}$alkynyl-$CH_2$—O-phenyl, —$C_{2-6}$alkynyl-phenyl, —$C_{2-6}$alkynyl-naphthalene, —$C_{2-6}$alkynyl-pyridine, —$C_{2-6}$alkynyl-thiophene, —$C_2$alkynyl-$C_{3-7}$cycloalkyl, —$C_2$alkynyl-$C_{2-7}$cycloheteroalkyl, and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloheteroalkyl, phenyl, aryl and heteroaryl is unsubstituted or substituted with 1, 2 or 3 substituents independently selected from $R^a$, provided that at least one of and only one of $R^1$ and $R^2$ is halogen. In a subclass of this class, $R^1$ is selected from: aryl, biphenyl, heteroaryl, —$C_{2-6}$alkynyl-$CH_2$—O-phenyl, —$C_{2-6}$alkynyl-phenyl, —$C_{2-6}$alkynyl-naphthalene, —$C_{2-6}$alkynyl-pyridine, —$C_{2-6}$alkynyl-thiophene, —$C_2$alkynyl-$C_{3-7}$cycloalkyl, —$C_2$alkynyl-$C_{2-7}$cycloheteroalkyl, and —$(CH_2)_pC(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloheteroalkyl, phenyl, aryl and heteroaryl is unsubstituted or substituted with 1, 2 or 3 substituents independently selected from $R^a$, and $R^2$ is halogen. In another class of this embodiment, each $R^1$ and $R^2$ is independently selected from: Cl, phenyl, biphenyl, pyridine, thiophene, thiazole, indole, indazole, benzofuran, benzodioxole, benzothiophene, —$C_2$alkynyl-$CH_2$—O-phenyl, —$C_2$alkynyl-phenyl, —$C_2$alkynyl-naphthalene, —$C_2$alkynyl-pyridine, —$C_2$alkynyl-thiophene, —$C_2$alkynyl-cyclopentane, —$C_2$alkynyl-piperidine, and —$CH_2C(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each cycloalkyl, cycloheteroalkyl, phenyl, aryl and heteroaryl is unsubstituted or substituted with 1, 2 or 3 substituents independently selected from $R^a$, provided that at least one of and only one of $R^1$ and $R^2$ is Cl. In a subclass of this class, $R^1$ is selected from: phenyl, biphenyl, pyridine, thiophene, thiazole, indole, indazole, benzofuran, benzodioxole, benzothiophene, —$C_2$alkynyl-$CH_2$—O-phenyl, —$C_2$alkynyl-phenyl, —$C_2$alkynyl-naphthalene, —$C_2$alkynyl-pyridine, —$C_2$alkynyl-thiophene, —$C_2$alkynyl-cyclopentane, —$C_2$alkynyl-piperidine, and —$CH_2C(O)$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloalkyl, cycloheteroalkyl, phenyl, aryl and heteroaryl is unsubstituted or substituted with 1, 2 or 3 substituents independently selected from $R^a$, and $R^2$ is Cl.

In another embodiment of the present invention, each $R^1$ and $R^2$ is independently selected from: hydrogen, halogen, aryl, biphenyl, and —$C_{2-6}$alkynyl-aryl, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each phenyl and aryl is unsubstituted or substituted with 1, 2, 3 or 4 substituents independently selected from $R^a$, provided that at least one of and only one of $R^1$ and $R^2$ is selected from the group consisting of: hydrogen and halogen, and provided that if $R^1$ or $R^2$ is hydrogen, then at least one of $R^3$ and $R^4$ is not hydrogen. In a class of this embodiment, $R^1$ is selected from: aryl, biphenyl, and —$C_{2-6}$alkynyl-aryl, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each phenyl and aryl is unsubstituted or substituted with 1, 2, 3 or 4 substituents independently selected from $R^a$, and $R^2$ is selected from the group consisting of: hydrogen and halogen, provided that if $R^2$ is hydrogen, then at least one of $R^3$ and $R^4$ is not hydrogen. In another class of this embodiment, each $R^1$ and $R^2$ is independently selected from: hydrogen, halogen, phenyl, biphenyl, and —$C_{2-6}$alkynyl-phenyl, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each phenyl and aryl is unsubstituted or substituted with 1, 2 or 3 substituents independently selected from $R^a$, provided that at least one of and only one of $R^1$ and $R^2$ is selected from the group consisting of: hydrogen and halogen, and provided that if $R^1$ or $R^2$ is hydrogen, then at least one of $R^3$ and $R^4$ is not hydrogen. In a subclass of this class, $R^1$ is selected from: phenyl, biphenyl, and —$C_{2-6}$alkynyl-phenyl, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each phenyl and aryl is unsubstituted or substituted with 1, 2 or 3 substituents independently selected from $R^a$, and $R^2$ is selected from the group consisting of hydrogen and halogen, and provided that if $R^2$ is hydrogen, then at least one of $R^3$ and $R^4$ is not hydrogen. In another subclass of this class, each $R^1$ and $R^2$ is independently selected from: hydrogen, Cl, phenyl, biphenyl, and —$C_2$alkynyl-phenyl, wherein each phenyl is unsubstituted or substituted with 1, 2 or 3 substituents independently selected from $R^a$, provided that at least one of and only one of $R^1$ and $R^2$ is selected from the group consisting of: hydrogen and Cl, and provided that if $R^1$ or $R^2$ is hydrogen, then at least one of $R^3$ and $R^4$ is not hydrogen. In a subclass of this subclass, $R^1$ is selected from: phenyl, biphenyl, and —$C_2$alkynyl-phenyl, wherein each phenyl is unsubstituted or substituted with 1, 2 or 3 substituents independently selected from $R^a$, and $R^2$ is selected from the group consisting of: hydrogen and Cl, and provided that if $R^2$ is hydrogen, then at least one of $R^3$ and $R^4$ is not hydrogen.

In another embodiment of the present invention, each $R^1$ and $R^2$ is independently selected from: halogen, aryl, biphenyl, and —$C_{2-6}$alkynyl-aryl, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each phenyl and aryl is unsubstituted or substituted with 1, 2, 3 or 4 substituents independently selected from $R^a$, provided that at least one of and only one of $R^1$ and $R^2$ is halogen. In a class of this embodiment, $R^1$ is selected from: aryl, biphenyl, and —$C_{2-6}$alkynyl-aryl, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each phenyl and aryl is unsubstituted or substituted with 1, 2, 3 or 4 substituents independently selected from $R^a$, and $R^2$ is halogen. In another class of this embodiment, each $R^1$ and $R^2$ is independently selected from: halogen, phenyl, biphenyl, and —$C_{2-6}$alkynyl-phenyl, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each phenyl is unsubstituted or substituted with 1, 2 or 3 substituents independently selected from $R^a$, provided that at least one of and only one of $R^1$ and $R^2$ is halogen. In a subclass of this class, $R^1$ is selected from: phenyl, biphenyl, and —$C_{2-6}$alkynyl-phenyl, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each phenyl is unsubstituted or substituted with 1, 2 or 3 substituents independently selected from $R^a$, and $R^2$ is halogen. In a subclass of this class, each $R^1$ and $R^2$ is independently selected from: Cl, phenyl, biphenyl, and —$C_2$alkynyl-phenyl, wherein each phenyl is unsubstituted or substituted with 1, 2 or 3 substituents independently selected from $R^a$, provided that at least one of and only one of $R^1$ and $R^2$ is Cl. In a subclass of this subclass, $R^1$ is independently selected from: phenyl, biphenyl, and —$C_2$alkynyl-phenyl, wherein each phenyl is unsubstituted or substituted with 1, 2 or 3 substituents independently selected from $R^a$, and $R^2$ is Cl.

In another embodiment of the present invention, $R^1$ is selected from: phenyl and biphenyl, wherein each phenyl is unsubstituted or substituted with 1, 2 or 3 substituents independently selected from $R^a$, and $R^2$ is selected from the group consisting of: hydrogen and halogen, and provided that if $R^2$ is hydrogen, then at least one of $R^3$ and $R^4$ is not hydrogen. In another embodiment of the present invention, $R^1$ is selected from: phenyl and biphenyl, wherein each phenyl is unsubstituted or substituted with 1, 2 or 3 substituents independently selected from $R^a$, and $R^2$ is Cl.

In another embodiment of the present invention, each $R^1$ and $R^2$ is independently selected from: halogen, phenyl, biphenyl, heteroaryl, and —$C_2$alkynyl-phenyl, wherein each phenyl and heteroaryl is unsubstituted or substituted with 1, 2 or 3 substituents independently selected from $R^a$, provided that at least one of and only one of $R^1$ and $R^2$ is Cl. In a class of this embodiment, each $R^1$ and $R^2$ is independently selected from: Cl, phenyl, biphenyl, indole, and —$C_2$alkynyl-phenyl, wherein each phenyl and heteroaryl is unsubstituted or substituted with 1 or 2 substituents independently selected from $R^a$, provided that at least one of and only one of $R^1$ and $R^2$ is halogen. In a class of this embodiment, $R^1$ is independently selected from: phenyl, biphenyl, heteroaryl, and —$C_2$alkynyl-phenyl, wherein each phenyl and heteroaryl is unsubstituted or substituted with 1, 2 or 3 substituents independently selected from $R^a$, and $R^2$ is halogen. In a class of this embodiment, $R^1$ is selected from: phenyl, biphenyl, indole, and —$C_2$alkynyl-phenyl, wherein each phenyl and heteroaryl is unsubstituted or substituted with 1 or 2 substituents independently selected from $R^a$, and $R^2$ is halogen.

In another embodiment of the present invention, each $R^1$ and $R^2$ is independently selected from: Cl, phenyl, biphenyl, heteroaryl, and —$C_2$alkynyl-phenyl, wherein each phenyl and heteroaryl is unsubstituted or substituted with 1, 2 or 3 substituents independently selected from $R^a$, provided that at least one of and only one of $R^1$ and $R^2$ is Cl. In a class of this embodiment, each $R^1$ and $R^2$ is independently selected from: Cl, phenyl, biphenyl, indole, and —$C_2$alkynyl-phenyl, wherein each phenyl and heteroaryl is unsubstituted or substituted with 1 or 2 substituents independently selected from $R^a$, provided that at least one of and only one of $R^1$ and $R^2$ is Cl. In a class of this embodiment, $R^1$ is selected from: phenyl, biphenyl, heteroaryl, and —$C_2$alkynyl-phenyl, wherein each phenyl and heteroaryl is unsubstituted or substituted with 1, 2 or 3 substituents independently selected from $R^a$, provided that at least one of and only one of $R^1$ and $R^2$ is Cl. In a class of this embodiment, each $R^1$ and $R^2$ is independently selected from: Cl, phenyl, biphenyl, indole, and —$C_2$alkynyl-phenyl, wherein each phenyl and heteroaryl is unsubstituted or substituted with 1 or 2 substituents independently selected from $R^a$, and $R^2$ is Cl. In another class of this embodiment, each $R^1$ and $R^2$ is independently selected from: Cl, phenyl, biphenyl, indole, and —$C_2$alkynyl-phenyl, wherein each phenyl and heteroaryl is unsubstituted or substituted with 1 or 2 substituents independently selected from $R^a$, provided that at least one of and only one of $R^1$ and $R^2$ is Cl. In a subclass of this class, $R^1$ is selected from: phenyl, biphenyl, indole, and —$C_2$alkynyl-phenyl, wherein each phenyl and heteroaryl is unsubstituted or substituted with 1 or 2 substituents selected from $R^a$, and $R^2$ is Cl.

In another embodiment of the present invention, each $R^1$ and $R^2$ is independently selected from: Cl, phenyl, biphenyl, and —$C_2$alkynyl-phenyl, wherein each phenyl is unsubstituted or substituted with 1, 2 or 3 substituents independently selected from $R^a$, provided that at least one of and only one of $R^1$ and $R^2$ is Cl. In a class of this embodiment, $R^1$ is selected from: phenyl, biphenyl, and —$C_2$alkynyl-phenyl, wherein each phenyl is unsubstituted or substituted with 1, 2 or 3 substituents independently selected from $R^a$, and $R^2$ is Cl.

In another embodiment of the present invention, $R^3$ and $R^4$ are each independently selected from: hydrogen, halogen, —$C_{1-6}$alkyl, —$C_{2-6}$alkenyl, —$C_{2-6}$alkynyl, —$C_{3-10}$cycloalkyl, —$C_{3-10}$cycloalkenyl, aryl, heteroaryl, —CN, —$CF_3$, —OH, —$OC_{1-6}$alkyl, —$NH_2$, —$NHC_{1-6}$alkyl, —$N(C_{1-6}$alkyl$)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In a class of this embodiment, $R^3$ and $R^4$ are each independently selected from: hydrogen, F, Br and Cl. In another subclass of this class, $R^3$ and $R^4$ are each independently selected from: hydrogen, F and Cl. In another subclass of this class, $R^3$ and $R^4$ are each independently selected from: hydrogen and Cl. In another subclass of this class, $R^3$ is hydrogen, and $R^4$ is independently selected from: hydrogen and Cl. In another class of this embodiment, $R^3$ and $R^4$ are each independently selected from: hydrogen, halogen, —$C_{1-6}$alkyl, —$C_{2-6}$alkenyl, —$C_{2-6}$alkynyl, —CN, —$CF_3$, —OH, —$OC_{1-6}$alkyl, —$NH_2$, —$NHC_{1-6}$alkyl, —$N(C_{1-6}$alkyl$)_2$, and —$SC_{1-6}$alkyl. In a subclass of this class, $R^3$ and $R^4$ are each independently selected from: hydrogen, F, Br and Cl. In another subclass of this class, $R^3$ and $R^4$ are each independently selected from: hydrogen, F and Cl. In another subclass of this class, $R^3$ and $R^4$ are each independently selected from: hydrogen and Cl. In another subclass of this class, $R^3$ is hydrogen, and $R^4$ is independently selected from: hydrogen and Cl. In another class of this embodiment, $R^3$ and $R^4$ are each independently selected from: hydrogen, halogen, and —$C_{1-6}$alkyl. In a subclass of this class, $R^3$ and $R^4$ are each independently selected from: hydrogen, F, Br and Cl. In another subclass of this class, $R^3$ and $R^4$ are each independently selected from: hydrogen, F and Cl. In another subclass of this class, $R^3$ and $R^4$ are each independently selected from: hydrogen and Cl. In another subclass of this class, $R^3$ is hydrogen and $R^4$ is independently selected from: hydrogen and Cl.

In another embodiment of the present invention, $R^3$ and $R^4$ are each independently selected from: hydrogen and halogen. In a subclass of this class, $R^3$ and $R^4$ are each independently selected from: hydrogen, F, Br and Cl. In another subclass of this class, $R^3$ and $R^4$ are each independently selected from: hydrogen, F and Cl. In another subclass of this class, $R^3$ and $R^4$ are each independently selected from: hydrogen and Cl. In another subclass of this class, $R^3$ and $R^4$ are both hydrogen. In another subclass of this class, $R^3$ and $R^4$ are both Cl. In another subclass of this class, $R^3$ is hydrogen, and $R^4$ is independently selected from: hydrogen and halogen. In another subclass of this class, $R^3$ is hydrogen, and $R^4$ is independently selected from: hydrogen and Cl. In another subclass of this class, both $R^3$ and $R^4$ are hydrogen.

In another embodiment of the present invention, $R^3$ is independently selected from: hydrogen, halogen, —$C_{1-6}$alkyl, —$C_{2-6}$alkenyl, —$C_{2-6}$alkynyl, —$C_{3-10}$cycloalkyl, —$C_{3-10}$cycloalkenyl, aryl, heteroaryl, —CN, —$CF_3$, —OH, —$OC_{1-6}$alkyl, —$NH_2$, —$NHC_{1-6}$alkyl, —$N(C_{1-6}$alkyl$)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In a class of this embodiment, $R^3$ is independently selected from: hydrogen, F, Br and Cl. In another subclass of this class, $R^3$ is independently selected from: hydrogen, F and Cl. In another subclass of this class, $R^3$ is independently selected from: hydrogen and Cl. In another subclass of this class, $R^3$ is hydrogen. In a class of this embodiment, $R^3$ is independently selected from: hydrogen, halogen, —$C_{1-6}$alkyl, —$C_{2-6}$alkenyl, —$C_{2-6}$alkynyl, —CN, —$CF_3$, —OH, —$OC_{1-6}$alkyl, —$NH_2$, —$NHC_{1-6}$alkyl, —$N(C_{1-6}$alkyl$)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In a class of this embodiment, $R^3$ is independently selected from: hydrogen, F, Br and Cl. In another subclass of this class, $R^3$ is independently selected from: hydrogen, F and Cl. In another subclass of this class, $R^3$ is independently selected from: hydrogen and Cl. In another subclass of this class, $R^3$ is hydrogen. In another class of this embodiment, $R^3$ is independently selected from: hydrogen, halogen, —$C_{1-6}$alkyl, —$C_{2-6}$alkenyl, —$C_{2-6}$alkynyl, —CN, —$CF_3$, —OH, —$OC_{1-6}$ alkyl, —$NH_2$, —$NHC_{1-6}$alkyl, —$N(C_{1-6}alkyl)_2$, and —$SC_{1-6}$ alkyl. In a class of this embodiment, $R^3$ is independently selected from: hydrogen, F, Br and Cl. In another subclass of this class, $R^3$ is independently selected from: hydrogen, F and Cl. In another subclass of this class, $R^3$ is independently selected from: hydrogen and Cl. In another subclass of this class, $R^3$ is hydrogen. In another class of this embodiment, $R^3$ is independently selected from: hydrogen, halogen, and —$C_{1-6}$alkyl. In a subclass of this class, $R^3$ is independently selected from: hydrogen, F, Br and Cl. In another subclass of this class, $R^3$ is independently selected from: hydrogen, F and Cl. In another subclass of this class, $R^3$ is independently selected from: hydrogen and Cl. In another subclass of this class, $R^3$ is hydrogen.

In another embodiment of the present invention, $R^3$ is independently selected from: hydrogen and halogen. In a subclass of this class, $R^3$ is independently selected from: hydrogen, F, Br and Cl. In another subclass of this class, $R^3$ is independently selected from: hydrogen, F and Cl. In another subclass of this class, $R^3$ is independently selected from: hydrogen and Cl. In another subclass of this class, $R^3$ is hydrogen. In another subclass of this class, $R^3$ is Cl.

In another embodiment of the present invention, $R^4$ is independently selected from: hydrogen, halogen, —$C_{1-6}$alkyl, —$C_{2-6}$alkenyl, —$C_{2-6}$alkynyl, —$C_{3-10}$cycloalkyl, —$C_{3-10}$cycloalkenyl, aryl, heteroaryl, —CN, —$CF_3$, —OH, —$OC_{1-6}$alkyl, —$NH_2$, —$NHC_{1-6}$alkyl, —$N(C_{1-6}alkyl)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In a class of this embodiment, $R^4$ is independently selected from: hydrogen, F, Br and Cl. In another subclass of this class, $R^4$ is independently selected from: hydrogen, F and Cl. In another subclass of this class, $R^4$ is independently selected from: hydrogen and Cl. In another subclass of this class, $R^4$ is hydrogen. In another subclass of this class, $R^4$ is Cl. In a class of this embodiment, $R^4$ is independently selected from: hydrogen, halogen, —$C_{1-6}$alkyl, —$C_{2-6}$alkenyl, —$C_{2-6}$alkynyl, —CN, —$CF_3$, —OH, —$OC_{1-6}$alkyl, —$NH_2$, —$NHC_{1-6}$alkyl, —$N(C_{1-6}alkyl)_2$, —$SC_{1-6}$alkyl, —$SOC_{1-6}$alkyl, —$SO_2C_{1-6}$alkyl, —$NHSO_2C_{1-6}$alkyl, —$NHC(O)C_{1-6}$alkyl, —$SO_2NHC_{1-6}$alkyl, and —$C(O)NHC_{1-6}$alkyl. In a subclass of this class, $R^4$ is independently selected from: hydrogen, F, Br and Cl. In another subclass of this class, $R^4$ is independently selected from: hydrogen, F and Cl. In another subclass of this class, $R^4$ is independently selected from: hydrogen and Cl. In another subclass of this class, $R^4$ is hydrogen. In another subclass of this class, $R^4$ is Cl. In another class of this embodiment, $R^4$ is independently selected from: hydrogen, halogen, —$C_{1-6}$alkyl, —$C_{2-6}$alkenyl, —$C_{2-6}$alkynyl, —CN, —$CF_3$, —OH, —$OC_{1-6}$alkyl, —$NH_2$, —$NHC_{1-6}$alkyl, —$N(C_{1-6}alkyl)_2$, and —$SC_{1-6}$alkyl. In a subclass of this class, $R^4$ is independently selected from: hydrogen, F, Br and Cl. In another subclass of this class, $R^4$ is independently selected from: hydrogen, F and Cl. In another subclass of this class, $R^4$ is independently selected from: hydrogen and Cl. In another subclass of this class, $R^4$ is hydrogen. In another subclass of this class, $R^4$ is Cl. In another class of this embodiment, $R^4$ is independently selected from: hydrogen, halogen, and —$C_{1-6}$alkyl. In a subclass of this class, $R^4$ is independently selected from: hydrogen, F, Br and Cl. In another subclass of this class, $R^4$ is independently selected from: hydrogen, F and Cl. In another subclass of this class, $R^4$ is independently selected from: hydrogen and Cl. In another subclass of this class, $R^4$ is hydrogen. In another subclass of this class, $R^4$ is Cl.

In another embodiment of the present invention, $R^4$ is independently selected from: hydrogen, and halogen. In a subclass of this class, $R^4$ is independently selected from: hydrogen, F, Br and Cl. In another subclass of this class, $R^4$ is independently selected from: hydrogen, F and Cl. In another subclass of this class, $R^4$ is independently selected from: hydrogen and Cl. In another subclass of this class, $R^4$ is hydrogen. In another subclass of this class, $R^4$ is Cl.

In another embodiment of the present invention, $R^5$ is selected from: hydrogen, —$C_{1-6}$alkyl, —$CH_2CO_2H$, and —$CH_2CO_2C_{1-6}$alkyl. In another embodiment of the present invention, $R^5$ is selected from: hydrogen, —$CH_2CO_2H$, and —$CH_2CO_2C_{1-6}$alkyl. In another embodiment of the present invention, $R^5$ is selected from: hydrogen, and —$C_{1-6}$alkyl. In another embodiment of the present invention, $R^5$ is —$C_{1-6}$alkyl. In another embodiment of the present invention, $R^5$ is hydrogen.

In another embodiment of the present invention, each $R^a$ is independently selected from the group consisting of: halogen, oxo, —$(CH_2)_mOH$, —$(CH_2)_mN(R^j)_2$, —$(CH_2)_mNO_2$, —$(CH_2)_mCN$, —$C_{1-6}$alkyl, —$(CH_2)_mCF_3$, —$(CH_2)_mOCF_3$, —$OCH_2OC_{1-6}$alkyl, —$OCH_2$-aryl, —$(CH_2)_mC(=N—OH)N(R^j)_2$, —$(CH_2)_mOC_{1-6}$alkyl, —$(CH_2)_m$-O-aryl, —$(CH_2)_mSC_{1-6}$alkyl, —$(CH_2)_mS(O)C_{1-6}$alkyl, —$(CH_2)_mS(O)_2C_{1-6}$alkyl, —$(CH_2)_mNHS(O)_2C_{1-6}$alkyl, —$(CH_2)_mC(O)R^f$, —$(CH_2)_mC(O)N(R^j)_2$, —$(CH_2)_mN(R^j)C(O)R^f$, —$(CH_2)_mN(R^j)C(O)N(R^j)_2$, —$(CH_2)_mCO_2H$, —$(CH_2)_mOC(O)H$, —$(CH_2)_mCO_2R^f$, —$(CH_2)_mOC(O)R^f$, —$(CH_2)_mC_{3-7}$cycloalkyl, —$(CH_2)_mC_{3-7}$cycloalkenyl, —$(CH_2)_mC_{2-6}$cycloheteroalkyl, —$(CH_2)_mC_{2-6}$cycloheteroalkenyl, —$(CH_2)_m$aryl, and —$(CH_2)_m$heteroaryl, wherein each $CH_2$ is unsubstituted or substituted with 1 or 2 substituents selected from: oxo, —$(CH_2)_{0-3}OH$, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, phenyl, $CH_2$phenyl, heteroaryl and $CH_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —$(CH_2)_{0-3}OH$, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, phenyl, $CH_2$phenyl, heteroaryl and $CH_2$heteroaryl. In a class of this embodiment, each $CH_2$ is unsubstituted or substituted with 1 or 2 substituents selected from: oxo, —$(CH_2)_{0-3}OH$, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl, and each alkyl, cycloalkyl, cycloalkenyl, cycloheteroalkyl, cycloheteroalkenyl, aryl and heteroaryl is unsubstituted or substituted with 1, 2, 3 or 4 substituents selected from: oxo, —$(CH_2)_{0-3}OH$, —CN, —$NH_2$, —$NH(C_{1-6}alkyl)$, —$N(C_{1-6}alkyl)_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl. In a subclass of this class, each $CH_2$ is unsubstituted or substituted with 1 or 2 substituents selected from: oxo, —$(CH_2)_{0-3}OH$, —$C_{1-6}$alkyl and halogen, and each alkyl, cycloalkyl, cycloalkenyl, cycloheteroalkyl, cycloheteroalkenyl, aryl and heteroaryl is unsubstituted or substituted with 1, 2, or 3 substituents selected from: oxo, —$(CH_2)_{0-3}OH$, —$C_{1-6}$alkyl and halogen.

In another embodiment of the present invention, each $R^a$ is independently selected from the group consisting of: halogen, oxo, —$(CH_2)_mOH$, —$N(R^j)_2$, —$NO_2$, —CN, —$C_{1-6}$alkyl, —$CF_3$, —$OCF_3$, —$OCH_2OC_{1-6}$alkyl, —$OCH_2$-aryl, —$C(=N—OH)N(R^j)_2$, —$OC_{1-6}$alkyl, —O-aryl, —$SC_{1-6}$alkyl, —$S(O)C_{1-6}$alkyl, —$S(O)_2C_{1-6}$alkyl, —$NHS(O)_2C_{1-6}$ alkyl, —C(O)R$^f$, —C(O)N(R$^j$)$_2$, —(CH$_2$)$_m$N(R$^j$)C(O)R$^f$, —N(R$^j$)C(O)N(R$^j$)$_2$, —CO$_2$H, —OC(O)H, —CO$_2$R$^f$, —OC(O)R$^f$, —C$_{3-7}$cycloalkyl, —C$_{3-7}$cycloalkenyl, —C$_{2-6}$cycloheteroalkyl, —C$_{2-6}$cycloheteroalkenyl, aryl and heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl. In a class of this embodiment, each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl, and each alkyl, cycloalkyl, cycloalkenyl, cycloheteroalkyl, cycloheteroalkenyl, aryl and heteroaryl is unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In a subclass of this class, each CH$_2$ is unsubstituted or substituted with 1 or 2 substituents selected from: oxo, —(CH$_2$)$_{0-3}$OH, —C$_{1-6}$alkyl and halogen, and each alkyl, cycloalkyl, cycloalkenyl, cycloheteroalkyl, cycloheteroalkenyl, aryl and heteroaryl is unsubstituted or substituted with 1, 2, or 3 substituents selected from: oxo, —(CH$_2$)$_{0-3}$OH, —C$_{1-6}$alkyl and halogen. In another class of this embodiment, each R$^a$ is independently selected from the group consisting of: halogen, —(CH$_2$)$_m$OH, —N(R$^j$)$_2$, —NO$_2$, —CN, —C$_{1-6}$alkyl, —CF$_3$, —OCH$_2$-phenyl, —OC$_{1-6}$alkyl, —SC$_{1-6}$ alkyl, —S(O)C$_{1-6}$alkyl, —S(O)$_2$C$_{1-6}$alkyl, —NHS(O)$_2$C$_{1-6}$ alkyl, —C(O)NHC$_{1-6}$alkyl, —C(O)N(C$_{1-6}$alkyl)$_2$, —(CH$_2$)$_m$ N(R$^j$)C(O)C$_{1-6}$alkyl, —N(R$^j$)C(O)phenyl, —N(R$^j$)C(O)NHC$_{1-6}$alkyl, —CO$_2$H, —C$_{2-6}$cycloheteroalkyl, phenyl, and heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$ alkyl, —OC$_{1-6}$alkyl, halogen, —CH$_2$F, —CHF$_2$, —CF$_3$, —CO$_2$H, and —CO$_2$C$_{1-6}$alkyl, and wherein alkyl, cycloheteroalkyl, phenyl, and heteroaryl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In a subclass of this class, each CH$_2$ is unsubstituted or substituted with 1 or 2 substituents selected from: oxo, —(CH$_2$)$_{0-3}$OH, —C$_{1-6}$alkyl and halogen, and each alkyl, cycloheteroalkyl, phenyl, and heteroaryl is unsubstituted or substituted with 1, 2, or 3 substituents selected from: oxo, —(CH$_2$)$_{0-3}$OH, —C$_{1-6}$alkyl and halogen. In another subclass of this class, each R$^a$ is independently selected from the group consisting of: F, Cl, Br, —OH, —CH$_2$OH, —NH$_2$, —NO$_2$, —CN, methyl, ethyl, isobutyl, —CF$_3$, —OCH$_2$-phenyl, —OCH$_3$, —SCH$_3$, —S(O)CH$_3$, —SO$_2$CH$_3$, —NHSO$_2$CH$_3$, —C(O)N(CH$_3$)$_2$, —C(O)NHCH$_3$, —NHC(O)CF$_{13}$, —CH$_2$NHC(O)CH$_3$, —NHC(O)phenyl, —NHC(O)NHCH$_2$CH$_3$, —CO$_2$H, piperidine, morpholine, phenyl, and pyrazole, pyrazine, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl, and wherein alkyl, cycloheteroalkyl, phenyl, and heteroaryl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In a subclass of this subclass, each CH$_2$ is unsubstituted or substituted with 1 or 2 substituents selected from: oxo, —(CH$_2$)$_{0-3}$OH, —C$_{1-6}$alkyl and halogen, and each alkyl, cycloheteroalkyl, phenyl, and heteroaryl is unsubstituted or substituted with 1, 2 or 3 substituents selected from: oxo, —(CH$_2$)$_{0-3}$OH, —C$_{1-6}$alkyl and halogen.

In another embodiment of the present invention, each R$^a$ is independently selected from the group consisting of: —(CH$_2$)$_m$CF$_3$, —(CH$_2$)$_m$OCF$_3$, —OCH$_2$OC$_{1-6}$alkyl, —OCH$_2$-aryl, —(CH$_2$)$_m$C(=N—OH)N(R$^j$)$_2$, —(CH$_2$)$_m$OC$_{1-6}$alkyl, —(CH$_2$)$_m$—O-aryl, —(CH$_2$)$_m$SC$_{1-6}$alkyl, —(CH$_2$)$_m$S(O)C$_{1-6}$alkyl, —(CH$_2$)$_m$S(O)$_2$C$_{1-6}$alkyl, —(CH$_2$)$_m$ NHS(O)$_2$C$_{1-6}$alkyl, —(CH$_2$)$_m$C(O)R$^f$, —(CH$_2$)$_m$C(O)N(R$^j$)$_2$, —(CH$_2$)$_m$N(R$^j$)C(O)R$^f$, —(CH$_2$)$_m$N(R$^j$)C(O)N(R$^j$)$_2$, —(CH$_2$)$_m$CO$_2$H, —(CH$_2$)$_m$C$_{3-7}$cycloalkyl, —(CH$_2$)$_m$C$_{3-7}$ cycloalkenyl, —(CH$_2$)$_m$C$_{2-6}$cycloheteroalkyl, —(CH$_2$)$_m$ C$_{2-6}$ cycloheteroalkenyl, —(CH$_2$)$_m$aryl, and —(CH$_2$)$_m$heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In a class of this embodiment, each CH$_2$ is unsubstituted or substituted with 1 or 2 substituents selected from: oxo, —(CH$_2$)$_{0-3}$OH, —C$_{1-6}$alkyl and halogen, and each alkyl, cycloalkyl, cycloalkenyl, cycloheteroalkyl, cycloheteroalkenyl, aryl and heteroaryl is unsubstituted or substituted with 1, 2, or 3 substituents selected from: oxo, —(CH$_2$)$_{0-3}$OH, —C$_{1-6}$alkyl and halogen. In another class of this embodiment, each R$^a$ is independently selected from the group consisting of: —CF$_3$, —OCH$_2$-phenyl, —OC$_{1-6}$alkyl, —SC$_{1-6}$alkyl, —S(O)C$_{1-6}$ alkyl, —S(O)$_2$C$_{1-6}$alkyl, —NHS(O)$_2$C$_{1-6}$alkyl, —C(O)NHC$_{1-6}$alkyl, —C(O)N(C$_{1-6}$alkyl)$_2$, —CH$_2$N(R$^j$)C(O)C$_{1-6}$alkyl, —N(R$^j$)C(O)phenyl, —N(R$^j$)C(O)NHC$_{1-6}$alkyl, —CO$_2$H, —C$_{2-6}$cycloheteroalkyl, phenyl, heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl, and wherein alkyl, cycloheteroalkyl, phenyl and heteroaryl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In a subclass of this class, each CH$_2$ is unsubstituted or substituted with 1 or 2 substituents selected from: oxo, —(CH$_2$)$_{0-3}$OH, —C$_{1-6}$alkyl and halogen, and each alkyl, cycloheteroalkyl, phenyl, and heteroaryl is unsubstituted or substituted with 1, 2, or 3 substituents selected from: oxo, —(CH$_2$)$_{0-3}$OH, —C$_{1-6}$alkyl and halogen. In another subclass of this class, each R$^a$ is independently selected from the group consisting of: —CF$_3$, —OCH$_2$-phenyl, —OCH$_3$, —SCH$_3$, —S(O)CH$_3$, —SO$_2$CH$_3$, —NHSO$_2$CH$_3$, —C(O)N(CH$_3$)$_2$, —C(O)

NHCH$_3$, —NHC(O)CH$_3$, —CH$_2$NHC(O)CH$_3$, —NHC(O) phenyl, —NHC(O)NHCH$_2$CH$_3$, —CO$_2$H, piperidine, morpholine, phenyl, pyrazole, pyrazine, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$ alkyl, halogen, —CH$_2$F, —CHF$_2$, —CF$_3$, —CO$_2$H, and —CO$_2$C$_{1-6}$alkyl, and wherein alkyl, cycloheteroalkyl, phenyl, and heteroaryl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$ alkyl. In a subclass of this subclass, each CH$_2$ is unsubstituted or substituted with 1 or 2 substituents selected from: oxo, —(CH$_2$)$_{0-3}$OH, —C$_{1-6}$alkyl and halogen, and each alkyl, cycloheteroalkyl, phenyl, and heteroaryl is unsubstituted or substituted with 1, 2, or 3 substituents selected from: oxo, —(CH$_2$)$_{0-3}$OH, —C$_{1-6}$alkyl and halogen.

In another embodiment of the present invention, each R$^a$ is independently selected from the group consisting of —(CH$_2$)$_m$ CF$_3$, —OCH$_2$-aryl, —(CH$_2$)$_m$OC$_{1-6}$alkyl, —(CH$_2$)$_m$SC$_{1-6}$ alkyl, —(CH$_2$)$_m$S(O)C$_{1-6}$alkyl, —(CH$_2$)$_m$S(O)$_2$C$_{1-6}$alkyl, —(CH$_2$)$_m$NHS(O)$_2$C$_{1-6}$alkyl, —(CH$_2$)$_m$C(O)N(R$^j$)$_2$, —(CH$_2$)$_m$N(R$^j$)C(O)R$^f$, —(CH$_2$)$_m$N(R$^j$)C(O)N(R$^j$)$_2$, —(CH$_2$)$_m$C$_{2-6}$cycloheteroalkyl, —(CH$_2$)$_m$aryl, and —(CH$_2$)$_m$ heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$ alkyl, —OC$_{1-6}$alkyl, halogen, —CH$_2$F, —CHF$_2$, —CF$_3$, —CO$_2$H, and —CO$_2$C$_{1-6}$alkyl, and wherein alkyl, cycloheteroalkyl, aryl and heteroaryl are unsubstituted or substituted with 1, 2, 3 or 4 substituents selected from: oxo, —(CH$_2$)$_{0-3}$ OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In a class of this embodiment, each CH$_2$ is unsubstituted or substituted with 1 or 2 substituents selected from: oxo, —(CH$_2$)$_{0-3}$OH, —C$_{1-6}$ alkyl and halogen, and each alkyl, cycloheteroalkyl, aryl and heteroaryl is unsubstituted or substituted with 1, 2, or 3 substituents selected from: oxo, —(CH$_2$)$_{0-3}$OH, —C$_{1-6}$ alkyl and halogen. In another class of this embodiment, each R$^a$ is independently selected from the group consisting of: —CF$_3$, —OCH$_2$-phenyl, —OC$_{1-6}$alkyl, —SC$_{1-6}$alkyl, —S(O)C$_{1-6}$ alkyl, —S(O)$_2$C$_{1-6}$alkyl, —NHS(O)$_2$C$_{1-6}$alkyl, —C(O)NHC$_{1-6}$alkyl, —C(O)N(C$_{1-6}$alkyl)$_2$, —(CH$_2$)$_m$N(R$^j$)C(O)C$_{1-6}$alkyl, —N(R$^j$)C(O)phenyl, —N(R$^j$)C(O)NHC$_{1-6}$alkyl, —C$_{2-6}$cycloheteroalkyl, -phenyl, -heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$ alkyl, halogen, —CH$_2$F, —CHF$_2$, —CF$_3$, —CO$_2$H, and —CO$_2$C$_{1-6}$ alkyl, and wherein alkyl, cycloheteroalkyl, c phenyl and heteroaryl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In a subclass of this class, each CH$_2$ is unsubstituted or substituted with 1 or 2 substituents selected from: oxo, —(CH$_2$)$_{0-3}$OH, —C$_{1-6}$alkyl and halogen, and each alkyl, cycloheteroalkyl, phenyl, and heteroaryl is unsubstituted or substituted with 1, 2, or 3 substituents selected from: oxo, —(CH$_2$)$_{0-3}$OH, —C$_{1-6}$alkyl and halogen. In another subclass of this class, each R$^a$ is independently selected from the group consisting of: —CF$_3$, —OCH$_2$-phenyl, —OCH$_3$, —SCH$_3$, —S(O)CH$_3$, —SO$_2$CH$_3$, —NHSO$_2$CH$_3$, —C(O)N(CH$_3$)$_2$, —C(O)NHCH$_3$, —NHC(O)CH$_3$, —CH$_2$NHC(O)CH$_3$, —NHC(O)phenyl, —NHC(O)NHCH$_2$CH$_3$, piperidine, morpholine, phenyl, pyrazole, pyrazine, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$ alkyl, —OC$_{1-6}$alkyl, halogen, —CH$_2$F, —CHF$_2$, —CF$_3$, —CO$_2$H, and —CO$_2$C$_{1-6}$alkyl, and wherein alkyl, cycloheteroalkyl, phenyl, and heteroaryl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In a subclass of this subclass, each CH$_2$ is unsubstituted or substituted with 1 or 2 substituents selected from: oxo, —(CH$_2$)$_{0-3}$OH, —C$_{1-6}$alkyl and halogen, and each alkyl, cycloheteroalkyl, phenyl, and heteroaryl are unsubstituted or substituted with 1, 2, or 3 substituents selected from: oxo, —(CH$_2$)$_{0-3}$OH, —C$_{1-6}$ alkyl and halogen.

In another embodiment of the present invention, each R$^a$ is independently selected from the group consisting of halogen, —(CH$_2$)$_m$OH, —N(R$^j$)$_2$, —NO$_2$, —CN, —C$_{1-6}$alkyl, —CF$_3$, —OCH$_2$-aryl, —O-aryl, —OC$_{1-6}$alkyl, —SC$_{1-6}$alkyl, —S(O)C$_{1-6}$alkyl, —S(O)$_2$C$_{1-6}$alkyl, —NHS(O)$_2$C$_{1-6}$alkyl, —C(O)N(R$^j$)$_2$, —(CH$_2$)$_m$N(R$^j$)C(O)R$^f$, —N(R$^j$)C(O)N(R$^j$)$_2$, —CO$_2$H, —C$_{2-6}$cycloheteroalkyl, aryl, and heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, and wherein alkyl, cycloheteroalkyl, aryl and heteroaryl are unsubstituted or substituted with 1, 2 or 3 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl. In a class of this embodiment, each CH$_2$ is unsubstituted or substituted with 1 or 2 substituents selected from: oxo, —(CH$_2$)$_{0-3}$OH, and —C$_{1-6}$alkyl, and each alkyl, cycloheteroalkyl, aryl and heteroaryl is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, and halogen. In another class of this embodiment, each CH$_2$ is unsubstituted, and each alkyl, cycloheteroalkyl, aryl and heteroaryl are unsubstituted or substituted with 1 or 2 substituents selected from: —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, and halogen. In another class of this embodiment, each R$^a$ is independently selected from the group consisting of halogen, —(CH$_2$)$_m$OH, —N(R$^j$)$_2$, —NO$_2$, —CN, —C$_{1-6}$alkyl, —CF$_3$, —OCH$_2$-phenyl, —O-phenyl, —OC$_{1-6}$alkyl, —SC$_{1-6}$alkyl, —S(O)C$_{1-6}$alkyl, —S(O)$_2$C$_{1-6}$alkyl, —NHS(O)$_2$C$_{1-6}$alkyl, —C(O)NHC$_{1-6}$alkyl, —C(O)N(C$_{1-6}$alkyl)$_2$, —(CH$_2$)$_m$N(R$^j$)C(O)C$_{1-6}$alkyl, —N(R$^j$)C(O)phenyl, —N(R$^j$)C(O)NHC$_{1-6}$alkyl, —CO$_2$H, —C$_{2-6}$cycloheteroalkyl, phenyl, and heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$ alkyl, halogen, —CH$_2$F, —CHF$_2$, —CF$_3$, —CO$_2$H, —CO$_2$C$_{1-6}$alkyl, and wherein alkyl, cycloheteroalkyl, phenyl and heteroaryl are unsubstituted or substituted with 1, 2 or 3 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl. In a class of this embodiment, each CH$_2$ is unsubstituted or substituted with 1 or 2 substituents selected from: oxo, —(CH$_2$)$_{0-3}$OH, and —C$_{1-6}$alkyl, and each alkyl, cycloheteroalkyl, phenyl and heteroaryl is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, and halogen. In another class of this embodiment, each CH$_2$ is unsubstituted, and each alkyl, cycloheteroalkyl, phenyl and heteroaryl is unsubstituted or substituted with 1 or 2 substituents selected from: —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, and halogen. In another class of this embodiment, each R$^a$ is independently selected from the group consisting of: F, Cl, Br, —OH, —CH$_2$OH, —NH$_2$, —NO$_2$, —CN, -methyl, ethyl, isobutyl, —CF$_3$, —OCH$_2$-phenyl, —O-phenyl, —OCH$_3$, —SCH$_3$, —S(O)CH$_3$, —SO$_2$CH$_3$, —NHSO$_2$CH$_3$, —C(O)N(CH$_3$)$_2$, —C(O)NHCH$_3$, —NHC(O)CH$_3$, —CH$_2$NHC(O)CH$_3$, —NHC(O)phenyl, —NHC(O)NHCH$_2$CH$_3$, —CO$_2$H, piperidine, morpholine, phenyl, pyrazole, and pyrazine, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, and wherein alkyl, cycloheteroalkyl, phenyl and heteroaryl are unsubstituted or substituted with 1, 2 or 3 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl. In a subclass of this class, each CH$_2$ is unsubstituted or substituted with 1 or 2 substituents selected from: oxo, —(CH$_2$)$_{0-3}$OH, and —C$_{1-6}$alkyl, and each alkyl, cycloheteroalkyl, phenyl and heteroaryl is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, and halogen. In another subclass of this class, each CH$_2$ is unsubstituted, and each alkyl, cycloheteroalkyl, phenyl and heteroaryl is unsubstituted or substituted with 1 or 2 substituents selected from: —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, and halogen.

In another embodiment of the present invention, each R$^a$ is independently selected from the group consisting of: F, Cl, —OH, —CH$_2$OH, —NH$_2$, —CN, -methyl, isobutyl, —OCH$_2$-phenyl, O-phenyl, —OCH$_3$, —SO$_2$CH$_3$, —NHSO$_2$CH$_3$, —C(O)N(CH$_3$)$_2$, —C(O)NHCH$_3$, —NHC(O)CH$_3$, —CH$_2$NHC(O)CH$_3$, phenyl, and pyrazole, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, and wherein alkyl, cycloheteroalkyl, phenyl and heteroaryl are unsubstituted or substituted with 1, 2 or 3 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl. In a class of this embodiment, each CH$_2$ is unsubstituted or substituted with 1 or 2 substituents selected from: oxo, —(CH$_2$)$_{0-3}$OH, and —C$_{1-6}$alkyl, and each alkyl, cycloheteroalkyl, phenyl and heteroaryl is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, and halogen. In another class of this embodiment, each CH$_2$ is unsubstituted, and each alkyl, cycloheteroalkyl, phenyl and heteroaryl is unsubstituted or substituted with 1 or 2 substituents selected from: —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, and halogen.

In another embodiment of the present invention, each R$^a$ is independently selected from the group consisting of: —(CH$_2$)$_m$OH, —(CH$_2$)$_m$aryl, and —(CH$_2$)$_m$heteroaryl, wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl, and wherein aryl and heteroaryl are unsubstituted or substituted with 1, 2 or 3 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In a class of this embodiment, each CH$_2$ is unsubstituted or substituted with 1 or 2 substituents selected from: oxo, —(CH$_2$)$_{0-3}$OH, and —C$_{1-6}$alkyl, and each aryl and heteroaryl is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, and halogen. In another class of this embodiment, each CH$_2$ is unsubstituted, and each aryl and heteroaryl is unsubstituted or substituted with 1 or 2 substituents selected from: —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, and halogen. In another class of this embodiment, each R$^a$ is independently selected from the group consisting of: —CH$_2$OH, phenyl, and pyrazole, wherein each phenyl and heteroaryl is unsubstituted or substituted with 1, 2 or 3 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In a class of this embodiment, each phenyl and heteroaryl is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, and halogen. In another class of this embodiment, phenyl and heteroaryl is unsubstituted or substituted with 1 or 2 substituents selected from: —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, and halogen.

In another embodiment of the present invention, each R$^a$ is independently selected from the group consisting of: —(CH$_2$)$_m$OH, —C$_{1-6}$alkyl, phenyl, and heteroaryl, wherein each alkyl, phenyl and heteroaryl is unsubstituted or substituted with 1, 2 or 3 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl. In a class of this embodiment, each alkyl, phenyl and heteroaryl is unsubstituted or substituted with 1 or 2 substituents selected from: —OH, —C$_{1-6}$alkyl and halogen. In another class of this embodiment, each alkyl, phenyl and heteroaryl is unsubstituted or substituted with 1 or 2 substituents selected from: —OH. In another class of this embodiment, each R$^a$ is independently selected from the group consisting of: —OH, —CH$_2$OH, methyl, phenyl, and pyrazole, wherein each alkyl, phenyl and heteroaryl is unsubstituted or substituted with 1, 2 or 3 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl. In a class of this embodiment, each alkyl, phenyl and heteroaryl is unsubstituted or substituted with 1 or 2 substituents selected from: —OH, —C$_{1-6}$alkyl and halogen. In another class of this embodiment, each alkyl, phenyl and heteroaryl is unsubstituted or substituted with 1 or 2 substituents selected from: —OH.

In another embodiment of the present invention, each R$^b$ is independently selected from: hydrogen, —C$_{1-6}$alkyl, halogen, —OH, —NO$_2$, —NH$_2$, —NH(C$_{1-6}$alkyl), —N(C$_{1-6}$alkyl)$_2$, —OC$_{1-6}$alkyl, —(CH$_2$)$_q$CO$_2$H, —(CH$_2$)$_q$CO$_2$C$_{1-6}$alkyl, —CF$_3$, —CN, —SO$_2$C$_{1-6}$alkyl, and —(CH$_2$)$_q$CON(R$^e$)$_2$, wherein each CH$_2$ is unsubstituted or substituted with 1 or 2 halogens, and wherein each alkyl is unsubstituted or substituted with 1, 2 or 3 halogens. In a class of this embodiment, each $R^b$ is independently selected from: hydrogen, —$C_{1-6}$alkyl, halogen, —OH, —$NO_2$, —$NH_2$, —NH($C_{1-6}$alkyl), —N($C_{1-6}$alkyl)$_2$, —O$C_{1-6}$alkyl, —$(CH_2)_qCO_2H$, —$(CH_2)_qCO_2C_{1-6}$alkyl, —$CF_3$, —CN, —$SO_2C_{1-6}$alkyl, and —$(CH_2)_qCON(R^e)_2$. In another embodiment of the present invention, each $R^b$ is independently selected from: hydrogen, —$C_{1-6}$alkyl, halogen, —OH, —$NO_2$, —$NH_2$, —NH($C_{1-6}$alkyl), —N($C_{1-6}$alkyl)$_2$, —O$C_{1-6}$alkyl, —$CO_2H$, —$CO_2C_{1-6}$alkyl, —$CF_3$, —CN, —$SO_2C_{1-6}$alkyl, and —CON($R^e$)$_2$, wherein each $CH_2$ is unsubstituted or substituted with 1 or 2 halogens, and wherein each alkyl is unsubstituted or substituted with 1, 2 or 3 halogens. In a class of this embodiment, each $R^b$ is independently selected from: hydrogen, —$C_{1-6}$alkyl, halogen, —OH, —$NO_2$, —$NH_2$, —NH($C_{1-6}$alkyl), —N($C_{1-6}$alkyl)$_2$, —O$C_{1-6}$alkyl, —$CO_2H$, —$CO_2C_{1-6}$alkyl, —$CF_3$, —CN, —$SO_2C_{1-6}$alkyl, and —CON($R^e$)$_2$. In another embodiment of the present invention, each $R^b$ is independently selected from: hydrogen, —$C_{1-6}$alkyl, halogen, —OH, —$NO_2$, —$NH_2$, —NH($C_{1-6}$alkyl), —N($C_{1-6}$alkyl)$_2$, —O$C_{1-6}$alkyl, —$CF_3$, —CN, —$SO_2C_{1-6}$alkyl, and —$(CH_2)_qCON(R^e)_2$, wherein each $CH_2$ is unsubstituted or substituted with 1 or 2 halogens, and wherein each alkyl is unsubstituted or substituted with 1, 2 or 3 halogens. In a class of this embodiment, each $R^b$ is independently selected from: hydrogen, —$C_{1-6}$alkyl, halogen, —OH, —$NO_2$, —$NH_2$, —NH($C_{1-6}$alkyl), —N($C_{1-6}$alkyl)$_2$, —O$C_{1-6}$alkyl, —$CF_3$, —CN, —$SO_2C_{1-6}$alkyl, and —$(CH_2)_qCON(R^e)_2$. In another embodiment of the present invention, each $R^b$ is independently selected from: hydrogen, —$C_{1-6}$alkyl, halogen, —OH, —$NO_2$, —$NH_2$, —NH($C_{1-6}$alkyl), —N($C_{1-6}$alkyl)$_2$, —O$C_{1-6}$alkyl, —$CF_3$, and —CN, wherein each $CH_2$ is unsubstituted or substituted with 1 or 2 halogens, and wherein each alkyl is unsubstituted or substituted with 1, 2 or 3 halogens. In a class of this embodiment, each $R^b$ is independently selected from: hydrogen, —$C_{1-6}$alkyl, halogen, —OH, —$NO_2$, —$NH_2$, —NH($C_{1-6}$alkyl), —N($C_{1-6}$alkyl)$_2$, —O$C_{1-6}$alkyl, —$CF_3$, and —CN. In another embodiment of the present invention, each $R^b$ is independently selected from: hydrogen, and —$C_{1-6}$alkyl, wherein each alkyl is unsubstituted or substituted with 1, 2 or 3 halogens. In a class of this embodiment, each $R^b$ is independently selected from: hydrogen, and —$C_{1-6}$alkyl. In another class of this embodiment, each $R^b$ is independently selected from: hydrogen, and methyl. In another class of this embodiment, each $R^b$ is hydrogen. In another class of this embodiment, each $R^b$ is methyl.

In another embodiment of the present invention, each $R^c$ is independently selected from: halogen, oxo, —$(CH_2)_r$OH, —$(CH_2)_rN(R^e)_2$, —$(CH_2)_r$CN, —$C_{1-6}$alkyl, —$CF_3$, —$C_{1-6}$alkyl-OH, —OCH$_2$O$C_{1-6}$alkyl, —$(CH_2)_r$O$C_{1-6}$alkyl, —OCH$_2$aryl, —$(CH_2)_r$S$C_{1-6}$alkyl, —$(CH_2)_r$C(O)R$^f$, —$(CH_2)_r$C(O)N(R$^e$)$_2$, —$(CH_2)_r$CO$_2$H, —$(CH_2)_r$CO$_2$R$^f$, —$(CH_2)_r$C$_{3-7}$cycloalkyl, —$(CH_2)_r$C$_{2-6}$cycloheteroalkyl, —$(CH_2)_r$aryl, and —$(CH_2)_r$heteroaryl, wherein each $CH_2$ is unsubstituted or substituted with 1 or 2 substituents selected from: oxo, —OH, —CN, —N(R$^h$)$_2$, —$C_{1-6}$alkyl, —O$C_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —$C_{1-6}$alkyl, —O$C_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl. In another embodiment of the present invention, each $R^c$ is independently selected from: halogen, oxo, —$(CH_2)_r$OH, —$(CH_2)_rN(R^e)_2$, —$(CH_2)_r$CN, —$C_{1-6}$alkyl, —$CF_3$, —$C_{1-6}$alkyl-OH, —OCH$_2$O$C_{1-6}$alkyl, —$(CH_2)_r$O$C_{1-6}$alkyl, —OCH$_2$aryl, —$(CH_2)_r$S$C_{1-6}$alkyl, —$(CH_2)_r$C(O)R$^f$, —$(CH_2)_r$C(O)N(R$^e$)$_2$, —$(CH_2)_r$C$_{3-7}$cycloalkyl, —$(CH_2)_r$C$_{2-6}$cycloheteroalkyl, —$(CH_2)_r$aryl, and —$(CH_2)_r$heteroaryl, wherein each $CH_2$ is unsubstituted or substituted with 1 or 2 substituents selected from: oxo, —OH, —CN, —N(R$^h$)$_2$, —$C_{1-6}$alkyl, —$C_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2 or 3 substituents selected from: oxo, —OH, —CN, —N(R$^h$)$_2$, —$C_{1-6}$alkyl, —O$C_{1-6}$alkyl, halogen, —CH$_2$F, —CHF$_2$, —CF$_3$, —CO$_2$H, and —CO$_2$C$_{1-6}$alkyl. In another embodiment of the present invention, each $R^c$ is independently selected from: halogen, oxo, —$(CH_2)_r$OH, —$(CH_2)_rN(R^e)_2$, —$(CH_2)_r$CN, —$C_{1-6}$alkyl, —$CF_3$, —$C_{1-6}$alkyl-OH, —OCH$_2$O$C_{1-6}$alkyl, —$(CH_2)_r$O$C_{1-6}$alkyl, —OCH$_2$aryl, —$(CH_2)_r$S$C_{1-6}$alkyl, —$(CH_2)_r$C(O)R$^f$, and —$(CH_2)_r$C(O)N(R$^e$)$_2$, wherein each $CH_2$ is unsubstituted or substituted with 1 or 2 substituents selected from: oxo, —OH, —CN, —N(R$^h$)$_2$, —$C_{1-6}$alkyl, —O$C_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl and aryl are unsubstituted or substituted with 1, 2 or 3 substituents selected from: oxo, —OH, —CN, —N(R$^h$)$_2$, —$C_{1-6}$alkyl, —O$C_{1-6}$alkyl, halogen, —CH$_2$F, —CHF$_2$, —CF$_3$, —CO$_2$H, —CO$_2$C$_{1-6}$alkyl, and —C$_{3-7}$cycloalkyl. In class of this embodiment, each $R^c$ is independently selected from: halogen, oxo, —OH, —N(R$^e$)$_2$, —CN, —$C_{1-6}$alkyl, —$CF_3$, —$C_{1-6}$alkyl-OH, —OCH$_2$O$C_{1-6}$alkyl, —O$C_{1-6}$alkyl, —S$C_{1-6}$alkyl, —C(O)R$^f$, and —C(O)N(R$^e$)$_2$, wherein alkyl is unsubstituted or substituted with 1, 2 or 3 substituents selected from: oxo, —OH, —CN, —N(R$^h$)$_2$, —$C_{1-6}$alkyl, —O$C_{1-6}$alkyl, halogen, —CH$_2$F, —CHF$_2$, —CF$_3$, —CO$_2$H, and —CO$_2$C$_{1-6}$alkyl.

In another embodiment of the present invention, each $R^c$ is independently selected from: halogen, oxo, —$(CH_2)_r$OH, —$(CH_2)_rN(R^e)_2$, —$(CH_2)_r$CN, —$C_{1-6}$alkyl, —$CF_3$, —$C_{1-6}$alkyl-OH, —OCH$_2$O$C_{1-6}$alkyl, —$(CH_2)_r$O$C_{1-6}$alkyl, —OCH$_2$aryl, —$(CH_2)_r$S$C_{1-6}$alkyl, —$(CH_2)_r$C(O)R$^f$, —$(CH_2)_r$C(O)N(R$^e$)$_2$, —$(CH_2)_r$CO$_2$H, —$(CH_2)_r$CO$_2$R$^f$, —$(CH_2)_r$C$_{3-7}$cycloalkyl, —$(CH_2)_r$C$_{2-6}$cycloheteroalkyl, —$(CH_2)_r$aryl, and —$(CH_2)_r$heteroaryl. In a class of this embodiment of the present invention, each $R^c$ is independently selected from: halogen, oxo, —$(CH_2)_r$OH, —$(CH_2)_r$N(R$^e$)$_2$, —$(CH_2)_r$CN, —$C_{1-6}$alkyl, —$CF_3$, —$C_{1-6}$alkyl-OH, —OCH$_2$O$C_{1-6}$alkyl, —$(CH_2)_r$O$C_{1-6}$alkyl, —OCH$_2$aryl, —$(CH_2)_r$S$C_{1-6}$alkyl, —$(CH_2)_r$C(O)R$^f$, —$(CH_2)_r$C(O)N(R$^e$)$_2$, —$(CH_2)_r$C$_{3-7}$cycloalkyl, —$(CH_2)_r$C$_{2-6}$cycloheteroalkyl, —$(CH_2)_r$aryl, and —$(CH_2)_r$heteroaryl. In another class of this embodiment, each $R^c$ is independently selected from: halogen, oxo, —$(CH_2)_r$OH, —$(CH_2)_r$N(R$^e$)$_2$, —$(CH_2)_r$CN, —$C_{1-6}$alkyl, —$CF_3$, —$C_{1-6}$alkyl-OH, —OCH$_2$O$C_{1-6}$alkyl, —$(CH_2)_r$O$C_{1-6}$alkyl, —OCH$_2$aryl, —$(CH_2)_r$S$C_{1-6}$alkyl, —$(CH_2)_r$C(O)R$^f$, and —$(CH_2)_r$C(O)N(R$^e$)$_2$. In another class of this embodiment, each $R^c$ is independently selected from: halogen, oxo, —$(CH_2)_r$OH, —$(CH_2)_r$N(R$^e$)$_2$, —$(CH_2)_r$CN, —$C_{1-6}$alkyl, —$CF_3$, —$C_{1-6}$alkyl-OH, —$(CH_2)_r$O$C_{1-6}$alkyl, —$(CH_2)_r$S$C_{1-6}$alkyl, —$(CH_2)_r$C(O)R$^f$, and —$(CH_2)_r$C(O)N(R$^e$)$_2$. In another class of this embodiment, each $R^c$ is independently selected from: halogen, oxo, —$(CH_2)_r$OH, —$(CH_2)_r$N(R$^e$)$_2$, —$(CH_2)_r$CN, —$C_{1-6}$alkyl, —$CF_3$, —$C_{1-6}$alkyl-OH, —$(CH_2)_r$O$C_{1-6}$alkyl, and —$(CH_2)_r$S$C_{1-6}$alkyl. In another class of this embodiment, each $R^c$ is independently selected from: halogen, oxo, —$(CH_2)_r$OH, —$(CH_2)_r$N(R$^e$)$_2$, —$(CH_2)_r$CN, —$C_{1-6}$alkyl, and —$CF_3$. In another class of this embodiment, each $R^c$ is independently selected from: halogen, oxo, and —$C_{1-6}$alkyl. In another embodiment of the present invention, each $R^c$ is oxo.

In another embodiment of the present invention, each $R^d$ is independently selected from the group consisting of hydrogen, —$NH_2$, —$NH(C_{1-6}$alkyl), —$N(C_{1-6}$alkyl)$_2$, —$C_{1-6}$alkyl, —$C_{1-6}$alkyl-OH, —$(CH_2)_rC_{3-7}$cycloalkyl, —$(CH_2)_r$$C_{2-6}$cycloheteroalkyl, —$(CH_2)_r$aryl, and —$(CH_2)_r$ heteroaryl, wherein each $CH_2$ is unsubstituted or substituted with 1 or 2 substituents selected from —OH, —$NH_2$, —$C_{1-6}$alkyl, —$OC_{1-6}$alkyl, halogen, —$CO_2H$, and —$CO_2C_{1-6}$alkyl, and wherein alkyl, cycloalkyl, cycloheteroalkyl, aryl and heteroaryl are unsubstituted or substituted with 1, 2, 3 or 4 substituents selected from —OH, —$NH_2$, —$C_{1-6}$alkyl, —$OC_{1-6}$alkyl, halogen, —$CO_2H$, and —$CO_2C_{1-6}$alkyl. In a class of this embodiment, each $R^d$ is independently selected from the group consisting of hydrogen, —$NH_2$, —$NH(C_{1-6}$alkyl), —$N(C_{1-6}$alkyl)$_2$, —$C_{1-6}$alkyl, —$C_{1-6}$alkyl-OH, wherein alkyl is unsubstituted or substituted with 1, 2, 3 or 4 substituents selected from —OH, —$NH_2$, —$C_{1-6}$alkyl, —$OC_{1-6}$alkyl, halogen, —$CO_2H$, and —$CO_2C_{1-6}$alkyl. In another class of this embodiment, each $R^d$ is independently selected from the group consisting of —$NH_2$, —$NH(C_{1-6}$alkyl), —$N(C_{1-6}$alkyl)$_2$, wherein alkyl is unsubstituted or substituted with 1, 2 or 3 substituents selected from —OH, —$NH_2$, —$C_{1-6}$alkyl, —$OC_{1-6}$alkyl, halogen, —$CO_2H$, and —$CO_2C_{1-6}$alkyl. In another class of this embodiment, each $R^d$ is independently selected from the group consisting of: hydrogen, —$C_{1-6}$alkyl, —$C_{1-6}$alkyl-OH, wherein alkyl is unsubstituted or substituted with 1, 2 or 3 substituents selected from —OH, —$NH_2$, —$C_{1-6}$alkyl, —$OC_{1-6}$alkyl, halogen, —$CO_2H$, and —$CO_2C_{1-6}$alkyl.

In another embodiment of the present invention, each $R^e$, $R^g$ and $R^h$ is independently selected from: hydrogen, and $C_{1-6}$alkyl, wherein alkyl is unsubstituted or substituted with 1, 2, 3 or 4 substituents selected from: —OH, oxo, halogen, $C_{1-6}$alkyl, —$OC_{1-6}$alkyl, —$NH_2$, —$NH(C_{1-6}$alkyl), and —$N(C_{1-6}$alkyl)$_2$. In a class of this embodiment, each $R^e$, $R^g$ and $R^h$ is independently selected from: hydrogen, and $C_{1-6}$alkyl. In another class of this embodiment, each $R^e$ is independently selected from: hydrogen, and $C_{1-6}$alkyl, wherein alkyl is unsubstituted or substituted with 1, 2, 3 or 4 substituents selected from: —OH, oxo, halogen, $C_{1-6}$alkyl, —$OC_{1-6}$alkyl, —$NH_2$, —$NH(C_{1-6}$alkyl), and —N($C_{1-6}$alkyl)$_2$. In a class of this embodiment, each $R^e$ is independently selected from: hydrogen, and $C_{1-6}$alkyl. In another class of this embodiment, each $R^g$ is independently selected from: hydrogen, and $C_{1-6}$alkyl, wherein alkyl is unsubstituted or substituted with 1, 2, 3 or 4 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$. In a class of this embodiment, each $R^g$ is independently selected from: hydrogen, and $C_{1-6}$alkyl. In another class of this embodiment, each $R^h$ is independently selected from: hydrogen, and $C_{1-6}$alkyl, wherein alkyl is unsubstituted or substituted with 1, 2, 3 or 4 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$. In a class of this embodiment, each $R^h$ is independently selected from: hydrogen, and $C_{1-6}$alkyl.

In another embodiment of the present invention, each $R^j$ is independently selected from: hydrogen, $C_{1-6}$alkyl, $C_{3-6}$cycloalkyl, —C(O)$R^j$, and —SO$_2R^j$, wherein alkyl and cycloalkyl are unsubstituted or substituted with 1, 2, 3 or 4 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$. In a class of this embodiment, each $R^j$ is independently selected from: hydrogen, —$C_{1-6}$alkyl, —C(O)$R^i$, and —SO$_2R^i$, wherein alkyl is unsubstituted or substituted with 1, 2, 3 or 4 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$. In another class of this embodiment, each $R^j$ is independently selected from: hydrogen, and $C_{1-6}$alkyl, wherein alkyl is unsubstituted or substituted with 1, 2, 3 or 4 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$. In another class of this embodiment, each $R^j$ is independently selected from: hydrogen and $C_{1-6}$alkyl.

In another embodiment of the present invention, each $R^f$ and $R^i$ is independently selected from: $C_{1-6}$alkyl, $C_{4-7}$cycloalkyl, $C_{4-7}$cycloalkenyl, $C_{3-7}$cycloheteroalkyl, $C_{3-7}$cycloheteroalkenyl, aryl, and heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —$C_{1-6}$ alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, and heteroaryl. In a class of this embodiment, each $R^f$ and $R^i$ is independently selected from: $C_{1-6}$alkyl, $C_{4-7}$cycloalkyl, $C_{4-7}$cycloalkenyl, $C_{3-7}$cycloheteroalkyl, $C_{3-7}$cycloheteroalkenyl, aryl, and heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —$C_{1-6}$ alkyl, —$OC_{1-6}$alkyl, halogen, —$CH_2F$, —$CHF_2$, —$CF_3$, —$CO_2H$, and —$CO_2C_{1-6}$alkyl. In a class of this embodiment, each $R^f$ is independently selected from: $C_{1-6}$alkyl, $C_{4-7}$cycloalkyl, $C_{4-7}$cycloalkenyl, $C_{3-7}$cycloheteroalkyl, $C_{3-7}$cycloheteroalkenyl, aryl, and heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —$C_{1-6}$ alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, and heteroaryl. In a subclass of this class, each $R^f$ is independently selected from: $C_{1-6}$alkyl, $C_{4-7}$cycloalkyl, $C_{4-7}$cycloalkenyl, $C_{3-7}$cycloheteroalkyl, $C_{3-7}$cycloheteroalkenyl, aryl, and heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —$C_{1-6}$ alkyl, —$OC_{1-6}$alkyl, halogen, —$CH_2F$, —$CHF_2$, —$CF_3$, —$CO_2H$, and —$CO_2C_{1-6}$alkyl. In another subclass of this class, each $R^f$ is independently selected from: $C_{1-6}$alkyl, and phenyl, wherein alkyl and phenyl are unsubstituted or substituted with 1, 2, 3 or 4 substituents selected from: oxo, —OH, —CN, —$NH_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl. In a subclass of this subclass, each $R^f$ is independently selected from: $C_{1-6}$alkyl, and phenyl. In another subclass of this subclass, each $R^f$ is independently selected from: methyl, ethyl and phenyl.

In another class of this embodiment, $R^i$ is independently selected from: $C_{1-6}$alkyl, $C_{4-7}$cycloalkyl, $C_{4-7}$cycloalkenyl, $C_{3-7}$cycloheteroalkyl, $C_{3-7}$cycloheteroalkenyl, aryl, and heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —$C_{1-6}$alkyl, —$OC_{1-6}$alkyl, halogen, —$CH_2F$, —$CHF_2$, —$CF_3$, —$CO_2H$, —$CO_2C_{1-6}$ alkyl, —$C_{3-7}$cycloalkyl, and heteroaryl. In a subclass of this class, $R^i$ is independently selected from: $C_{1-6}$alkyl, and aryl, wherein alkyl and aryl are unsubstituted or substituted with 1, 2, or 3 substituents selected from: oxo, —OH, —CN, —$NH_2$, —$C_{1-6}$alkyl, —$OC_{1-6}$alkyl, halogen, —$CH_2F$, —$CHF_2$, —CF$_3$, —CO$_2$H, and —CO$_2$C$_{1-6}$alkyl. In a subclass of this subclass, R$^i$ is independently selected from: C$_{1-6}$alkyl, and phenyl, wherein alkyl and phenyl are unsubstituted or substituted with 1, 2, or 3 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In another subclass of this subclass, R$^i$ is independently selected from: methyl, ethyl and phenyl.

In another embodiment of the present invention, n is 0, 1, 2, 3 or 4. In a class of this embodiment, n is 1, 2 or 3. In another class of this embodiment, n is 0, 1 or 2. In another class of this embodiment, n is 0. In another class of this embodiment, n is 1. In another class of this embodiment, n is 2. In another embodiment of the present invention, m is 0, 1, 2, 3, or 4. In a class of this embodiment, m is 1, 2 or 3. In another class of this embodiment, m is 0, 1 or 2. In another class of this embodiment, m is 0 or 1. In another class of this embodiment, m is 0. In another class of this embodiment, m is 1. In another embodiment of the present invention, p is 0, 1, 2 or 3. In a class of this embodiment, p is 1, 2 or 3. In another class of this embodiment, p is 0, 1 or 2. In another class of this embodiment, p is 0 or 2. In another class of this embodiment, p is 0. In another class of this embodiment, p is 1. In another class of this embodiment, p is 2. In another embodiment of the present invention, q is 0, 1, 2, 3 or 4. In a class of this embodiment, q is 1, 2 or 3. In another class of this embodiment, q is 0, 1 or 2. In another class of this embodiment, q is 1 or 2. In another class of this embodiment, q is 0. In another class of this embodiment, q is 1. In another class of this embodiment, q is 2. In another embodiment of the present invention, r is 0, 1 or 2. In a class of this embodiment, r is 0 or 1. In another class of this embodiment, r is 0. In another class of this embodiment, r is 1. In another class of this embodiment, r is 2. In another embodiment of the present invention, s is 0, 1, 2, 3 or 4. In a class of this embodiment, s is 0, 1, 2 or 3. In a class of this embodiment, s is 0, 1 or 2. In another class of this embodiment, s is 0 or 1. In another class of this embodiment, s is 1 or 2. In another class of this embodiment, s is 0 or 2. In another class of this embodiment, s is 0. In another class of this embodiment, s is 1. In another class of this embodiment, s is 2. In another class of this embodiment, s is 3.

The compound of structural formula I includes the compounds of structural formulas Ia, Ib, Ic, Id, Ie, If, Ig, Ih and Ii:

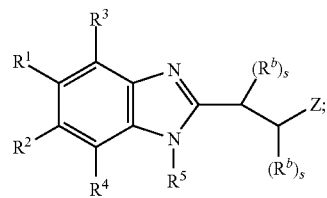
(Ia)

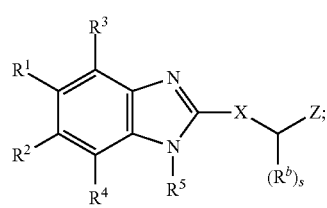
(Ib)

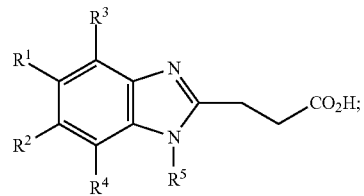
(Ic)

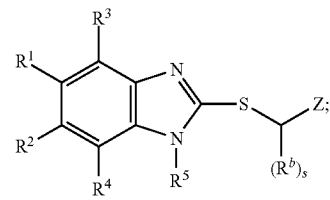
(Id)

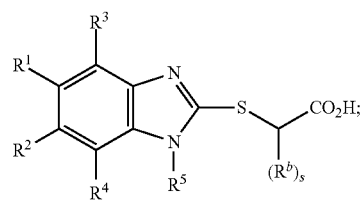
(Ie)

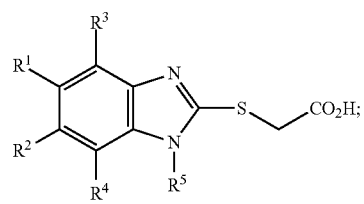
(If)

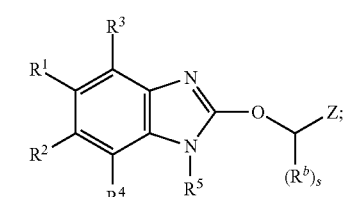
(Ig)

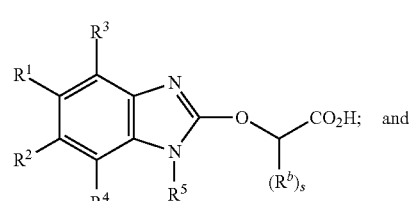
(Ih) and

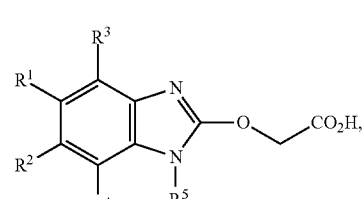
(Ii)

wherein s is 0, 1 or 2;

and pharmaceutically acceptable salts, hydrates and solvates thereof.

Illustrative, but non-limiting, examples of the compounds of the present invention that are useful as activators of AMP-protein kinase are the following benzimidazoles.

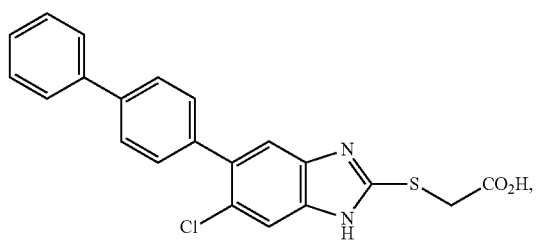

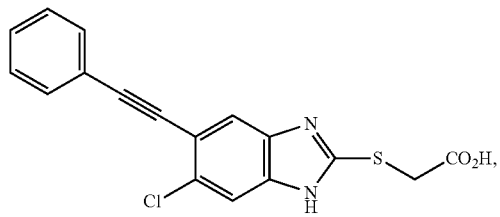

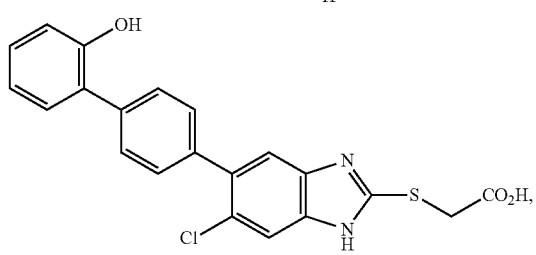

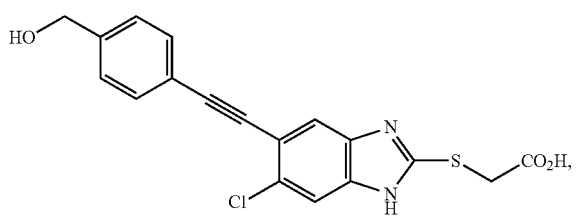

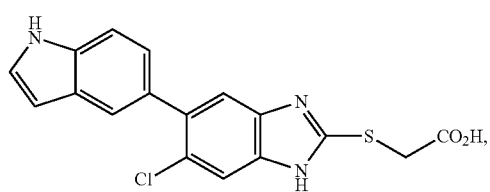

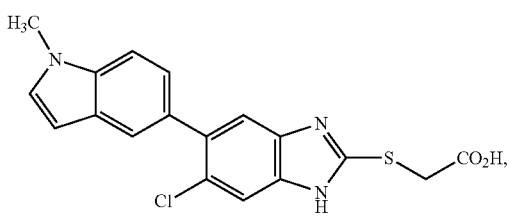

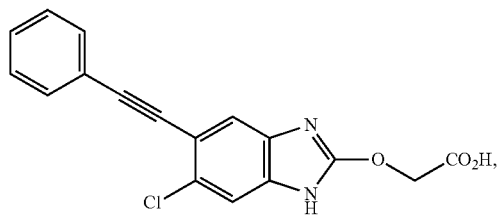

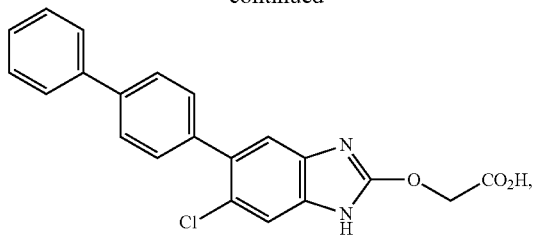

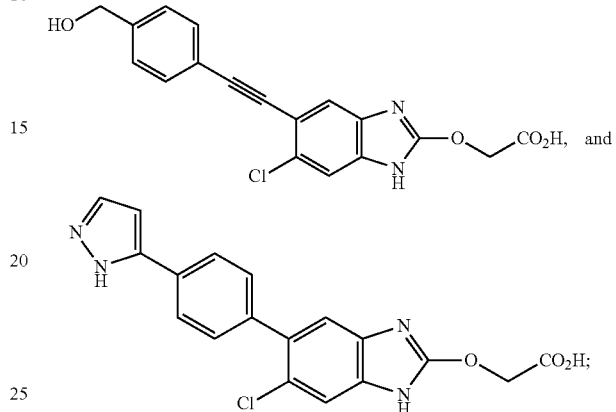

or a pharmaceutically acceptable salt thereof.

"Alkyl", as well as other groups having the prefix "alk", such as alkoxy, alkanoyl, means carbon chains of up to 10 carbons which may be linear or branched or combinations thereof. Examples of alkyl groups include methyl, ethyl, n-propyl, isopropyl, butyl, isobutyl, sec- and tert-butyl, pentyl, hexyl, heptyl, octyl, nonyl, and the like.

"Alkenyl" means carbon chains up to 10 carbons which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like. In one embodiment of the present invention, alkenyl is vinyl.

"Alkynyl" means carbon chains up to 10 carbons which contain at least one carbon-carbon triple bond, and which may be linear or branched or combinations thereof. Examples of alkynyl include ethynyl, propargyl, 3-methyl-1-pentynyl, 2-heptynyl and the like. In one embodiment of the present invention, alkynyl is ethynyl.

"Cycloalkyl" means mono- or bicyclic or bridged saturated carbocyclic rings, each having from 3 to 14 carbon atoms. Examples of cycloalkyl include cyclopropyl, cyclobutyl, cyclopentyl, cyclohexyl, cycloheptyl, cyclooctyl, and decahydronaphthyl, and the like. In one embodiment of the present invention, cycloalkyl is selected from cyclopentyl and cyclohexyl. In another embodiment of the present invention, cycloalkyl is selected from cyclopropyl, cyclopentyl, and cyclohexyl.

"Cycloalkenyl" means nonaromatic, mono- or bicyclic or bridged carbocyclic rings, each having from 3 to 14 carbon atoms and containing at least one double bond. Examples of cycloalkyl include cyclopropenyl, cyclobutenyl, cyclopentenyl, cyclohexenyl, cycloheptenyl, cyclooxtenyl, decahydronaphthyl, bicyclo[2.2.1]hept-5-en-2-yl, and the like.

"Cycloheteroalkyl" means nonaromatic, mono- or bicyclic or bridged saturated carbocyclic rings, each having from 2 to 14 carbon atoms and containing 1, 2, 3, 4 or 5 heteroatoms selected from N, NH, O and S. Examples of cycloheteroalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazobicyclo[3.2.1]-octane, and hexahydroindazolyl. The cycloheteroalkyl ring may be substituted on the ring carbons and/or the ring nitrogens. In one embodiment of the present invention, cycloheteroalkyl is selected from piperidine, pyrrolidine, oxazolidine, 1,3-oxazolidine-2,4-dione, thiazolidine, 1,3-thiazolidine-2,4-dione, imidazolidine, and hydantoin, and the like. In another embodiment of the present invention cycloheteroalkyl is selected from: morpholine, pyrrolidine, piperazine, and piperidine. In another embodiment of the present invention, cycloheteroalkyl is imidazolidine.

"Cycloheteroalkenyl" means nonaromatic mono- or bicyclic or bridged rings each having from 2 to 14 carbon atoms containing at least one double bond and containing 1, 2, 3, 4 or 5 heteroatoms selected from N, NH, O and S. Examples of cycloheteroalkenyl include 1,2,4-oxadiazol-5-one, 1,2,4-thiadiazol-5-one, 1,2,4-triazol-3-one, and 1,2,3,6-tetrahydropyridine, dihydro-1,3,4-oxadiazole, and [1,6]-dihydropyridine and the like. In one embodiment of the present invention, cycloheteroalkenyl is dihydro-1,3,4-oxadiazole. In another embodiment of the present invention, cycloheteroalkenyl is [1,6]-dihydropyridine.

"Aryl" means a monocyclic, bicyclic or tricyclic ring system containing 5-14 carbon atoms, wherein at least one of the rings is aromatic. Aryl thus includes ring systems in which an aromatic ring is fused to a non-aromatic ring, such as a cycloalkyl or cycloalkenyl ring. Examples of aryl include phenyl, naphthalene, biphenyl, indane and 5,6,7,8-tetrahydronaphthalene, and the like. In one embodiment of the present invention, aryl is phenyl, naphthalene, biphenyl, indane, and 5,6,7,8-tetrahydronaphthalene. In another embodiment of the present invention, aryl is phenyl, naphthalene, indane and 5,6,7,8-tetrahydronaphthalene. In one class of this embodiment, aryl is phenyl and naphthalene. In another class of this embodiment, aryl is phenyl. In another class of this embodiment, aryl is naphthalene.

"Heteroaryl" means a monocyclic, bicyclic or tricyclic ring system containing 5-14 carbon atoms and containing 1, 2, 3, 4 or 5 heteroatoms selected from N, NH, O and S wherein at least one of the heteroatom containing rings is aromatic. Heteroaryl thus includes ring systems in which an aromatic heteroatom containing ring is fused to a non-aromatic ring, such as a cycloalkyl, cycloalkenyl, cycloheteroalkyl or cycloheteroalkenyl ring, and also includes ring systems in which an aryl ring is fused to a non-aromatic heteroatom containing ring, such as acycloheteroalkyl or cycloheteroalkenyl ring. Examples of heteroaryls include: pyrazole, pyridine, pyrazine, pyrimidine, thiazole, thiophene, benzoimidazole, quinoline, isoquinoline, indole, indazole, carbazole, benzotriazole, benzofuran, benzothiazole, benzothiophene, benzoisooxazole, oxazole, furan, benzoxazole, isoxazole, indoline, isoindoline, tetrazole, imidazole, oxadiazole, thiadiazole, triazole, benzothiazole, bernzopyrazole, imidazopyridine, benzodioxole, dihydropyridine, dihydropyrrolopyridine, dihydrobenzooxazine, benzodioxole, benzodioxine, pyrrolopyridine, triazolopyridine, dihydropyridooxazine, dihydrobenzoxazine, dihydroindole, dihydroisoindole, dihydrobenzoimidazole, dihydroquinoline, tetrahydroisoquinoline, tetrahydrocyclopentaindole, tetrahydroquinoxaline, and tetrahydropyridine. In one embodiment of the present invention, heteroaryl is selected from: imidazole, pyrazole, pyridine, pyrazine, pyrimidine, thiazole, thiophene, benzoimidazole, quinoline, isoquinoline, indole, indazole, carbazole, benzotriazole, benzofuran, benzothiazole, benzo[b]thiophene, benzo[d]isooxazole, 3,4-dihydro-2H-benzo[1,4]oxazine, benzo[1,3]dioxole, benzo[1,4]dioxine, 1H-pyrrolo[2,3-b]pyridine, 1,6-dihydro-pyridine, [1,2,4]triazolo[4,3-a]pyridine, 3,4 dihydropyrido[3,2-b][1,4]oxazine, 3,4-dihydro-2H-1,4-benzoxazine, 2,3-dihydro-1H-indole, 2,3-dihydro-1H-isoindole, 2,3-dihydrobenzoimidazole, 1,2-dihydroquinoline, 1,2,3,4-tetrahydroisoquinoline, 1,2,3,4-tetrahydrocyclopenta[b]indole, 1,2,3,4-tetrahydroquinoxaline, and 1,2,3,6-tetrahydropyridine. In another embodiment of the present invention, heteroaryl is tetrazole. In another embodiment, heteroaryl is selected from: pyrazole, pyridine, pyrimidine, isoxazole, imidazole, oxazole, triazole, tetrazole, oxadiazole, thiazole, thiadiazole, and benzoxazole. In another embodiment of this invention, heteroaryl is tetrazole.

"Halogen" includes fluorine, chlorine, bromine and iodine. In one embodiment of the present invention, halogen is selected from fluorine, chlorine, and bromine.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

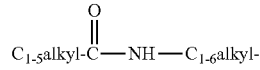

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are activators of the AMP-activated protein kinase. The methods of treatment of this invention comprises a method of activating AMPK-activated protein kinase and treating AMPK-activated protein kinase mediated diseases by administering to a patient in need of such treatment a non-toxic therapeutically effective amount of a compound of this invention that activate AMPK-activated protein kinase.

AMP-activated protein kinase (AMPK) is a heterotrimeric enzyme composed of a catalytic α subunit and regulatory β and γ subunits. There are two genes encoding isoforms of both the α and β subunits (α1, α2, β1 and β2) and three genes encoding isoforms of the γ subunit (γ1, γ2 and γ3) leading to 12 possible heterotrimeric combinations. The α2 isoform is predominately found in skeletal and cardiac muscle AMPK; both the α1 and α2 isoforms are found in hepatic AMPK; while in pancreatic islet β-cells the α1 isoform AMPK predominates. In particular, the compounds of structural formula I are activators of at least one heterotrimeric isoform of AMP-activated protein kinase.

An "activator" is a compound that either increases the activity (phosphorylation of downstream substrates) of fully phosphorylated AMPK or that increases the phosphorylation of AMPK.

The compounds of the present invention are efficacious in the treatment and prevention of diseases, disorders and conditions responsive to the activation of AMP-activated protein kinase, including but not limited to: type 2 diabetes, insulin resistance, hyperglycemia, obesity, hyperinsulinemia, glucose intolerance, atherosclerosis, metabolic Syndrome, hypertension, high hepatic glucose output, high blood glucose concentrations, nonalcoholic steatohepatitis, protection against ischemia and reperfusion damage, and lipid disorders, such as dyslipidemia, elevated levels of plasma triglycerides, elevated levels of free fatty acids, elevated levels of cholesterol, high levels of low density lipoprotein (LDL) and low levels of high density lipoprotein (HDL). The compounds are also useful for the treatment of cancer, hypoxia and glucocorticoid-induced apoptosis.

One or more of the following diseases may be treated by the administration of a therapeutically effective amount of a compound of Formula I, or a pharmaceutically acceptable salt thereof, to a patient in need of treatment: (1) non-insulin dependent diabetes mellitus (Type 2 diabetes); (2) hyperglycemia; (3) metabolic syndrome; (4) obesity; (5) hypercholesterolemia; (6) hypertriglyceridemia (elevated levels of triglyceride-rich-lipoproteins); (7) mixed or diabetic dyslipidemia; (8) low HDL cholesterol; (9) high LDL cholesterol; (10) atherosclerosis; and (11) hypertension. Also, the compounds of Formula I may be used for the manufacture of a medicament for treating one or more of the above diseases.

One embodiment of the uses of the compounds is directed to the treatment of one or more of the following diseases by administering a therapeutically effective amount to a patient in need of treatment: (1) Type 2 diabetes; (2) hyperglycemia; (3) metabolic syndrome; (4) obesity; (5) hypercholesterolemia; and (6) hypertension.

The compounds may also be used for manufacturing a medicament for use in the treatment of one or more of the above diseases.

The compounds are expected to be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds, compositions, methods and medicaments as described herein may also be effective in reducing the risks of adverse sequelae associated with metabolic syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others. By keeping hyperglycemia under control, the compounds may also be effective in delaying or preventing vascular restenosis and diabetic retinopathy.

The compounds of this invention may also have utility in improving or restoring β-cell function, so that they may be useful in treating type 1 diabetes or in delaying or preventing a patient with Type 2 diabetes from needing insulin therapy.

Other possible outcomes of treatment with the compounds of the present invention include, but are not limited to: 1) a decrease in fatty acid synthesis; 2) an increase in fatty acid oxidation and ketogenesis; 3) a decrease in cholesterol synthesis, lipogenesis, and triglyceride synthesis; 4) a decrease in blood glucose levels and concentration; 5) an improvement in glucose homeostasis; 6) a normalization of glucose metabolism; 7) a decrease in blood pressure; 8) an increase in HDL; 9) a decrease in plasma triglycerides; 10) a decrease in free fatty acids; 11) a decrease in hepatic glucose output; 12) an improvement in insulin action; 13) a decrease in blood pressure; 14) an improvement in insulin sensitivity; 15) a suppression of hepatic glucose output; 15) an inhibition of de novo lipogenesis; 16) stimulation of muscle glucose uptake; 17) modulation of insulin secretion by pancreatic β cells; and 16) a decrease in body weight.

The compounds generally may be efficacious in treating one or more of the following diseases: (1) Type 2 diabetes (also known as non-insulin dependent diabetes mellitus, or NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) abdominal obesity, (16) retinopathy, (17) metabolic syndrome, (18) high blood pressure (hypertension), and (19) insulin resistance.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example torcetrapib and those described in published applications WO2005/100298, WO2006/014413, and WO2006/014357), niacin and niacin receptor agonists, bile acid sequestrants, microsomal triglyceride transport inhibitors, and bile acid reuptake inhibitors. These combination treatments may be effective for the treatment or control of one or more related conditions selected from the group consisting of hypercholesterolemia, atherosclerosis, hyperlipidemia, hypertriglyceridemia, dyslipidemia, high LDL, and low HDL.

The present invention also relates to methods and medicaments for the treatment, control, or prevention of Type 2 diabetes by administering the compounds and pharmaceutical compositions of the present invention. The present invention also relates to methods and medicaments for the treatment, control, or prevention of Type 2 diabetes by administering the compounds of the present invention in combination with a therapeutically effective amount of another agent known to be useful to treat the condition. The present invention also relates to methods and medicaments for the treatment, control, or prevention of diabetes related disorders by administering the compounds and pharmaceutical compositions of the present invention alone, or in combination. The present invention also relates to methods and medicaments for the treatment and prevention of diabetes in pre-diabetic subject by administering the compounds and pharmaceutical compositions of the present invention alone, or in combination.

The present invention also relates to methods and medicaments for the treatment, control, or prevention of obesity by administering the compounds and pharmaceutical compositions of the present invention. The present invention also relates to methods and medicaments for the treatment, control, or prevention of obesity by administering the compounds of the present invention in combination with a therapeutically effective amount of another agent known to be useful to treat the condition. The present invention also relates to methods and medicaments for the treatment, control, or prevention of obesity related disorders by administering the compounds and pharmaceutical compositions of the present invention alone, or in combination. The present invention also relates to methods and medicaments for the treatment and prevention of obesity in overweight subject by administering the compounds and pharmaceutical compositions of the present invention alone, or in combination. The compounds are also useful for the treatment of obesity related disorders, or eating disorders associated with excessive food intake, and complications associated therewith, including left ventricular hypertrophy, as well as treating or preventing obesity in other mammalian species, including canines and felines.

The present invention also relates to methods and medicaments for the treatment, control, or prevention of hyperglycemia by administering the compounds and pharmaceutical compositions of the present invention. The present invention also relates to methods and medicaments for the treatment, control, or prevention of hyperglycemia by administering the compounds of the present invention in combination with a therapeutically effective amount of another agent known to be useful to treat the condition.

The present invention also relates to methods and medicaments for the treatment, control, or prevention of insulin resistance by administering the compounds and pharmaceutical compositions of the present invention. The present invention also relates to methods and medicaments for the treatment, control, or prevention of insulin resistance by administering the compounds of the present invention in combination with a therapeutically effective amount of another agent known to be useful to treat the condition.

The present invention also relates to methods and medicaments for the treatment, control, or prevention of lipid disorders by administering the compounds and pharmaceutical compositions of the present invention. The present invention also relates to methods and medicaments for the treatment, control, or prevention of lipid disorders by administering the compounds of the present invention in combination with a therapeutically effective amount of another agent known to be useful to treat the condition. The present invention also relates to methods and medicaments for the treatment, control, or prevention of dyslipidemia related disorders and lipid disorder-related disorders by administering the compounds and pharmaceutical compositions of the present invention alone, or in combination.

The present invention also relates to methods and medicaments for the treatment, control, or prevention of atherosclerosis by administering the compounds and pharmaceutical compositions of the present invention. The present invention also relates to methods and medicaments for the treatment, control, or prevention of atherosclerosis by administering the compounds of the present invention in combination with a therapeutically effective amount of another agent known to be useful to treat the condition. The present invention also relates to methods and medicaments for the treatment, control, or prevention of atherosclerosis related disorders by administering the compounds and pharmaceutical compositions of the present invention alone, or in combination.

The present invention also relates to methods and medicaments for the treatment, control, or prevention of hypertension by administering the compounds and pharmaceutical compositions of the present invention. The present invention also relates to methods and medicaments for the treatment, control, or prevention of hypertension by administering the compounds of the present invention in combination with a therapeutically effective amount of another agent known to be useful to treat the condition. The present invention also relates to methods and medicaments for the treatment, control, or prevention of hypertension related disorders by administering the compounds and pharmaceutical compositions of the present invention alone, or in combination. The present invention also relates to methods and medicaments for the treatment and prevention of hypertension in pre-hypertensive subject by administering the compounds and pharmaceutical compositions of the present invention alone, or in combination.

The present invention also relates to methods and medicaments for the treatment, control, or prevention of metabolic syndrome by administering the compounds and pharmaceutical compositions of the present invention. The present invention also relates to methods and medicaments for treating metabolic syndrome by administering the compounds of the present invention in combination with a therapeutically effective amount of another agent known to be useful to treat the condition.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention are useful for treating both Type 1 and Type 2 diabetes. The term "diabetes associated with obesity" refers to diabetes caused by obesity or resulting from obesity. The compositions are especially effective for treating Type 2 diabetes. The compositions of the present invention are also useful for treating and/or preventing gestational diabetes mellitus.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (≥140 mmHg/≥90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dyslipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared (kg/m$^2$). "Obesity" refers to a condition whereby an otherwise healthy subject has a Body Mass Index (BMI) greater than or equal to 30 kg/m$^2$, or a condition whereby a subject with at least one co-morbidity has a BMI greater than or equal to 27 kg/m$^2$. An "obese subject" is an otherwise healthy subject with a Body Mass Index (BMI) greater than or equal to 30 kg/m$^2$ or a subject with at least one co-morbidity with a BMI greater than or equal to 27 kg/m$^2$. An overweight subject is a subject at risk of obesity. A "subject at risk of obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m$^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asia-Pacific, a "subject at risk of obesity" is a subject with a BMI of greater than 23 kg/m$^2$ to less than 25 kg/m$^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, OH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The compounds of formula I are also useful for treating or preventing obesity and obesity-related disorders in cats and dogs. As such, the term "mammal" includes companion animals such as cats and dogs.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

Left ventricular hypertrophy (LVH) is identified based on left ventricular mass index (LVMI) and relative wall thickness (RWT). Left ventricular mass index is defined as left ventricular mass in grams divided by body surface area in meters$^2$. Relative wall thickness is defined as 2× posterior wall thickness/left ventricular end diastolic diameter. Normal LVMI values are typically 85 and normal RWT approximately 0.36. A male subject with LVH has a LVMI greater than 131 g/m$^2$; a female subject with LVH has a LVMI greater than 100 g/m$^2$. A subject with an elevated LVMI value is a male subject with a LVMI between 85 g/m$^2$ and 131 g/m$^2$, or a female subject with a LVMI between 85 g/m$^2$ and 100 g/m$^2$.

Treatment of cardiac hypertrophy, or left ventricular hypertrophy, refers to the administration of the combinations of the present invention to a subject with cardiac hypertrophy or left ventricular hypertrophy. Prevention of cardiac hypertrophy, or left ventricular hypertrophy, refers to the administration of the combinations of the present invention to decrease or maintain the LVMI in a subject with an elevated LVMI value or to prevent the increase of LVMI in a subject with a normal LVMI value.

One outcome of treatment of cardiac hypertrophy or left ventricular hypertrophy may be a decrease in ventricular mass. Another outcome of treatment of cardiac hypertrophy or left ventricular hypertrophy may be a decrease in the rate of increase of ventricular mass. Another outcome of treatment of cardiac hypertrophy or left ventricular hypertrophy may be a decrease in ventricular wall thickness. Another outcome of treatment of cardiac hypertrophy of left ventricular hypertrophy may be the decrease in the rate of increase in ventricular wall thickness.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 100 mg in one embodiment from about 0.01 mg to about 50 mg, and in another embodiment from 0.1 mg to 10 mg of a compound of Formula I per kg of body weight per day.

In the case where an oral composition is employed, a suitable dosage range is, e.g. from about 0.01 mg to about 1000 mg of a compound of Formula I per day. In one embodiment, the range is from about 0.1 mg to about 10 mg per day. For oral administration, the compositions are preferably provided in the form of tablets containing from 0.01 to 1,000 mg, preferably 0.01, 0.05, 0.1, 0.5, 1, 2, 2.5, 3, 4, 5, 6, 7, 8, 9, 10, 12, 12.5, 15, 20, 25, 30, 40, 50, 100, 250, 500, 750 or 1000 milligrams of the active ingredient for the symptomatic adjustment of the dosage to the patient to be treated.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, particularly a human or a companion animal such as a dog or cat, with an effective dosage of a compound of the present invention. For example, oral, rectal, topical, parenteral, ocular, pulmonary, and nasal routes of administration, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers, or as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those known to those of ordinary skill in that art.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet cachet or capsule contains from about 0.01 to 1,000 mg, particularly 0.01, 0.05, 0.1, 0.5, 1.0, 2, 2.5, 3, 4, 5, 6, 7, 8, 9, 10, 12, 15, 25, 30, 40, 50, 75, 100, 125, 150, 175, 180, 200, 225, 250, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular, intranasal, and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

hypertensive agents, anti-obesity agents, and anorectic agents, which may be administered separately or in the same pharmaceutical compositions.

The present invention also provides a method for the treatment or prevention of an AMPK-activated protein kinase (AMPK) mediated disease, which method comprises administration to a patient in need of such treatment or at risk of developing an AMPK mediated disease of an amount of an AMPK activator and an amount of one or more active ingredients, such that together they give effective relief.

In a further aspect of the present invention, there is provided a pharmaceutical composition comprising an AMPK activator and one or more active ingredients, together with at least one pharmaceutically acceptable carrier or excipient.

Thus, according to a further aspect of the present invention there is provided the use of an AMPK activator and one or more active ingredients for the manufacture of a medicament for the treatment or prevention of an AMPK mediated disease. In a further or alternative aspect of the present invention, there is therefore provided a product comprising an AMPK activator and one or more active ingredients as a combined preparation for simultaneous, separate or sequential use in the treatment or prevention of an AMPK mediated disease. Such a combined preparation may be, for example, in the form of a twin pack.

It will be appreciated that for the treatment or prevention of diabetes, obesity, hypertension, metabolic syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, metabolic syndrome, dyslipidemia, cancer, atherosclerosis, and

| Injectable Suspension (I.M.) | mg/mL | Tablet | mg/tablet |
|---|---|---|---|
| Compound of Formula I | 10 | Compound of Formula I | 25 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 43.5 |
| Benzalkonium chloride | 1.0 | Magnesium Stearate | 2.5 |
| Water for injection to a total volume of 1 mL | | | 500 |

| Capsule | mg/capsule | Aerosol | Per canister |
|---|---|---|---|
| Compound of Formula I | 25 | Compound of Formula I | 24 mg |
| Lactose Powder | 573.5 | Lecithin, NF Liq. Conc. | 1.2 mg |
| Magnesium Stearate | 1.5 | Trichlorofluoromethane, NF | 4.025 g |
| | 600 | Dichlorodifluoromethane, NF | 12.15 g |

Compounds of Formula I may be used in combination with other drugs that are used in the treatment/prevention/suppression or amelioration of the diseases, disorders or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: other anti-diabetic agents, anti-dyslipidemic agents, and antirelated disorders thereof, which method comprises administration to a patient in need of such treatment an amount of a compound of the present invention and an amount of another pharmaceutical agent effective to threat that disorder, such that together they give effective relief.

The present invention also provides a method for the treatment or prevention of diabetes, obesity, hypertension, metabolic syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

Suitable pharmaceutical agents of use in combination with a compound of the present invention, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and Al-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC 1131, BIM51077, CS 872, TH0318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, ATI-802, E3080, and the like; (26) carnitine palmitoyl transferase inhibitors such as ST 1327, and ST 1326, and the like; (27) Fructose 1,6-bisphosphohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; and 40) insulin secretagogues;

(b) anti-dyslipidemic agents such as (1) bile acid sequestrants such as, cholestyramine, colesevelam, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as JTT 705 (Japan Tobacco), torcetrapib, CP 532,632, BAY63-2149 (Bayer), SC 591, SC 795, and the like; (7) squalene synthetase inhibitors; (8) anti-oxidants such as probucol, and the like; (9) PPARα agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTCO179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequestrants such as colesevelam (WELCHOL/CHOLESTAGEL), colestipol, cholestyramine, and dialkylaminoalkyl derivatives of a cross-linked dextran, (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, Bioral Apo A1 targeted to foam cells, and the like; (29) IBAT inhibitors such as BARI143/HMR145A/HMR1453 (Sanofi-Aventis, PHA384640E (Pfizer), 58921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as taranabant, rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), O1691 (Organix), ORG14481 (Organon), VER24343 (Vernalis), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349

(Arena Pharmaceuticals), GW803430 (GlaxoSmithkline), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/ University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A,S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (Glaxo-SmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) β3 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. No. 5,705,515, U.S. Pat. No. 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, aminone, milrinone, cilostamide, rolipram, and cilomilast, as well as those described in WO 03/037432, WO 03/037899; (33) thyroid hormone p agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), saxagliptin, alogliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune) Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7™ Pharma), PYY336 (Emisphere Technologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neurotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) *Hoodia* and *trichocaulon* extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, a minorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl){3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl){3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2- methylpropyl}azetidin-1-yl)(4-chlorophenyl)methyl]benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl)methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl]methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H),4'-piperidine]-1'-carboxamide, 3-oxo-N-(7-trifluoromethylpyrido[3,2-b]pyridin-2-yl)spiro-[isobenzofuran-1(3H),4'-piperidine]-1'-carboxamide, N-[5-(3-fluorophenyl)-2-pyrimidinyl]-3-oxospiro-[isobenzofuran-1(3H),4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-N-[1-(3,5-difluorophenyl)-4-imidazolyl]-3-oxospiro[7-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide, trans-N-[1-(2-fluorophenyl)-3-pyrazolyl]-3-oxospiro[6-azaisobenzofuran-1(3H),1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-3-oxo-N-(2-phenyl-1,2,3-triazol-4-yl)spiro[6-azaisobenzofuran-1(3H),1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro[chroman-2,4'-piperidin]-4-one; and pharmaceutically acceptable salts and esters thereof.

Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{-4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl]propoxy}phenyl)pyrido[2,3-d]pyrimidin-4(3H)-one 2-methyl-3-(4-{3-[(3S)-3-methylpiperidin-1-yl]propoxy}phenyl)pyrido[4,3-d]pyrimidin-4(3H)-one, 3-{4-

[(1-cyclobutyl-4-piperidinyl)oxy]phenyl}-2,5-dimethyl-4 (3H)-quinazolinone, 3-{4-[(1-cyclobutyl-4-piperidinyl)oxy] phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4 (3H)-one, 3-{4-[(1-cyclobutylpiperidin-4-yl)oxy]phenyl}-6-fluoro-2-methylpyrido[3,4-d]pyrimidin-4(3H-one, 3-{4-[(1-cyclobutyl-4-piperidinyl)oxy]phenyl}-2-ethylpyrido[4,3-d] pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy] phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy] phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl) propoxy]phenyl}-4(3H)-quinazolinone, 5-methoxy-2-methyl-3-(4-{3-[(3S)-3-methylpiperidin-1-yl] propoxy}phenyl)-4(3H)-quinazolinone, 7-methoxy-2-methyl-3-(4-{3-[(3S)-3-methylpiperidin-1-yl] propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl] propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl] carbonyl}-1-piperazinyl)-1-naphthoic acid; 3-(4-{[1-(3-ethoxyphenyl)-2-(4-fluorophenyl)-1H-imidazol-4-yl] carbonyl}-1-piperazinyl)-1-naphthoic acid; 3-(4-{[1-(3-ethoxyphenyl)-2-(2,4-difluorophenyl)-1H-imidazol-4-yl] carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl) ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b] pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H, 5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methylpropane-nitrile; and pharmaceutically acceptable salts thereof.

Suitable neurokinin-1 (NK-1) receptor antagonists may be favorably employed with the AMP-kinase activators of the present invention. NK-1 receptor antagonists of use in the present invention are fully described in the art. Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperidin-3-amine; 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; RO67319; R1124; R1204; SSR146977; SSR240600; T-2328; and T2763; or a pharmaceutically acceptable salts thereof.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula Ito the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The compounds of structural formula I of the present invention can be prepared according to the procedures of the following Schemes, Intermediates and Examples, using appropriate materials and are further exemplified by the following specific examples. Moreover, by utilizing the procedures described in the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those previously described herein. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., Protective Groups in Organic Synthesis, John Wiley & Sons, Inc., New York, N.Y., 1991. CBZ and BOC are commonly used protecting groups in organic synthesis, and their removal conditions are known to those skilled in the art. All temperatures are degrees Celsius unless otherwise noted. Mass spectra (MS) were measured by electron-spray ion-mass spectroscopy.

Abbreviations used in the description of the preparation of the compounds of the present invention: aq is aqueous; ACN is acetonitrile; AcOH is acetic acid; Bn is benzyl; BnBr is benzyl bromide; C is carbon; conc is concentrated; d is day(s); DAST is (diethylamino)sulfur trifluoride; DIBAL-H is di-isobutyl aluminum hydride; DCM is dichloromethane; DME is 1,2-dimethoxyethane; DMF is dimethyl formamide; DMSO is dimethyl sulfoxide; dppf is 1,1'-bis(diphenylphosphino)-ferrocene; Et is ethyl; EtO is ethoxy; $Et_2O$ is diethyl ether; EtOAc is ethyl acetate; EtOH is ethanol; $Et_3N$ is triethyl amine; $Et_3Si$ is triethyl silane; eq is equivalent; g is gram(s); h is hour(s); HMDS is hexamethyldisilizane; HPLC is high pressure liquid chromatography; i-Pr is isopropyl; O-i-Pr is isopropoxy; KOAc is potassium acetate; L is liter; LC/MS is liquid chromatography/mass spectroscopy; LDA is lithium diisopropyl amide; M is molar; ml or mL is milliliter; Me is methyl; MeCN is acetonitrile; MeI is methyl iodide; MeO is methoxy; MeOH is methanol; min is minutes; mm is millimeters of mercury; mmol is millimole(s); MP or Mp or mp is melting point; MPLC is medium pressure liquid chromatography; N is normal; NaOAc is sodium acetate; NBS is N-bromo succinamide; NIS is N-iodo succinamide; $PPh_3$ is triphenyl phosphine; wt % is weight percent; psi is pounds per square inch; RT or r.t. or rt is room temperature; Rt is retention time; Rochelles' Salt is potassium sodium tartrate; SEM is 2-(trimethylsilyl)-ethoxymethyl; SEMCl is 2-(trimethylsilyl)-ethoxymethyl chloride; $Bu_4NF$ and TBAF is tetrabutyl ammonium fluoride; TBS is tert-butyl dimethyl silyl chloride; TBSCl is tert-butyl dimethyl silyl chloride; TFA is trifluoro acetic acid; THF is tetrahydrofuran; TLC is thin layer chromatography; TMS is tetramethylsilyl; and TMSBr is tetramethylsilyl bromide.

Microwave (MW or mw) reactions were performed with a single mode operating Biotage Emrys Optimizer in sealed reaction vials at the indicated fixed temperature held constant for the designated reaction time. The medium pressure liquid chromatography (MPLC) purifications were performed with Teledyne ISCO RediSep normal-phase columns pre-packed with 35-60 micron silica gel. The LC-MS system contained an Applied Biosystems API150EX MS operating in a positive ion mode receiving 0.1 mL/min flowrate with a Shimadzu UV detector receiving 0.1 mL/min flowrate. Unless specified, the LC conditions were solvent A=0.03% TFA in acetonitrile; solvent B=0.05% TFA in water; flowrate=10 mL/min; column: Chromolith Performance RP-18e, 100×4.6 mm; gradient program: min (% B) 0 (95), 1.6 (5), 2.6 (5), 2.7 (95), 3.0 (95). Unless specified, the $^1H$ NMRs were obtained in DMSO-$d_6$ at 300 or 500 MHz and spectra were recorded in units δ with $CD_2HS(O)CD_3$ (δ 2.504) as the reference line internal standard. C, H, N microanalyses were performed by Robertson Microlit Laboratories, Inc., Madison, N.J.

The following reaction schemes illustrate methods which may be employed for the synthesis of the compounds of structural formula I described in this invention. All substituents are as defined above unless indicated otherwise. Several strategies based upon synthetic transformations known in the literature of organic synthesis may be employed for the preparation of the title compounds of general formula I.

Intermediate 1

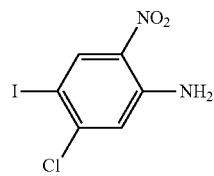 [SMILES: Nc1cc(Cl)c(I)cc1[N+](=O)[O-]]

5-chloro-4-iodo-2-nitroaniline

To a solution of 5-chloro-2-nitroaniline (25 g, 145 mmol) in AcOH (250 mL) was added N-iodosuccinimide (32.6 g 145 mmol). The mixture was stirred overnight at 50° C., cooled to rt and filtered. The solid residue was washed with AcOH, water, saturated aqueous $NaHCO_3$ and water, and then dried to afford the desired product as a brown solid, which was used in the next step without further purification.

Intermediate 2

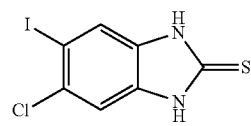

5-chloro-6-iodo-1,3-dihydro-2H-benzimidazole-2-thione

Step A 4-chloro-5-iodobenzene-1,2-diamine

To a suspension of 5-chloro-4-iodo-2-nitroaniline (Intermediate 1, 36.5 g, 122 mmol) in EtOH (800 mL) and water (150 mL) was added iron powder (38 g, 673 mmol) and $NH_4Cl$ (16 g, 306 mmol). The mixture was heated under nitrogen at 50° C. overnight. Additional iron powder (38 g, 673 mmol) and $NH_4Cl$ (16 g, 306 mmol) were added and heating was continued for 45 h. The reaction mixture was cooled, filtered and concentrated. The residue was re-dissolved in ethyl acetate and washed with sodium bicarbonate solution. The organic phase was concentrated to afford the desired product as a gray solid, which was used in the next step without further purification.

Step B 5-chloro-6-iodo-1,3-dihydro-2H-benzimidazole-2-thione

KOH (15.7 g, 238 mmol) in water (50 mL), followed by carbon disulfide (14.4 mL, 238 mmol), was added to a solution of 4-chloro-5-iodobenzene-1,2-diamine (50 g, 198 mmol) in EtOH (300 mL). The mixture was heated at reflux for 3 h, cooled and filtered. To the filtrate was added water (300 mL) and then AcOH (25 mL) in water (50 mL). The precipitate was collected, washed with water and a small amount of EtOH and dried to afford the desired product as a brown powder, which was used in the next step without further purification.

Intermediate 3

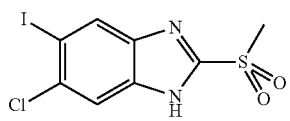

6-chloro-5-iodo-2-(methylsulfonyl)-1H-benzimidazole

Step A
6-chloro-5-iodo-2-(methylthio)-1H-benzimidazole $K_2CO_3$ (0.22 g, 1.61 mmol), followed by iodomethane (0.1 mL, 1.61 mmol), was added to a solution of 5-chloro-6-iodo-1,3-dihydro-2H-benzimidazole-2-thione (Intermediate 2, 1 g, 3.22 mmol) in acetone (20 mL) at 0° C. The reaction was stirred at rt for 1 h. Additional $K_2CO_3$ (1.61 mmol) and iodomethane (1.61 mmol) were added, and stirring continued at rt overnight. Volatiles were removed and the residue was partitioned between EtOAc and water. Concentration afforded the desired product as a white foam, which was used in the next step without further purification.

Step B 6-chloro-5-iodo-2-(methylsulfonyl)-1H-benzimidazole m-Chloroperbenzoic acid (1.4 g, 6.16 mmol) was added to a suspension of 6-chloro-5-iodo-2-(methylthio)-1H-benzimidazole (1.0 g, 3.08 mmol) in DCM (50 mL). The reaction stirred at rt for 10 min then washed with 10% aqueous $NaHCO_3$. The organic phase was concentrated. The residue was triturated with MeOH (3 mL) and filtered to afford the title compound as white powder. LC-MS: calculated for $C_8H_6ClIN_2O_2S$ 356.57, observed m/e 357.30 $(M+H)^+$ $(R_t$ 1.21/2 min). NMR $(CD_3OD)$: 8.3 (1H, s), 7.9 (1H, s), 3.3 (3H, s).

Intermediate 4

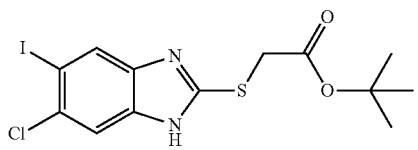 [SMILES: CC(C)(C)OC(=O)CSc1nc2cc(I)c(Cl)cc2[nH]1]

Tert-butyl 2-(6-chloro-5-iodo-1H-benzo[d]imidazol-2-ylthio)acetate $Cs_2CO_3$ (2.3 g, 7.08 mmol), followed by text-butyl bromoacetate (0.52 mL, 3.54 mmol), was added to a solution of 5-chloro-6-iodo-1,3-dihydro-2H-benzimidazole-2-thione (Intermediate 2, 1.1 g, 3.54 mmol) in THF (20 mL) at 0° C. The reaction was stirred at rt for 0.5 h. Volatiles were removed and the residue was partitioned between EtOAc and water. Concentration afforded the desired product as a white power. LC-MS: calculated for $C_{13}H_{14}ClIN_2O_2S$ 423.95, observed m/e 424.8 $(M+H)^+$.

Intermediate 5

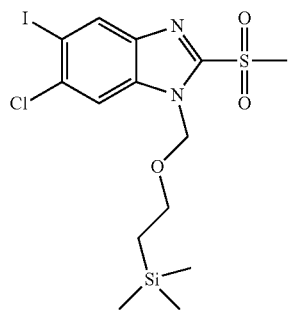 [SMILES: C[Si](C)(C)CCOCn1c(S(C)(=O)=O)nc2cc(I)c(Cl)cc21]

6-chloro-5-iodo-2-(methylsulfonyl)-1-{[2-(trimethylsilyl)ethoxy]methyl}-1H-benzimidazole $Et_3N$ (20.95 mL, 150 mmol) and 2-(trimethylsilyl)ethoxy methyl chloride (17.29 mL, 98 mmol) were added to a solution of Intermediate 3 (26.8 g, 75 mmol) in THF (200 mL). The reaction was stirred at rt for 1 h. Volatiles were removed and the residue partitioned between EtOAc and water. The organic phase was washed with 2N aqueous HCl and brine, dried $(MgSO_4)$ and concentrated to afford the title compound as a white solid. LC-MS: calculated for $C_{14}H_{20}ClIN_2O_3SSi$ 485.97, observed m/e 428.83 $(M+H)^+$ $(R_t$ 2.30 min).

Intermediate 6

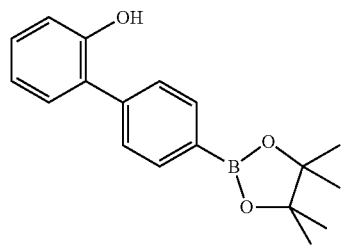 [SMILES: CC1(C)OB(c2ccc(-c3ccccc3O)cc2)OC1(C)C]

4'-(4,4,5,5-tetramethyl-1,3,2-dioxaborolan-2-yl)biphenyl-2-ol

Step A 4'-bromobiphenyl-2-ol

Potassium phosphate (2 M in water) (5.5 ml, 10.9 mmol) and $Pd(PPh_3)_4$ (209 mg, 0.18 mmol) were added to a solution of 1-bromo-4-iodobenzene (2.05 g, 7.25 mmol), and 2-hydroxybenzeneboronic acid (1 g, 7.25 mmol) in dioxane (50 mL). The reaction was heated at 100° C. for 1 h. Volatiles were removed and the residue was purified by chromatography over silica eluting with 0-50% EtOAc/hexane to afford the desired product as a light yellow oil.

Step B 4'-(4,4,5,5-tetramethyl-1,3,2-dioxaborolan-2-yl)biphenyl-2-ol

Potassium acetate (366 mg, 3.73 mmol) and dichloro[1,1'-bis(diphenylphosphino)ferrocene]palladium II DCM adduct (25.4 mg, 31 μmol) were added to a solution of 4′-bromobiphenyl-2-ol (310 mg, 1.24 mmol), and bis(pinacolato)diboron (348 mg, 1.37 mmol) in DME (3 mL). The reaction was heated at 150° C. under microwave irradiation for 10 min. Reaction mixture was filtered through a pad of Celite™ and purified by chromatography over silica eluting with 0-50% EtOAc/hexane to furnish the title compound as a white solid.

Intermediate 7

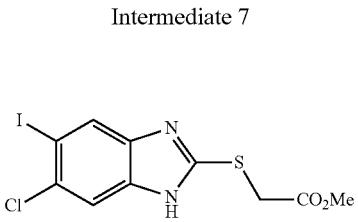

Methyl 2-(6-chloro-5-iodo-1H-benzo[d]imidazol-2-ylthio)acetate

A mixture of 6-chloro-5-iodo-2-thio-1H-benzo[d]imidazole (Intermediate 2; 4.00 g, 12.9 mmol), methyl bromoacetate (1.2 mL, 12.9 mmol), and $Cs_2CO_3$ (8.41 g, 25.8 mmol) in 65 mL of THF was stirred for 2.5 h at rt. The volume of the solvent was reduced by rotary evaporation to about 20 mL, the mixture was diluted with 200 mL of EtOAc and washed with brine, dried ($MgSO_4$) and evaporated. The resulting residue was subjected to chromatography on an 80 g column of $SiO_2$ eluting with 14% EtOAc in hexanes, followed by 20% to provide the title compound as an amorphous solid, which exists as a tautomer mixture in DMSO according to $^1$H NMR: $^1$H NMR (500 MHz, DMSO-$d_6$): δ 3.66, 3.72, 3.73 (s each, 3H), 4.24, 4.25, 4.26 (s each, 2H), 7.71, 7.95 (s each, 1H), 7.99, 8.11, 8.22 (s each, 1H), 12.91 (br s, 1H); LC-MS: calculated for $C_{10}H_8ClIN_2O_2S$ 382.6, observed m/e 382.9/384.9 (M+H)$^+$.

Intermediate 8

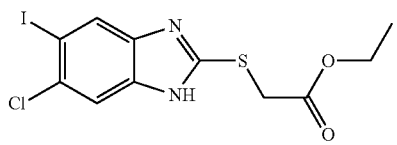 [SMILES: CCOC(=O)CSc1nc2cc(I)c(Cl)cc2[nH]1]

(6-Chloro-5-iodo-1H-benzoimidazol-2-ylsulfanyl)-acetic acid ethyl ester was prepared according to the procedure described for Intermediate 7.

Intermediate 9

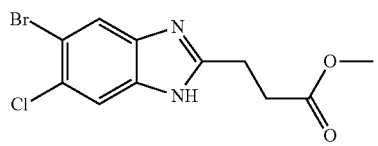 [SMILES: COC(=O)CCc1nc2cc(Br)c(Cl)cc2[nH]1]

3-(5-bromo-6-chloro-1H-benzimidazol-2-yl)-propionic acid methyl ester may be prepared from the 5-bromo-6-chloro-phenyldiamine according to the procedure disclosed in Synthesis of new trifluoromethyl-substituted 11H-isoindolo[2,1-a]benzimidazol-11-one derivatives, Lingaiah, Boddupally P. V.; Yakaiah, Tallapally; Rao, Pamulaparthy S.; and Narsaiah, Banda, Heterocycles (2005), 65(10), 2329-2337.

General Scheme 1

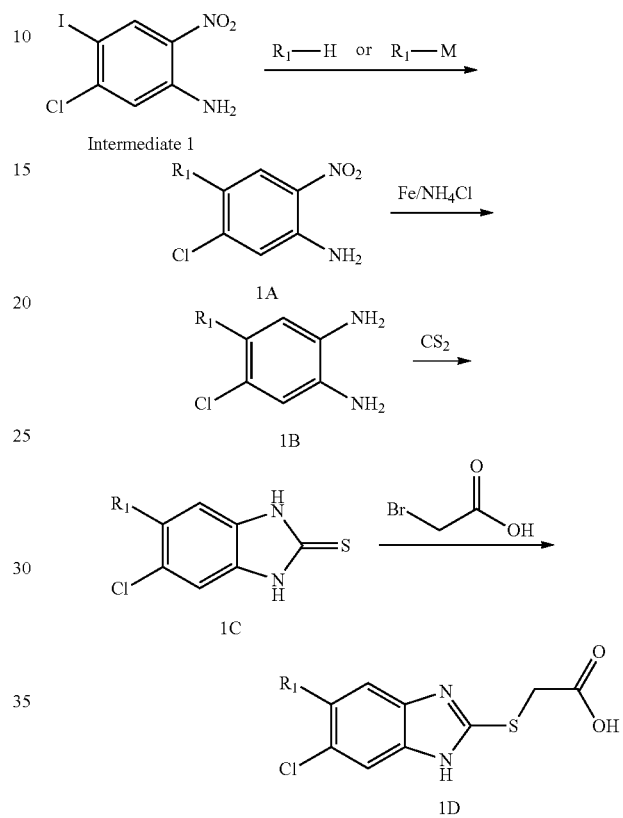

In General Scheme 1, Intermediate 1 is reacted with a boronic acid, boronate ester or stannane ($R^1$-M) in the presence of palladium catalyst to afford compound 1A. Alternatively, Intermediate 1 is reacted with an acetylene ($R^1$—H) in the presence of palladium catalyst to afford compound 1A. The subsequent reduction of 1A with iron powder/ammonium chloride affords benzyldiamine 1B. Treatment of compound 1B with carbon disulfide under basic conditions gives 1,3-dihydro-2H-benzimidazole-2-thione 1C. The subsequent reaction with bromoacetic acid affords the final 2-substituted benzimidazole product.

Example 1

(6-Chloro-5-phenylethynyl-1H-benzoimidazol-2-ylsulfanyl)-acetic acid

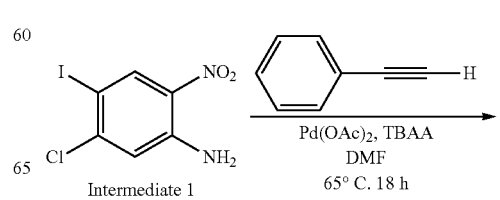

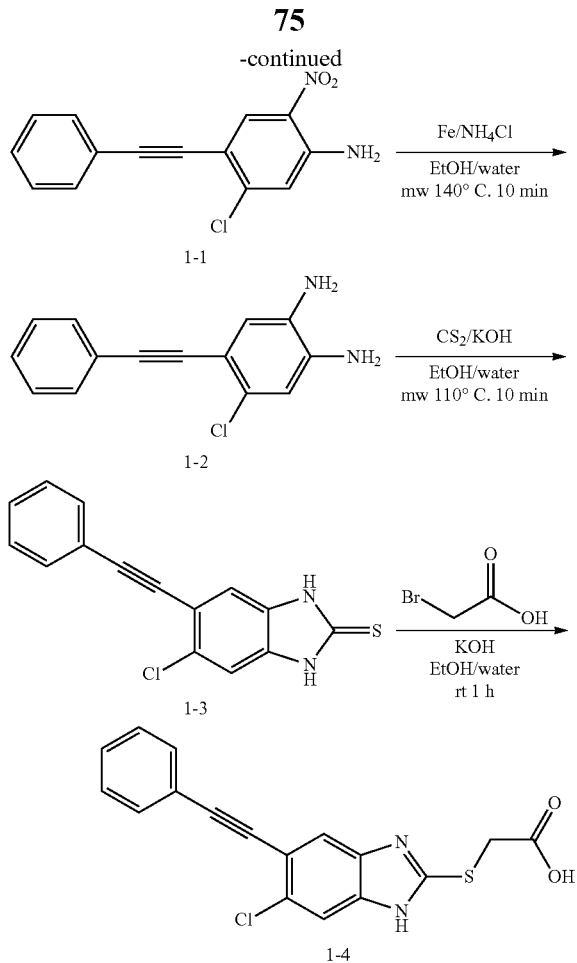

Step A
5-Chloro-2-nitro-4-phenylethynyl-phenylamine (1-1)

A 20 mL scintillation vial equipped with a stirring bar and a septum cap was charged with Pd(OAc)$_2$ (5.6 mg, 5 mol %) and 5-chloro-4-iodo-2-nitro-phenylamine (Intermediate 1, 149.0 mg, 0.500 mmol). The vial was purged with N$_2$ and a solution of ethynyl-benzene (56.1 mg, 0.549 mmol) was added followed by a solution of tetrabutylammonium acetate (182.0 mg, 0.750 mmol) in DMF (3 mL). The resulting mixture was stirred at 65° C. for 18 h, cooled down to rt, diluted with water (4 mL) and extracted with EtOAc (3 mL, then twice with 1 mL). The organic layers were combined, washed with water (three times, 1 mL) and evaporated to dryness in vacuo. The resulting residue was dissolved in 1:1 MeOH/EtOAc (3 mL) and passed through a Thiol StratoSphere™ SPE cartridge (Polymer Labs). The solution was evaporated to dryness in vacuo to give the crude product as brown solid. LR-MS (API-ES): calculated for C$_{14}$H$_9$ClN$_2$O$_2$ 272.1, observed m/e 273.0 (M+H)$^+$ (R$_t$ 3.40 min). The crude product was used in the next step without further purification.

Step B.
4-Chloro-5-phenylethynyl-benzene-1,2-diamine (1-2)

A 2 mL Biotage™ microwave vial was charged with Fe (67.0 mg, 1.19 mmol), a solution of compound 1-1 (65.0 mg, 0.238 mmol) in EtOH (2 mL) and an aqueous solution of NH$_4$Cl (6.38 mg, 0.119 mmol in 0.5 mL of water). The resulting suspension was heated in a microwave synthesizer (Biotage Initiator™) at 140° C. for 10 min. The mixture was then filtered and the remaining solids were washed with EtOAc (three times, 2 mL). The filtrate and washes were combined and evaporated to dryness in vacuo to give the crude product as brown solid. LR-MS (API-ES): calculated for C$_{14}$H$_{11}$ClN$_2$ 242.1, observed m/e 243.0 (M+H)$^+$ (R$_t$ 2.91 min). The crude product was used in the next step without further purification.

Step C. 5-Chloro-6-phenylethynyl-1,3-dihydro-benzoimidazole-2-thione (1-3)

A 2 mL Biotage™ microwave vial was charged with solid KOH (19.4 mg, 0.345 mmol), water (0.2 mL), a solution of compound 1-2 (55.8 mg, 0.230 mmol) in EtOH (1.2 mL) and carbon disulfide (69 uL, 1.2 mmol). The vial was capped and stirred at rt until KOH dissolved, and then heated in a microwave synthesizer (Biotage Initiator™) at 110° C. for 10 min. Contents of the vial were transferred to a 20 mL scintillation vial, diluted with water (8 mL) and acidified by the dropwise addition of 10% aqueous AcOH. The resulting suspension was centrifuged, the supernatant was decanted and the resulting brownish precipitate was washed with 10% aqueous AcOH (3 mL) and water (three times 3 mL). The precipitate was dissolved in EtOAc and passed through a short plug of neutral alumina. The EtOAc solution was evaporated to dryness in vacuo to give the crude product as brownish solid. LR-MS (API-ES): calculated for C$_{15}$H$_9$ClN$_2$S 284.0, observed m/e 285.0 (M+H)$^+$. (R$_t$ 2.94 min). The crude product was used in the next step without further purification.

Step D. (6-Chloro-5-phenylethynyl-1H-benzoimidazol-2-ylsulfanyl)-acetic acid (1-4)

A solution of bromoacetic acid (47.8 mg, 0.344 mmol) in EtOH (1 mL) was added dropwise to a 20 mL scintillation vial equipped with a stirring bar and a septum cap containing a solution of compound 1-3 (49.0 mg, 0.172 mmol) in EtOH (1 mL). To this solution, 1M KOH (2 mL) was added dropwise, and the resulting mixture was stirred at rt for 1 h. The reaction mixture was then diluted with water (4 mL) and acidified with 10% aqueous HCl. The solution was extracted with EtOAc (3 mL then twice 1 mL), extracts were combined and evaporated to dryness in vacuo. The resulting oily residue was dissolved in DMSO (1.0 mL), filtered and purified by reverse-phase HPLC to give the title compound as white solid. LR-MS (API-ES): calculated for C$_{17}$H$_{11}$ClN$_2$O$_2$S 342.0, observed m/e 343.1 (M+H)$^+$ (R$_t$ 7.71 min).

Example 2

(5-Biphenyl-4-yl-6-chloro-1H-benzoimidazol-2-ylsulfanyl)-acetic acid

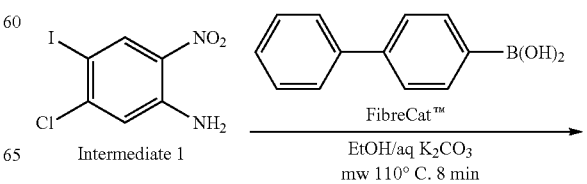

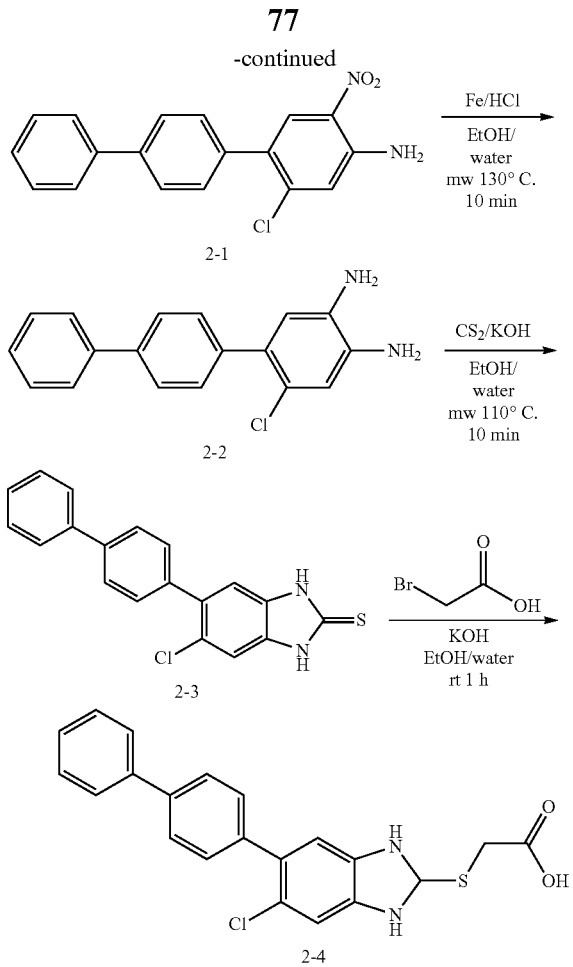

Step A. 2-Chloro-5-nitro-[1,1';4',1"]terphenyl-4-ylamine (2-1)

A 5 mL Biotage™ microwave vial was charged with FibreCat™ (Aldrich, 0.4 mmol/g; 37.5 mg, 3 mol %) and biphenyl-4-boronic acid (119.0 mg, 0.600 mmol). A solution of 5-chloro-4-iodo-2-nitro-phenylamine (Intermediate 1, 149.0 mg, 0.500 mmol) in EtOH (4.4 mL) was added followed by 1M aqueous $K_2CO_3$ (0.6 mL). The vial was heated in a microwave synthesizer (Biotage Initiator™) at 110° C. for 8 min. Contents of the vial were diluted with EtOAc (2 mL) and filtered. The resulting precipitate was washed with EtOAc (three times, 2 mL). The filtrate and washes were combined and evaporated to dryness in vacuo. The residue was dissolved in EtOAc (4 mL), washed with 1M aqueous $K_2CO_3$ (twice, 1 mL) and evaporated to dryness in vacuo to give an orange-yellow solid. LR-MS (API-ES): calculated for $C_{18}H_{13}ClN_2O_2$ 324.1, observed m/e 367.2 (100%), 347.0 ((M+Na)$^+$, 325.0 (M+H)$^+$, ($R_t$ 3.56 min). The crude product was used in the next step without further purification.

Step B. 6-Chloro-[1,1';4',1"]terphenyl-3,4-diamine (2-2)

A 5 mL Biotage™ microwave vial was charged with Fe (285.0 mg, 5.11 mmol), a solution of compound 2-1 (166.0 mg, 0.511 mmol) in EtOH (3 mL) and diluted aqueous HCl (82 uL of 37% aqueous HCl, diluted with 0.75 mL of water). The resulting suspension was heated in a microwave synthesizer (Biotage Initiator™) at 130° C. for 10 min. The mixture was then filtered and the remaining solids were washed with EtOAc (three times, 2 mL). The filtrate and washes were combined and evaporated to dryness in vacuo. The residue was dissolved in 3:1 EtOAc/TEA and passed through a short plug of a neutral alumina. The resulting solution was evaporated to dryness in vacuo to give the crude product as brownish oil. LR-MS (API-ES): calculated for $C_{18}H_{15}ClN_2$ 294.1, observed m/e 295.0 (M+H)$^+$ ($R_t$ 3.07 min). The crude product was used in the next step without further purification.

Step C. 5-Biphenyl-4-yl-6-chloro-1,3-dihydro-benzoimidazole-2-thione (2-3)

A 2 mL Biotage™ microwave was charged with solid KOH (18.0 mg, 0.326 mmol), water (0.2 mL), a solution of compound 2-2 (64.0 mg, 0.217 mmol) in EtOH (1.2 mL) and carbon disulfide (65 uL, 1.1 mmol). The vial was capped and stirred at rt until KOH dissolved then heated in a microwave synthesizer (Biotage Initiator™) at 110° C. for 10 min. Contents of the vial were transferred to a 20 mL scintillation vial, diluted with water (6 mL) and acidified by a dropwise addition of 10% aqueous AcOH. The resulting suspension was centrifuged, the supernatant was decanted and the resulting brownish precipitate was washed with 10% aqueous AcOH (3 mL) and water (three times, 3 mL). The precipitate was then dissolved in EtOAc and passed through a short plug of neutral alumina. The EtOAc solution was evaporated to dryness in vacuo to give the crude product as yellow solid. LR-MS (API-ES): calculated for $C_{19}H_{13}ClN_2S$ 336.1, observed m/e 337.0 (M+H)$^+$ ($R_t$ 3.12 min). The crude product was used in the next step without further purification.

Step D. (5-Biphenyl-4-yl-6-chloro-1H-benzoimidazol-2-ylsulfanyl)-acetic acid (2-4)

A solution of bromoacetic acid (43.4 mg, 0.312 mmol) in EtOH (1 mL) was added dropwise to a 20 mL scintillation vial equipped with a stirring bar and a septum cap containing a solution of compound 2-3 (52.6 mg, 0.156 mmol) in EtOH (0.5 mL). To this solution, 1M KOH (1.5 mL) was added dropwise, and the resulting mixture was stirred at rt for 1 h. The reaction mixture was then diluted with water (4 mL) and acidified with 10% aqueous HCl. The solution was extracted with EtOAc (3 mL, then three times 1 mL). Extracts were combined and evaporated to dryness in vacuo. The resulting oily residue was dissolved in DMSO (1 mL), filtered and purified by reverse-phase HPLC with to give the title compound as white solid. $^1$H NMR (DMSO-$d_6$, 400 MHz) δ 7.70-7.76 (4H, m), 7.64 (1H, s), 7.46-7.55 (4H, m), 7.45 (1H, s), 7.36-7.40 (1H, m), 4.12 (2H, s); LRMS (API-ES): calculated for $C_{21}H_{15}ClN_2O_2S$ 394.1, observed m/e 395.0 (M+H)$^+$ ($R_t$ 3.14 min).

Scheme 1

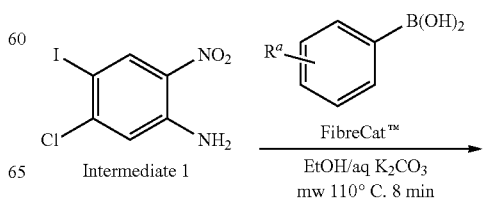

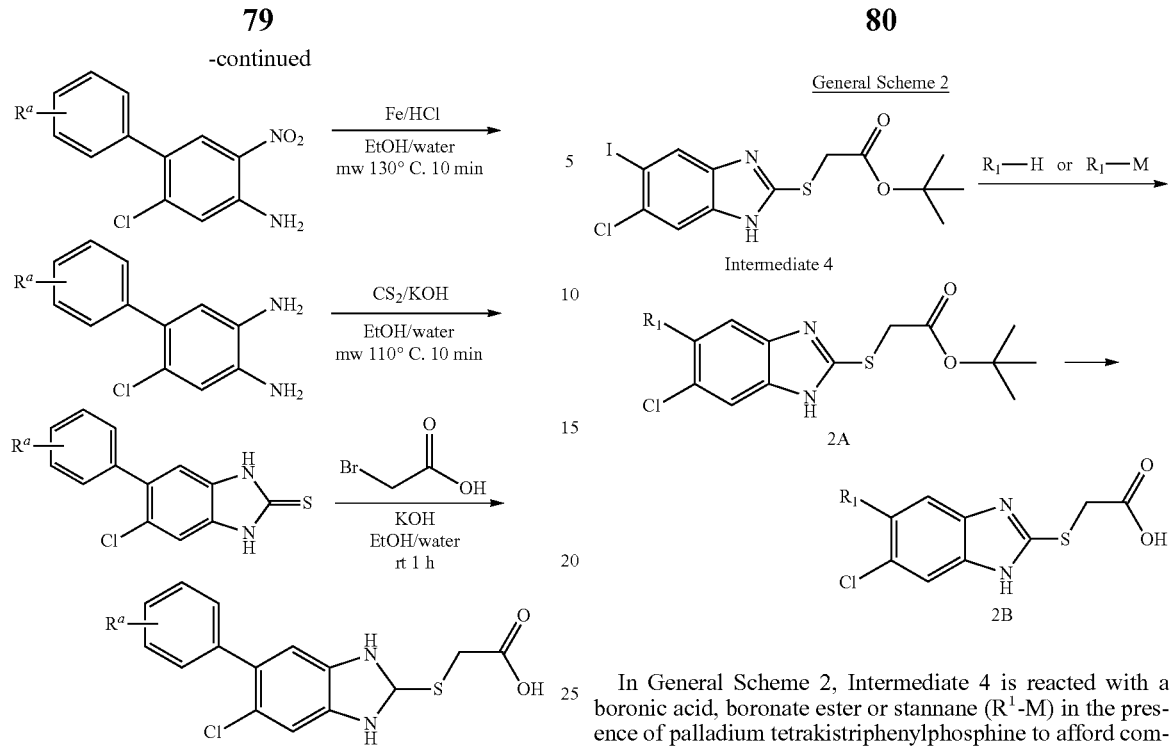

In General Scheme 2, Intermediate 4 is reacted with a boronic acid, boronate ester or stannane ($R^1$-M) in the presence of palladium tetrakistriphenylphosphine to afford compound 2A. Alternatively, Intermediate 4 is reacted with an acetylene ($R^1$—H) in the presence of copper (I) iodide and

TABLE 1

Examples 3-5 in Table 1 were prepared following the procedures described in Example 2 and Scheme 1 by substituting biphenyl-4-boronic acid with the appropriate boronic acid or ester.

| Example No | Name | Structure | Formula/ Calculated | LCMS (M + H)+ |
|---|---|---|---|---|
| 3 | (5-1,3-benzo-dioxol-5-yl-6-chloro-1H-benzimidazol-2-ylsulfanyl)-acetic acid | 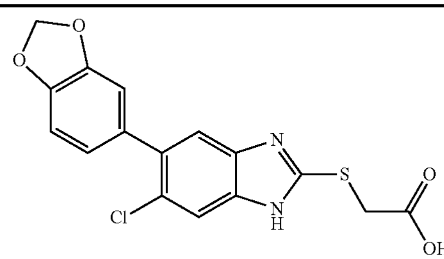 | $C_{16}H_{11}ClN_2O_4S$ 362.01 | 362.9 |
| 4 | [6-chloro-5-(3-fluoro-phenyl)-1H-benzimidazol-2-ylsulfanyl]-acetic acid | 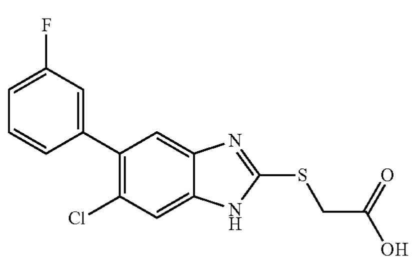 [SMILES: O=C(O)CSc1nc2cc(-c3cccc(F)c3)c(Cl)cc2[nH]1] | $C_{15}H_{10}ClFN_2O_2S$ 336.01 | 336.9 |
| 5 | [6-chloro-5-(3,5-difluoro-phenyl)-1H-benzimidazol-2-ylsulfanyl]-acetic acid | 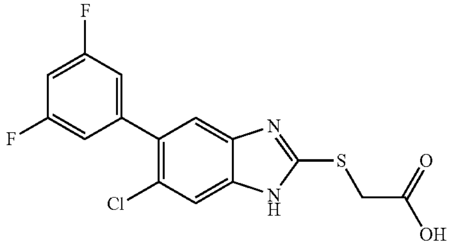 [SMILES: O=C(O)CSc1nc2cc(-c3cc(F)cc(F)c3)c(Cl)cc2[nH]1] | $C_{15}H_9ClF_2N_2O_2S$ 354.00 | 355.0 |

Example 6

2-(6-chloro-5-(2'-hydroxybiphenyl-4-yl)-1H-benzo[d]imidazol-2-ylthio)acetic acid

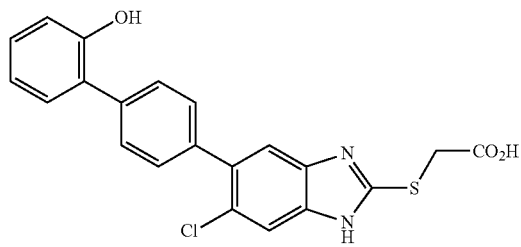 [SMILES: O=C(O)CSc1nc2cc(-c3ccc(-c4ccccc4O)cc3)c(Cl)cc2[nH]1]

Step A tert-butyl 2-(6-chloro-5-(2'-hydroxybiphenyl-4-yl)-1H-benzo[d]imidazol-2-ylthio)acetate A solution of potassium carbonate (1 M solution in water, 0.15 mL, 0.15 mmol), Pd(PPh$_3$)$_4$ (3 mg, 0.0002 mmol), 4'-(4,4,5,5-tetramethyl-1,3,2-dioxaborolan-2-yl)biphenyl-2-ol (15 mg, 0.05 mmol) and Intermediate 4 (21 mg, 0.05 mmol) in dioxane (0.25 mL) was heated at 80° C. for 15 h. The aqueous phase was removed and the organic phase was concentrated, diluted with EtOAc, filtered and concentrated to afford the desired product as a solid, which was used in the next step without further purification.

Step B 2-(6-chloro-5-(2'-hydroxybiphenyl-4-yl)-1H-benzo[d]imidazol-2-ylthio)acetic acid A solution of tert-butyl 2-(6-chloro-5-(2'-hydroxybiphenyl-4-yl)-1H-benzo[d]imidazol-2-ylthio)acetate in TFA (0.9 mL) and water (0.1 mL) was stirred at room temperature for 2 h and concentrated. The resultant solid was purified with HPLC to afford the desired product. LCMS: calculated for C$_{21}$H$_{15}$ClN$_2$O$_3$S 410.05, observed m/e 411.0 (M+H)$^+$.

TABLE 2

Examples 7-17 in Table 2 were prepared following the procedures described in Example 6 and General Scheme 2 by substituting the appropriate boronic acid, boronate ester, stannane or acetylene from the Intermediates, or from commercial sources; and followed by subsequent ester hydrolysis.

| Example. No. | Name | Structure | HPLC-mass spectrum m/e |
|---|---|---|---|
| 7 | 2-(6-(4-(acetamido-methyl)phenyl)-5-chloro-1H-benzo[d]-imidazol-2-ylthio)-acetic acid | 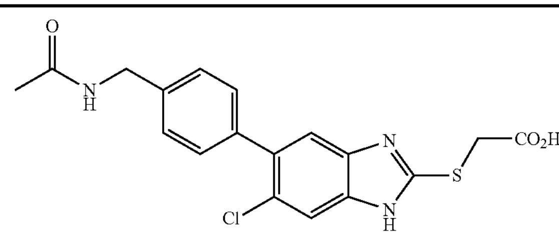 | 390 |
| 8 | 2-(6-chloro-5-(4-hydroxyphenyl)-1H-benzo[d]imidazol-2-ylthio)acetic acid | 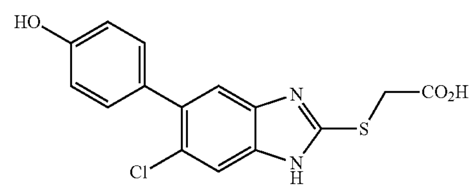 [SMILES: O=C(O)CSc1nc2cc(-c3ccc(O)cc3)c(Cl)cc2[nH]1] | 335 |
| 9 | 2-(6-chloro-5-(4-(hydroxymethyl)phenyl)-1H-benzo[d]-imidazol-2-ylthio)-acetic acid | 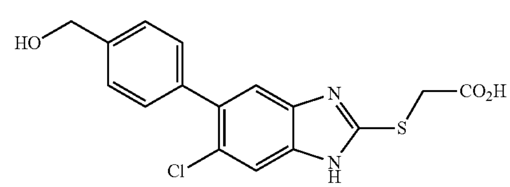 [SMILES: O=C(O)CSc1nc2cc(-c3ccc(CO)cc3)c(Cl)cc2[nH]1] | 349 |
| 10 | 2-(5-((2-amino-phenyl)ethynyl)-6-chloro-1H-benzo[d]-imidazol-2-ylthio)-acetic acid | 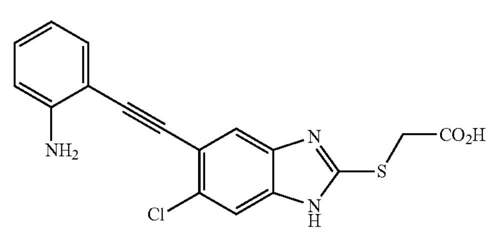 [SMILES: Nc1ccccc1C#Cc1cc2nc(SCC(=O)O)[nH]c2cc1Cl] | |

TABLE 2-continued

Examples 7-17 in Table 2 were prepared following the procedures described in Example 6 and General Scheme 2 by substituting the appropriate boronic acid, boronate ester, stannane or acetylene from the Intermediates, or from commercial sources; and followed by subsequent ester hydrolysis.

| Example. No. | Name | Structure | HPLC-mass spectrum m/e |
|---|---|---|---|
| 11 | 2-(6-chloro-5-(1H-indazol-6-yl)-1H-benzo[d]imidazol-2-ylthio)acetic acid | 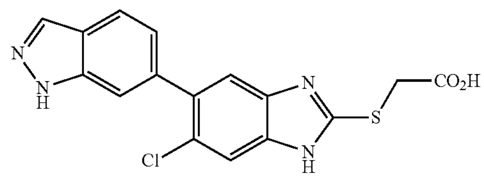 [SMILES: O=C(O)CSc1nc2cc(-c3ccc4cn[nH]c4c3)c(Cl)cc2[nH]1] | 359 |
| 12 | 2-(6-chloro-5-(6-methoxypyridin-3-yl)-1H-benzo[d]imidazol-2-ylthio)acetic acid | 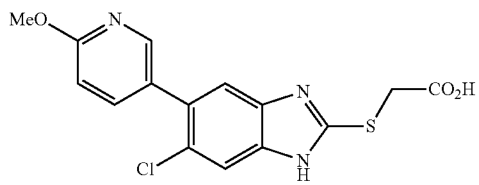 [SMILES: COc1ccc(-c2cc3nc(SCC(=O)O)[nH]c3cc2Cl)cn1] | 350 |
| 13 | 2-(5-(benzofuran-2-yl)-6-chloro-1H-benzo[d]imidazol-2-ylthio)acetic acid | 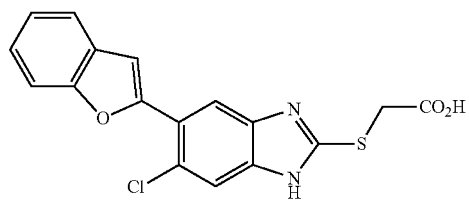 [SMILES: O=C(O)CSc1nc2cc(-c3cc4ccccc4o3)c(Cl)cc2[nH]1] | 359 |
| 14 | 2-(5-(benzo[b]-thiophen-3-yl)-6-chloro-1H-benzo[d]-imidazol-2-ylthio)-acetic acid | 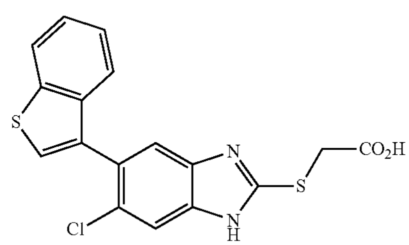 [SMILES: O=C(O)CSc1nc2cc(-c3csc4ccccc34)c(Cl)cc2[nH]1] | 375 |
| 15 | 2-(5-(4-(1H-pyrazol-1-yl)phenyl)-6-chloro-1H-benzo[d]imidazol-2-ylthio)acetic acid | 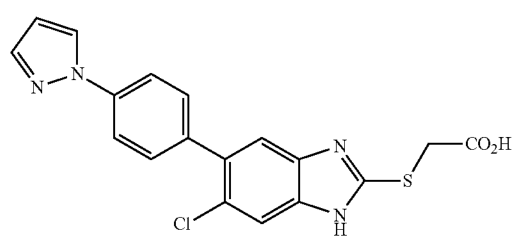 [SMILES: O=C(O)CSc1nc2cc(-c3ccc(-n4cccn4)cc3)c(Cl)cc2[nH]1] | 385 |
| 16 | 2-(5-(4-(1H-pyrazol-5-yl)phenyl)-6-chloro-1H-benzo[d]imidazol-2-ylthio)acetic acid | 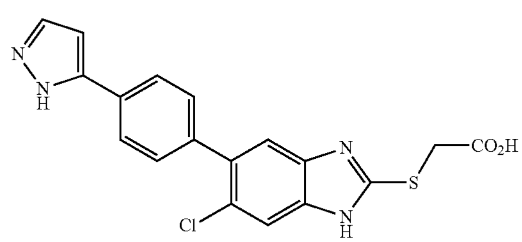 [SMILES: O=C(O)CSc1nc2cc(-c3ccc(-c4ccn[nH]4)cc3)c(Cl)cc2[nH]1] | 385 |

TABLE 2-continued

Examples 7-17 in Table 2 were prepared following the procedures described in Example 6 and General Scheme 2 by substituting the appropriate boronic acid, boronate ester, stannane or acetylene from the Intermediates, or from commercial sources; and followed by subsequent ester hydrolysis.

| Example. No. | Name | Structure | HPLC-mass spectrum m/e |
|---|---|---|---|
| 17 | 2-(5-((3-acetamido-phenyl)ethynyl)-6-chloro-1H-benzo[d]-imidazol-2-ylthio)-acetic acid | 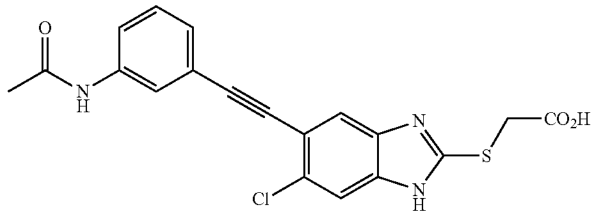 [SMILES: CC(=O)Nc1cccc(C#Cc2cc3nc(SCC(=O)O)[nH]c3cc2Cl)c1] | 400 |

Example 18

[6-Chloro-5-(4-hydroxymethyl-phenylethynyl)-1H-benzoimidazol-2-ylsulfanyl]-acetic acid

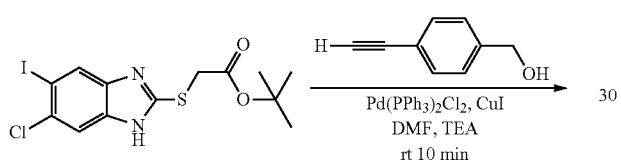

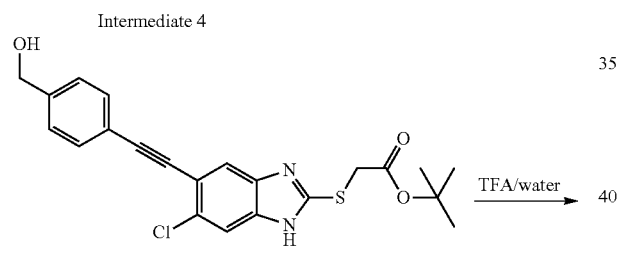

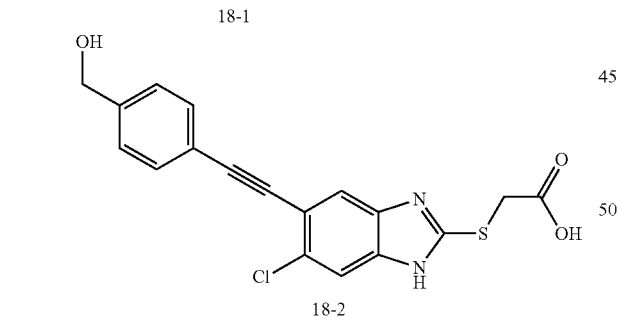

Step A. [6-Chloro-5-(4-hydroxymethyl-phenylethynyl)-1H-benzoimidazol-2-ylsulfanyl]-acetic acid tert-butyl ester (18-1)

A 2 mL Biotage™ microwave vial was charged with copper iodide (1.1 mg, 10 mol %), and Pd(PPh$_3$)$_2$Cl$_2$ (2.1 mg, 5 mol %). A solution of (6-chloro-5-iodo-1H-benzoimidazol-2-ylsulfanyl)-acetic acid tert-butyl ester (Intermediate 4, 25.0 mg, 0.059 mmol) in DMF (0.5 mL) was added to the vial, followed by a solution of (4-ethynyl-phenyl)-methanol (15.0 mg, 0.118 mmol) in DMF (250 uL) and TEA (57 uL, 0.41 mmol). The resulting suspension was heated in a microwave synthesizer (Biotage Initiator™) at 120° C. for 5 min. The solvent was removed in vacuo to give dark brown oil which was used in the next step without further purification. LR-MS (API-ES): calculated for C$_{22}$H$_{21}$ClN$_2$O$_3$S 428.1, observed m/e 429.0 (M+H)$^+$ (R$_t$ 3.05 min).

Step B. [6-Chloro-5-(4-hydroxymethyl-phenylethynyl)-1H-benzoimidazol-2-ylsulfanyl]-acetic acid (18-2)

In a 4 mL vial, compound 18-1 (25.3 mg, 0.059 mmol) was dissolved in 9:1 TFA/water (2 mL) and stirred at rt for 2 h. The solution was evaporated to dryness in vacuo to give oily brown residue, which was dissolved in DMSO (1.25 mL), filtered and purified by reverse-phase HPLC to give the title compound. LR-MS (API-ES): calculated for C$_{18}$H$_{13}$ClN$_2$O$_3$S 372.0, observed m/e 372.9 (M+H)$^+$ (R$_t$ 1.87 min).

Scheme 2A

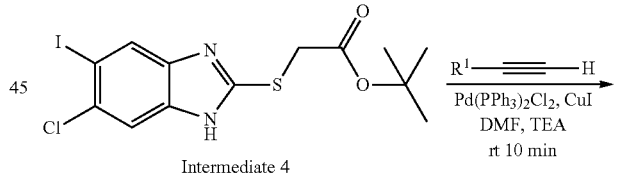

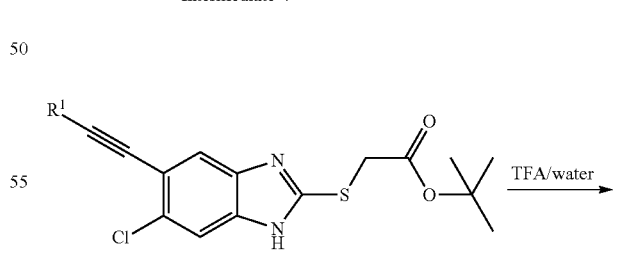

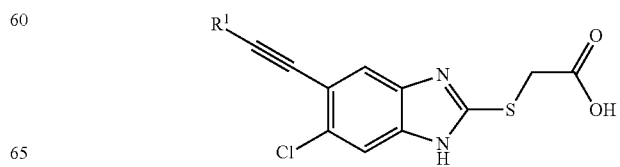

TABLE 3

Examples 19-32 in Table 3 were prepared following the procedures described in Example 18 and Scheme 2A by substituting (4-ethynyl-phenyl)-methanol with the appropriate terminal acetylene.

| Example No | Name | Structure | Formula/ Calculated | LCMS (M + H)+ |
|---|---|---|---|---|
| 19 | [6-chloro-5-(4-methanesulfonyl-phenyl-ethynyl)-1H-benzo-imidazol-2-yl-sulfanyl]-acetic acid | 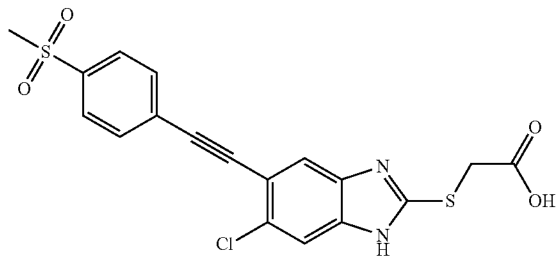 [SMILES: CS(=O)(=O)c1ccc(C#Cc2cc3nc(SCC(=O)O)[nH]c3cc2Cl)cc1] | $C_{18}H_{13}ClN_2O_4S_2$ 420.00 | 420.9 |
| 20 | [6-chloro-5-(2-cyano-phenyl-ethynyl)-1H-benzo-imidazol-2-ylsulfanyl]-acetic acid | 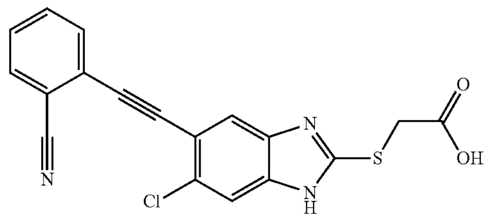 [SMILES: N#Cc1ccccc1C#Cc1cc2nc(SCC(=O)O)[nH]c2cc1Cl] | $C_{18}H_{10}ClN_3O_2S$ 367.02 | 368.0 |
| 21 | (6-chloro-5-piperidin-4-ylethynyl-1H-benzoimidazol-2-ylsulfanyl)-acetic acid | 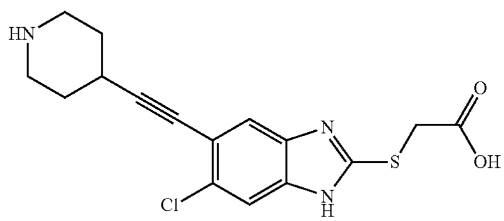 [SMILES: O=C(O)CSc1nc2cc(C#CC3CCNCC3)c(Cl)cc2[nH]1] | $C_{16}H_{16}ClN_3O_2S$ 349.07 | 350.0 |
| 22 | 6-chloro-5-(4-fluoro-phenyl-ethynyl)-1H-benzoimidazol-2-ylsulfanyl]-acetic acid | 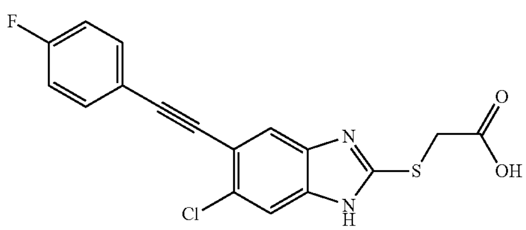 [SMILES: O=C(O)CSc1nc2cc(C#Cc3ccc(F)cc3)c(Cl)cc2[nH]1] | $C_{17}H_{10}ClFN_2O_2S$ 360.01 | 360.9 |
| 23 | 6-chloro-5-(3-fluoro-phenyl-ethynyl)-1H-benzoimidazol-2-ylsulfanyl]-acetic acid | 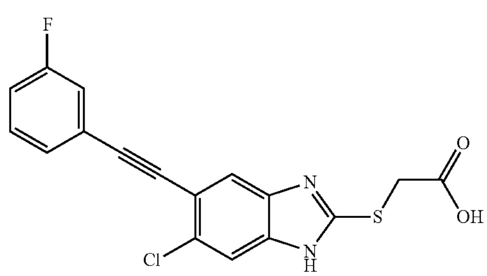 [SMILES: O=C(O)CSc1nc2cc(C#Cc3cccc(F)c3)c(Cl)cc2[nH]1] | $C_{17}H_{10}ClFN_2O_2S$ 360.01 | 360.9 |
| 24 | [6-chloro-5-(2,4-difluoro-phenyl-ethynyl)-1H-benzoimidazol-2-ylsulfanyl]-acetic acid | 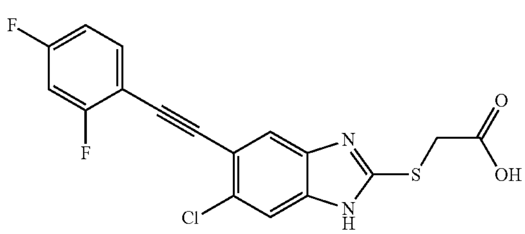 [SMILES: O=C(O)CSc1nc2cc(C#Cc3ccc(F)cc3F)c(Cl)cc2[nH]1] | $C_{17}H_9ClF_2N_2O_2S$ 378.00 | 378.9 |

TABLE 3-continued

Examples 19-32 in Table 3 were prepared following the procedures described in Example 18 and Scheme 2A by substituting (4-ethynyl-phenyl)-methanol with the appropriate terminal acetylene.

| Example No | Name | Structure | Formula/ Calculated | LCMS (M + H)+ |
|---|---|---|---|---|
| 25 | (6-chloro-5-pyridin-4-yl-ethynyl-1H-benzoimidazol-2-ylsulfanyl)-acetic acid | 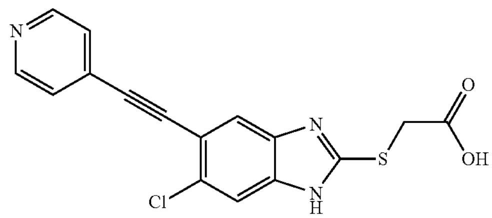 [SMILES: O=C(O)CSc1nc2cc(C#Cc3ccncc3)c(Cl)cc2[nH]1] | $C_{16}H_{10}ClN_3O_2S$ 343.02 | 344.0 |
| 26 | [6-chloro-5-(3-phenoxy-prop-1-ynyl)-1H-benzo-imidazol-2-yl-sulfanyl]-acetic acid | 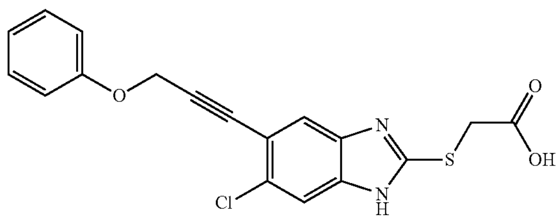 [SMILES: O=C(O)CSc1nc2cc(C#CCOc3ccccc3)c(Cl)cc2[nH]1] | $C_{18}H_{13}ClN_2O_3S$ 372.03 | 372.9 |
| 27 | 6-chloro-5-(2-fluoro-phenyl-ethynyl)-1H-benzoimidazol-2-ylsulfanyl]-acetic acid | 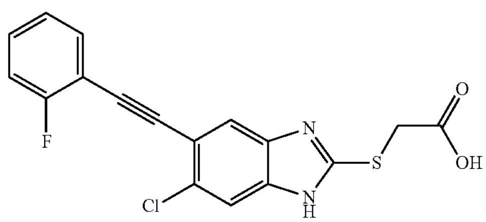 [SMILES: O=C(O)CSc1nc2cc(C#Cc3ccccc3F)c(Cl)cc2[nH]1] | $C_{17}H_{10}ClFN_2O_2S$ 360.01 | 360.9 |
| 28 | [6-chloro-5-(4-cyano-phenyl-ethynyl)-1H-benzoimidazol-2-ylsulfanyl]-acetic acid | 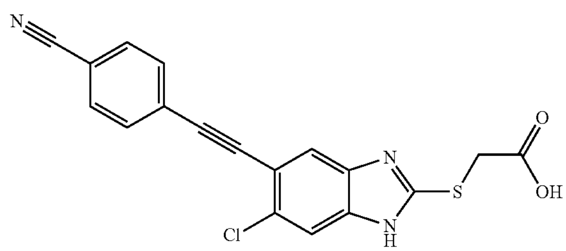 [SMILES: N#Cc1ccc(C#Cc2cc3nc(SCC(=O)O)[nH]c3cc2Cl)cc1] | $C_{18}H_{10}ClN_3O_2S$ 367.02 | 368.0 |
| 29 | [6-chloro-5-(3-hydroxyphenyl-ethynyl)-1H-benzoimidazol-2-ylsulfanyl]-acetic acid | 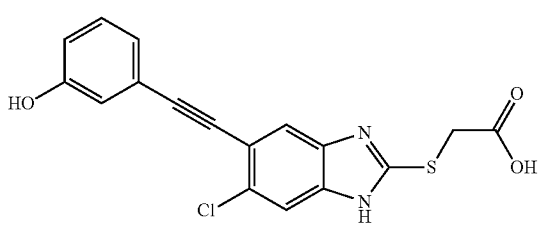 [SMILES: O=C(O)CSc1nc2cc(C#Cc3cccc(O)c3)c(Cl)cc2[nH]1] | $C_{17}H_{11}ClN_2O_3S$ 358.02 | 359.0 |
| 30 | (6-chloro-5-o-tolylethynyl-1H-benzo-imidazol-2-ylsulfanyl)-acetic acid | 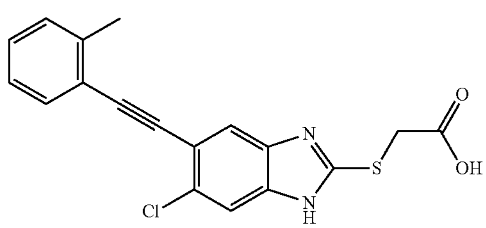 [SMILES: Cc1ccccc1C#Cc1cc2nc(SCC(=O)O)[nH]c2cc1Cl] | $C_{18}H_{13}ClN_2O_2S$ 356.04 | 357.0 |

TABLE 3-continued

Examples 19-32 in Table 3 were prepared following the procedures described in Example 18 and Scheme 2A by substituting (4-ethynyl-phenyl)-methanol with the appropriate terminal acetylene.

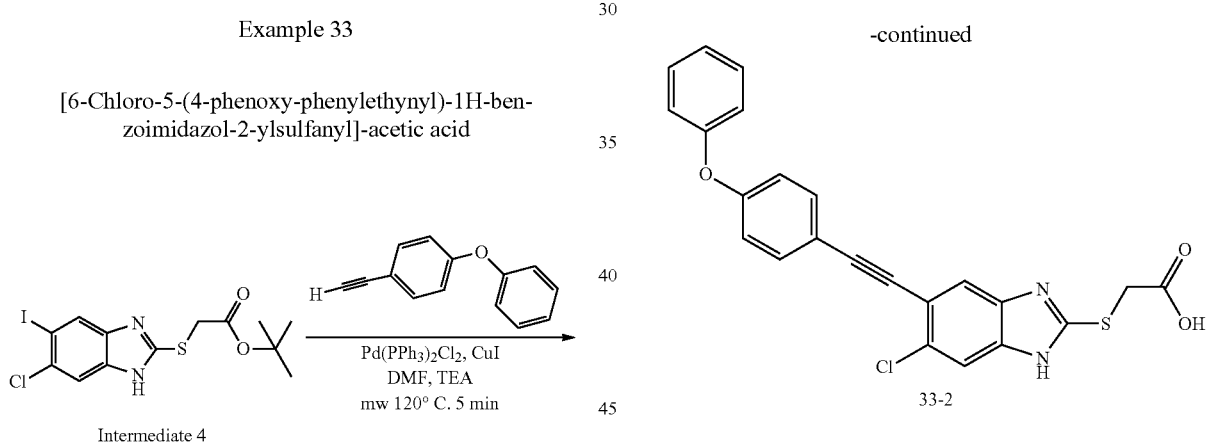

| Example No | Name | Structure | Formula/ Calculated | LCMS (M + H)+ |
|---|---|---|---|---|
| 31 | (6-chloro-5-m-tolylethynyl-1H-benzoimidazol-2-ylsulfanyl)-acetic acid | 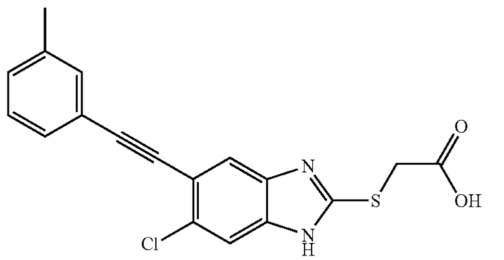 [SMILES: Cc1cccc(C#Cc2cc3nc(SCC(=O)O)[nH]c3cc2Cl)c1] | $C_{18}H_{13}ClN_2O_2S$ 356.04 | 357.0 |
| 32 | [6-chloro-5-(3-methoxy-phenyl-ethynyl)-1H-benzoimidazol-2-ylsulfanyl]-acetic acid | 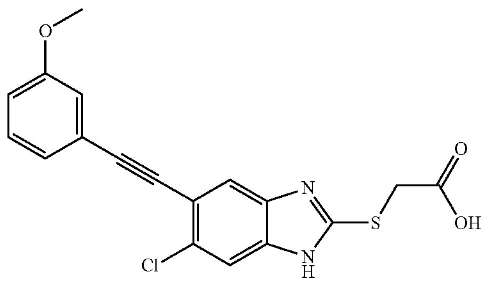 [SMILES: COc1cccc(C#Cc2cc3nc(SCC(=O)O)[nH]c3cc2Cl)c1] | $C_{18}H_{13}ClN_2O_3S$ 372.03 | 372.9 |

Example 33

[6-Chloro-5-(4-phenoxy-phenylethynyl)-1H-benzoimidazol-2-ylsulfanyl]-acetic acid

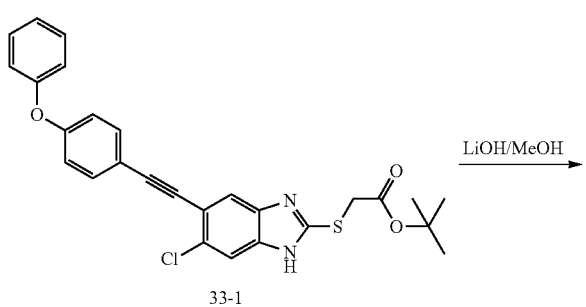

Step A. [6-Chloro-5-(4-phenoxy-phenylethynyl)-1H-benzoimidazol-2-ylsulfanyl]-acetic acid tert-butyl ester (33-1)

A 2 mL Biotage™ microwave vial equipped with a stirring bar was charged with copper iodide (1.1 mg, 10 mol %), and Pd(PPh₃)₂Cl₂ (2.1 mg, 5 mol %). A solution of (6-chloro-5-iodo-1H-benzoimidazol-2-ylsulfanyl)-acetic acid tert-butyl ester (Intermediate 4, 25.0 mg, 0.059 mmol) in DMF (0.5 mL) was added to the vial, followed by a solution of 1-ethynyl-4-phenoxy-benzene (15.0 mg, 0.118 mmol) in DMF (250 uL) and TEA (57 uL, 0.41 mmol). The resulting suspension was heated in a microwave synthesizer (Biotage Initiator™) at 120° C. for 5 min. The solvent was removed in vacuo to give dark brown oil which was re-dissolved in a 1:1 MeOH/EtOAc mixture (3 mL) and passed through a Thiol StratoSphere™ SPE cartridge (Polymer Labs). The resulting solution was evaporated to dryness in vacuo to give the crude product as brown solid. LR-MS (API-ES): calculated for $C_{27}H_{23}ClN_2O_3S$ 490.1, observed m/e 491.0 (M+H)$^+$ ($R_t$ 3.74 min). The crude product was used in the next step without further purification.

Step B. [6-Chloro-5-(4-phenoxy-phenylethynyl)-1H-benzoimidazol-2-ylsulfanyl]acetic acid (33-2)

A solution of compound 33-1 (29.0 mg, 0.059 mmol) in MeOH (6 mL) was added to 5% aqueous LiOH (3 mL) and the mixture was stirred at rt for 20 h. The mixture was then diluted with water (2 mL), evaporated to ½ of the initial volume and acidified with 5% aqueous HCl. The solution was extracted with EtOAc (3 mL then 1 mL, twice). The organic layers were combined, washed with water (three times, 1 mL) and evaporated to dryness in vacuo. The resulting oily residue was dissolved in DMSO (1.0 mL), filtered and purified by reverse-phase HPLC to give the title compound as off-white solid. LR-MS (API-ES): calculated for $C_{23}H_{15}ClN_2O_3S$ 434.1, observed m/e 435.0 (M+H)$^+$ ($R_t$ 2.96 min).

Scheme 2B

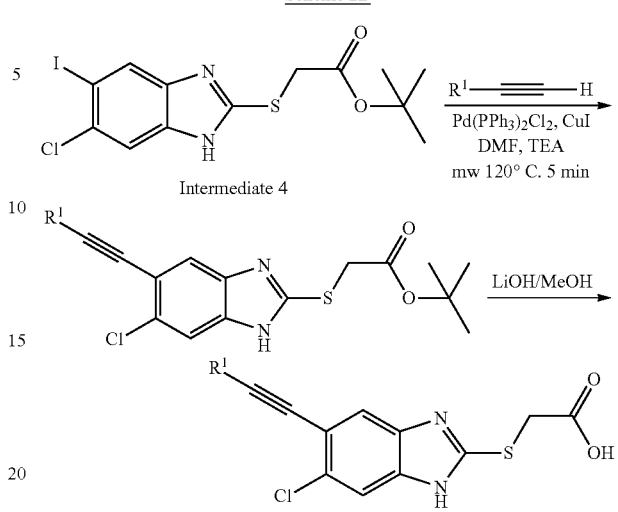

TABLE 4

Examples 34-39 in Table 4 were prepared following the procedures described in Example 33 and Scheme 2B by substituting 1-ethynyl-4-phenoxy-benzene with the appropriate terminal acetylene.

| Example No. | Name | Structure | Formula/ Calculated | LCMS (M + H)+ |
|---|---|---|---|---|
| 34 | (5-biphenyl-4-ylethynyl-6-chloro-1H-benzoimidazol-2-ylsulfanyl)-acetic acid | 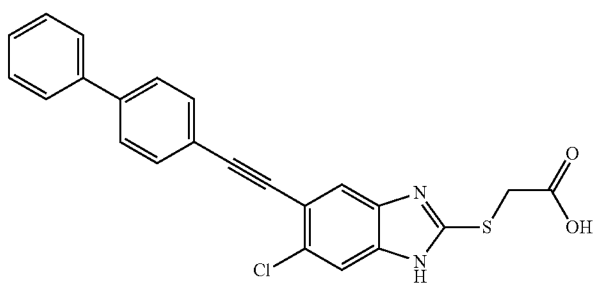 [SMILES: O=C(O)CSc1nc2cc(C#Cc3ccc(-c4ccccc4)cc3)c(Cl)cc2[nH]1] | $C_{23}H_{15}ClN_2O_2S$ 418.05 | 419 |
| 35 | (6-chloro-5-cyclo-pentylethynyl-1H-benzo-imidazol-2-yl-sulfanyl)-acetic acid | 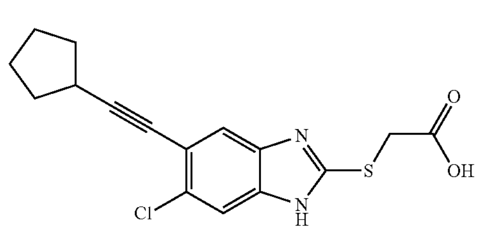 [SMILES: O=C(O)CSc1nc2cc(C#CC3CCCC3)c(Cl)cc2[nH]1] | $C_{16}H_{15}ClN_2O_2S$ 334.05 | 335 |
| 36 | [6-chloro-5-(4-ethyl-phenyl-ethynyl)-1H-benzo-imidazol-2-yl-sulfanyl]-acetic acid | 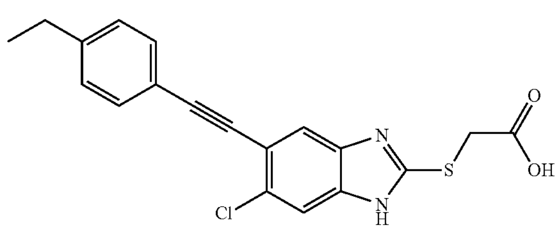 [SMILES: CCc1ccc(C#Cc2cc3nc(SCC(=O)O)[nH]c3cc2Cl)cc1] | $C_{19}H_{15}ClN_2O_2S$ 370.05 | 371 |

TABLE 4-continued

Examples 34-39 in Table 4 were prepared following the procedures described in Example 33 and Scheme 2B by substituting 1-ethynyl-4-phenoxy-benzene with the appropriate terminal acetylene.

| Example No. | Name | Structure | Formula/ Calculated | LCMS (M + H)+ |
|---|---|---|---|---|
| 37 | [6-chloro-5-(6-methoxy-naphthalen-2-yl-ethynyl)-1H-benzo-imidazol-2-yl-sulfanyl]-acetic acid | 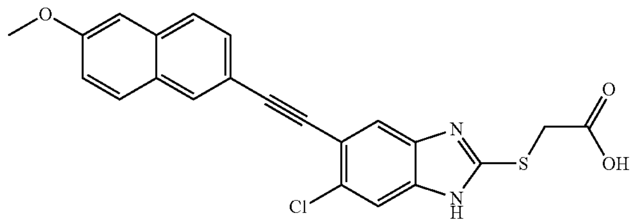 [SMILES: COc1ccc2cc(C#Cc3cc4nc(SCC(=O)O)[nH]c4cc3Cl)ccc2c1] | $C_{22}H_{15}ClN_2O_3S$ 422.05 | 423 |
| 38 | (6-chloro-5-thiophen-2-yl-ethynyl-1H-benzo-imidazol-2-yl-sulfanyl)-acetic acid | 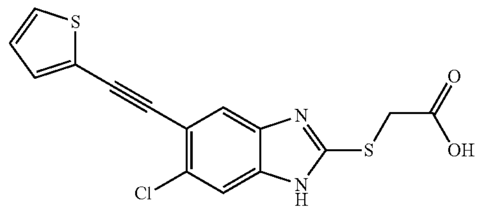 [SMILES: O=C(O)CSc1nc2cc(C#Cc3cccs3)c(Cl)cc2[nH]1] | $C_{15}H_9ClN_2O_2S_2$ 347.98 | 348.9 |
| 39 | [6-chloro-5-(4-methoxy-phenyl-ethynyl)-1H-benzimidazol-2-ylsulfanyl]-acetic acid | 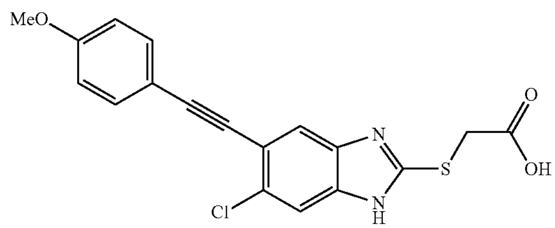 [SMILES: COc1ccc(C#Cc2cc3nc(SCC(=O)O)[nH]c3cc2Cl)cc1] | $C_{18}H_{13}ClN_2O_3S$ 372.03 | 372.9 |

Example 40

[5-(4-Benzyloxy-3-fluoro-phenyl)-6-chloro-1H-benzimidazol-2-ylsulfanyl]-acetic acid

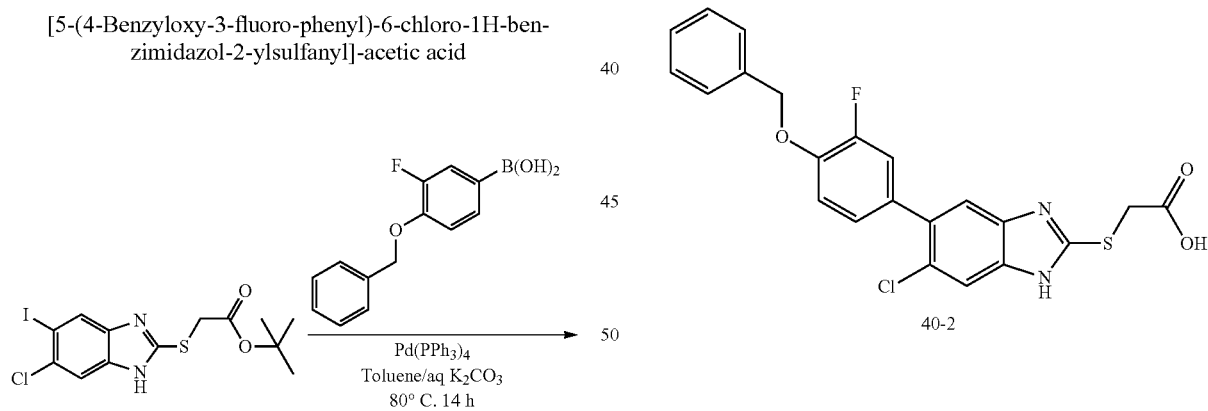

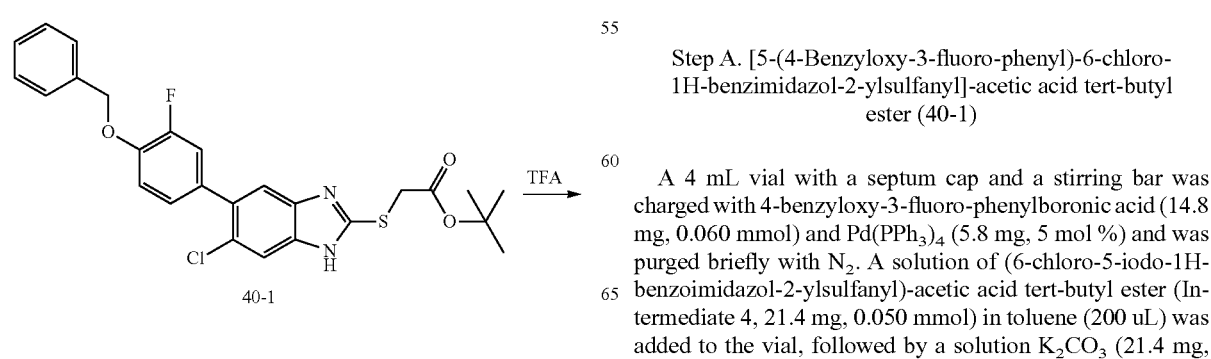

Step A. [5-(4-Benzyloxy-3-fluoro-phenyl)-6-chloro-1H-benzimidazol-2-ylsulfanyl]-acetic acid tert-butyl ester (40-1)

A 4 mL vial with a septum cap and a stirring bar was charged with 4-benzyloxy-3-fluoro-phenylboronic acid (14.8 mg, 0.060 mmol) and Pd(PPh₃)₄ (5.8 mg, 5 mol %) and was purged briefly with N₂. A solution of (6-chloro-5-iodo-1H-benzoimidazol-2-ylsulfanyl)-acetic acid tert-butyl ester (Intermediate 4, 21.4 mg, 0.050 mmol) in toluene (200 uL) was added to the vial, followed by a solution K₂CO₃ (21.4 mg, 0.050 mmol) in water (100 uL). The resulting mixture was stirred at 80° C. for 14 h. The mixture was allowed to cool down to rt, and was partitioned with EtOAc (1 mL) and 10% aqueous AcOH (1 mL). The organic layer was separated evaporated to dryness in vacuo. LR-MS (API-ES) of the residue confirmed the presence of the title compound: calculated for $C_{26}H_{24}ClFN_2O_3S$ 498.1, observed m/e 499.0 (M+H)$^+$ ($R_t$ 3.54 min). The crude product was used in the next step without further purification.

Step B. [5-(4-Benzyloxy-3-fluoro-phenyl)-6-chloro-1H-benzimidazol-2-ylsulfanyl]-acetic acid (40-2)

In a 4 mL vial, a solution of compound 40-1 (25.0 mg, 0.050 mmol) in 8:1 TFA/water (1 mL) was stirred at rt for 1 h. The mixture was then diluted with water (0.5 mL) and evaporated to dryness in vacuo. The resulting oily residue was dissolved in DMSO (1.0 mL), filtered and purified by reverse-phase HPLC to the title compound as a white solid. LR-MS (API-ES): calculated for $C_{22}H_{16}ClFN_2O_3S$ 442.1, observed m/e 443.0 (M+H)$^+$ ($R_t$ 3.10 min).

Scheme 2C

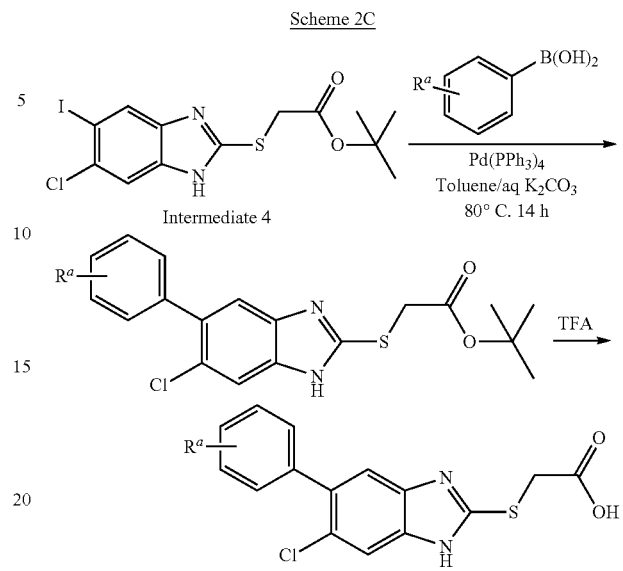

TABLE 5

Examples 41-44 in Table 5 were prepared following the procedures described in Example 40 and Scheme 2C by substituting 4-benzyloxy-3-fluoro-phenylboronic acid with the appropriate boronic acid or ester.

| Example No. | Name | Structure | Formula/ Calculated | LCMS (M + H)+ |
|---|---|---|---|---|
| 41 | [6-chloro-5-(4-chloro-phenyl)-1H-benzimidazol-2-ylsulfanyl]-acetic acid | 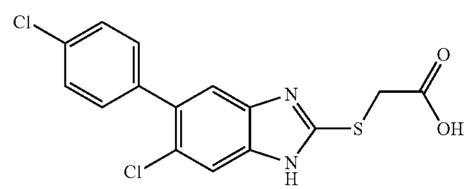 [SMILES: O=C(O)CSc1nc2cc(-c3ccc(Cl)cc3)c(Cl)cc2[nH]1] | $C_{15}H_{10}Cl_2N_2O_2S$ 351.98 | 353.0 |
| 42 | [6-chloro-5-(4-methoxy-phenyl)-1H-benzimidazol-2-ylsulfanyl]-acetic acid | 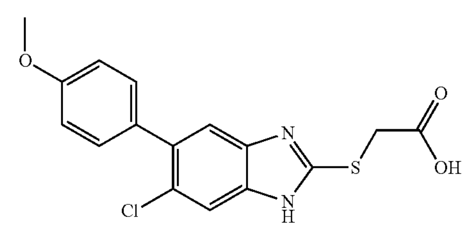 [SMILES: COc1ccc(-c2cc3nc(SCC(=O)O)[nH]c3cc2Cl)cc1] | $C_{16}H_{13}ClN_2O_3S$ 348.03 | 349.0 |
| 43 | [6-chloro-5-(4-isobutyl-phenyl)-1H-benzimidazol-2-ylsulfanyl]-acetic acid | 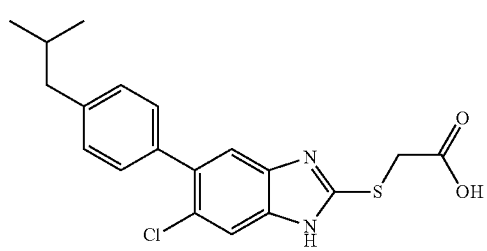 [SMILES: CC(C)Cc1ccc(-c2cc3nc(SCC(=O)O)[nH]c3cc2Cl)cc1] | $C_{19}H_{19}ClN_2O_2S$ 374.09 | 375.0 |

TABLE 5-continued

Examples 41-44 in Table 5 were prepared following the procedures described in Example 40 and Scheme 2C by substituting 4-benzyloxy-3-fluoro-phenylboronic acid with the appropriate boronic acid or ester.

| Example No. | Name | Structure | Formula/ Calculated | LCMS (M + H)+ |
|---|---|---|---|---|
| 44 | [5-(4-benzyl-oxy-phenyl)-6-chloro-1H-benzimidazol-2-ylsulfanyl]-acetic acid | 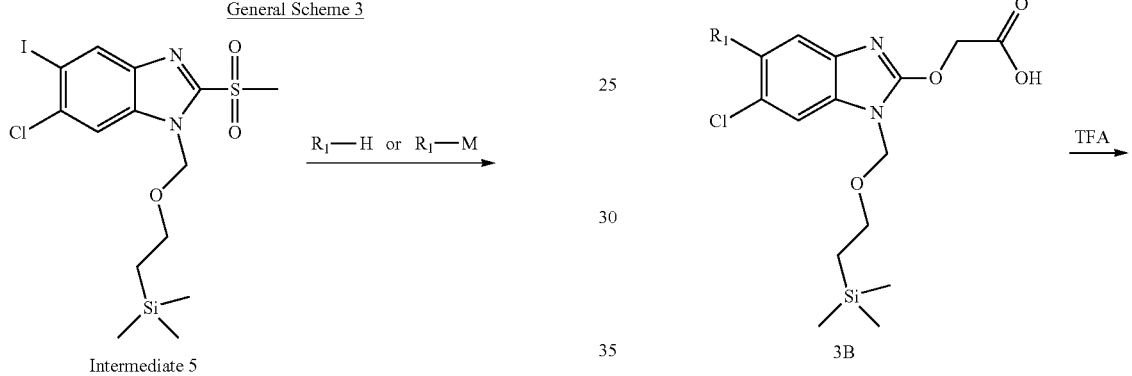 | $C_{22}H_{17}ClN_2O_3S$ 424.06 | 425.0 |

General Scheme 3

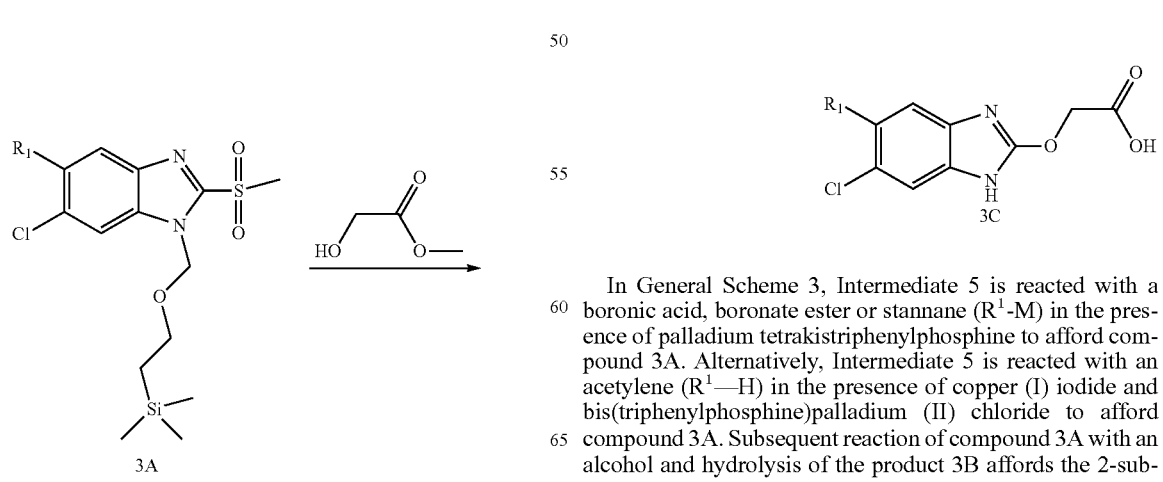

In General Scheme 3, Intermediate 5 is reacted with a boronic acid, boronate ester or stannane ($R^1$-M) in the presence of palladium tetrakistriphenylphosphine to afford compound 3A. Alternatively, Intermediate 5 is reacted with an acetylene ($R^1$—H) in the presence of copper (I) iodide and bis(triphenylphosphine)palladium (II) chloride to afford compound 3A. Subsequent reaction of compound 3A with an alcohol and hydrolysis of the product 3B affords the 2-substituted benzimidazole 3C.

Example 45
{6-Chloro-5-[4-(2H-pyrazol-3-yl)-phenyl]-1H-benzoimidazol-2-yloxy}-acetic acid
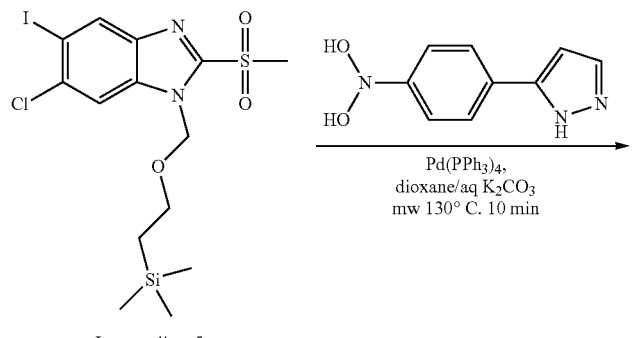
Intermediate 5
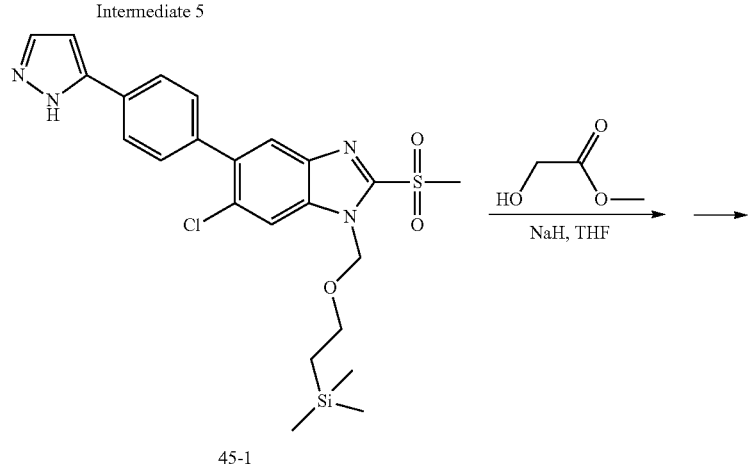
45-1
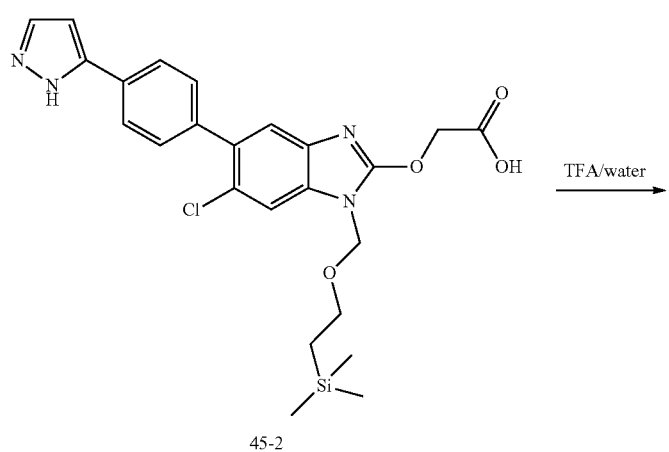
45-2
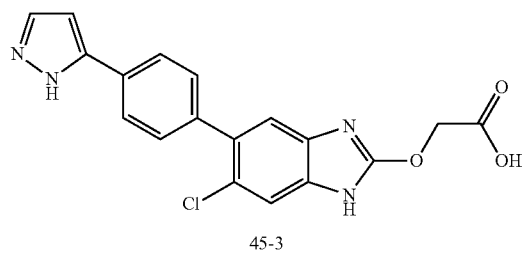
45-3

Step A. 6-Chloro-2-methanesulfonyl-5-[4-(2H-pyrazol-3-yl)-phenyl]-1-(2-trimethylsilanyl-ethoxymethyl)-1H-benzoimidazole (45-1)

A 5 mL Biotage™ microwave vial was charged with 6-chloro-5-iodo-2-methanesulfonyl-1-(2-trimethylsilanyl-ethoxymethyl)-1H-benzoimidazole (Intermediate 5, 73.2 mg, 0.150 mmol), 4-(2H-pyrazol-3-yl)-phenylboronic acid (33.9 mg, 0.180 mmol) and Pd(PPh$_3$)$_4$ (8.7 mg, 5 mol %) followed by dioxane (1.5 mL) and 1M aqueous K$_2$CO$_3$ (180 uL). The resulting suspension was heated in a microwave synthesizer (Biotage Initiator™) at 130° C. for 10 min. The suspension was then diluted with EtOAc (5 mL) and washed with 1M aqueous K$_2$CO$_3$ (twice, 1 mL) and water (twice, 1 mL). The organic layer was evaporated to dryness in vacuo to give yellow oil. The oil was dissolved in ACN and passed through a Thiol StratoSphere™ SPE cartridge (Polymer Labs). The solvent was evaporated to dryness in vacuo to give the crude product as pale yellow solid. LR-MS (API-ES): calculated for C$_{23}$H$_{27}$ClN$_4$O$_3$SSi 502.1, observed m/e 503.0 (M+H)$^+$ (R$_t$ 3.30 min).

Step B. [5-[4-(2H-Pyrazol-3-yl)-phenyl]-1-(2-trimethylsilanyl-ethoxymethyl)-1H-benzoimidazol-2-yloxy]-acetic acid (45-2)

A 20 mL scintillation vial equipped with a septum cap and a magnetic stirring bar was charged under N$_2$ with NaH (18.0 mg, 60% suspension in mineral oil, 0.45 mmol). A solution of hydroxyacetic acid methyl ester (81.0 mg, 0.90 mmol) in THF (1.5 mL) was added dropwise to the vial. Immediately after the addition was complete, a solution of 6-chloro-2-methanesulfonyl-5-[4-(2H-pyrazol-3-yl)-phenyl]-1-(2-trimethylsilanyl-ethoxymethyl)-1H-benzoimidazole (compound 45-1, 75.0 mg, 0.150 mmol) in THF (1 mL) was added. The resulting suspension was stirred at rt for 5 min, then diluted with ACN (2 mL) and quenched by slow addition of water (2 mL). The resulting solution was stirred at rt for 5 min, and then additional 15 min at 65° C. The solution was acidified with 5% aqueous HCl and extracted with EtOAc (three times, 3 mL). The organic layers were combined and washed with 5% aqueous HCl and water and evaporated to dryness in vacuo to give the title compound as yellowish oil. LR-MS (API-ES): mixture of two N-SEM isomers, calculated for C$_{24}$H$_{27}$ClN$_4$O$_4$Si 498.2, observed m/e 499.0 (M+H)$^+$ (R$_t$ 3.01, 3.15 min). The compound was used in the next step without further purification.

Step C. {6-Chloro-5-[4-(2H-pyrazol-3-yl)-phenyl]-1H-benzoimidazol-2-yloxy}-acetic acid (45-3)

In a 4 mL vial, [5-[4-(2H-pyrazol-3-yl)-phenyl]-1-(2-trimethylsilanyl-ethoxymethyl)-1H-benzoimidazol-2-yloxy]-acetic acid (compound 45-2, 74.8 mg, 0.15 mmol) was dissolved in 9:1 TFA/water (1 mL). The solution was agitated at 65° C. for 15 min and evaporated to dryness in vacuo to give yellowish oil. The oil was dissolved in DMSO (1 mL), filtered and purified by reverse-phase HPLC to give the title compound as white solid. LR-MS (API-ES): calculated for C$_{18}$H$_{13}$ClN$_4$O$_3$ 368.1, observed m/e 369.0 (M+H)$^+$ (R$_t$ 2.31 min).

Example 46

[(5-biphenyl-4-yl-6-chloro-1H-benzimidazol-2-yl)oxy]ylacetic acid

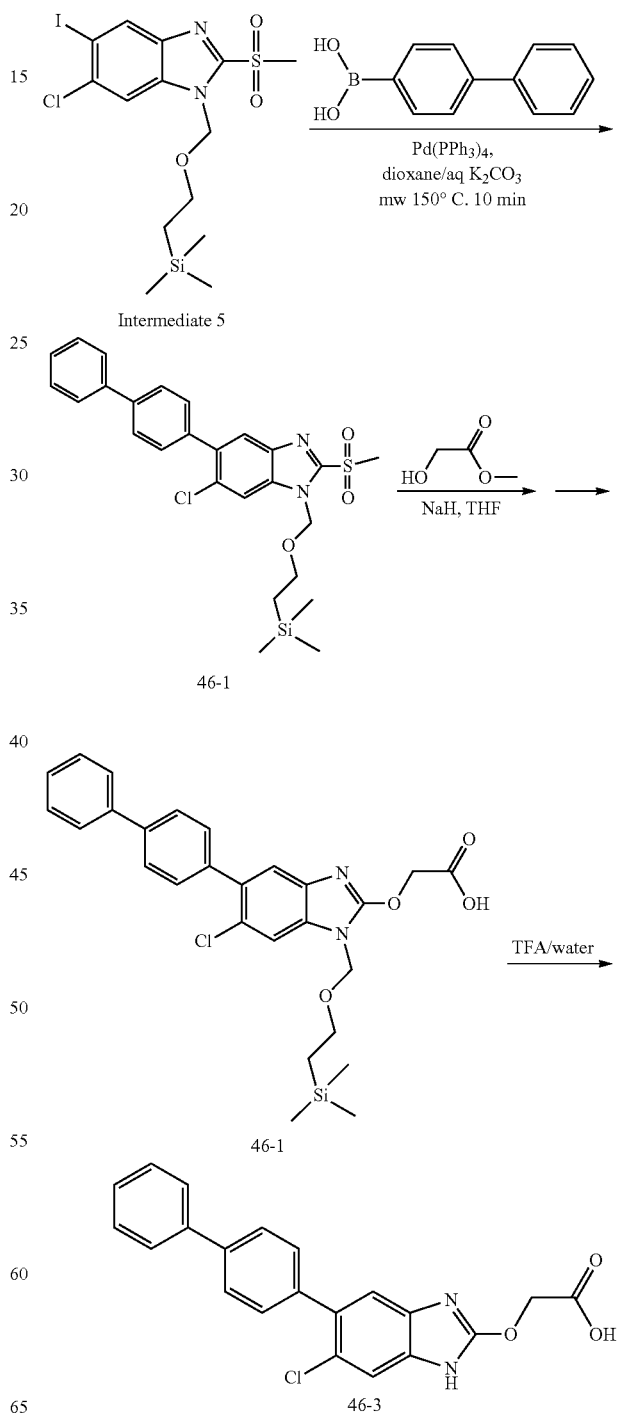

Step A. 5-Biphenyl-4-yl-2-methanesulfonyl-1-(2-trimethylsilanyl-ethoxymethyl)-1H-benzoimidazole (46-1)

A 2 mL Biotage™ microwave vial was charged with 6-chloro-5-iodo-2-methanesulfonyl-1-(2-trimethylsilanyl-ethoxymethyl)-1H-benzoimidazole (Intermediate 5, 49.0 mg, 0.100 mmol), biphenyl-4-boronic acid (24.0 mg, 0.120 mmol) and Pd(PPh$_3$)$_4$ (5.8 mg, 5 mol %) following by dioxane (1.0 mL) and 1M aqueous K$_2$CO$_3$ (120 uL). The resulting suspension was heated in a microwave synthesizer (Biotage Initiator™) at 150° C. for 10 min. The microwave procedure was repeated two more times, before each irradiation additional Pd(PPh$_3$)$_4$ (2.9 mg, 2.5 mol %) was added. The reaction mixture was then diluted with EtOAc (5 mL), filtered and the resulting solution was evaporated to dryness in vacuo to give brown oil. The oil was dissolved in ACN and passed through a Thiol StratoSphere™ SPE cartridge (Polymer Labs). The solvent was evaporated to dryness in vacuo to give crude product as colorless oil which was used in the next step without further purification. LR-MS (API-ES): calculated C$_{26}$H$_{29}$ClN$_2$O$_3$SSi 512.1, observed m/e 513.0 (M+H)$^+$, 485.0, 455.0 (R$_t$ 3.91 min).

Step B. [5-Biphenyl-4-yl-1-(2-trimethylsilanyl-ethoxymethyl)-1H-benzoimidazol-2-yloxy]-acetic acid (46-2)

A 20 mL scintillation vial equipped with a septum cap and a magnetic stirring bar was charged under N$_2$ with NaH (6.0 mg, 60% suspension in mineral oil, 0.15 mmol). A solution of hydroxyacetic acid methyl ester (18.0 mg, 0.200 mmol) in THF (2.0 mL) was added dropwise to the vial and the resulting mixture was stirred at rt for 10 min. Then, a solution of 5-biphenyl-4-yl-2-methanesulfonyl-1-(2-trimethylsilanyl-ethoxymethyl)-1H-benzoimidazole (compound 46-1, 51.3 mg, 0.100 mmol) in THF (1 mL) was added. The resulting mixture was stirred at rt for 10 mM, then diluted by dropwise addition of 1:1 ACN/water (2 mL) and left to stir at rt for 30 min. The reaction mixture was then diluted with water (5 mL), acidified with 5% aqueous HCl and extracted with EtOAc (three times, 3 mL). The organic layers were combined and washed with 5% aqueous HCl and water, and evaporated to dryness in vacuo to give the title compound as pale yellow solid. LR-MS (API-ES): mixture of two N-SEM isomers, calculated for C$_{27}$H$_{29}$ClN$_2$O$_4$Si 508.2, observed m/e 509.0 [(M+H)$^+$, 100%], 465 (R$_t$ 3.74 min). The compound was used in the next step without further purification.

Step C. [(5-biphenyl-4-yl-6-chloro-1H-benzimidazol-2-yl)oxy]acetic acid (46-3)

In a 4 mL vial, [5-biphenyl-4-yl-1-(2-trimethylsilanyl-ethoxymethyl)-1H-benzoimidazol-2-yloxy]-acetic acid methyl ester (compound 46-2, 52.3 mg, 0.100 mmol) was dissolved in 9:1 TFA/water (3 mL). The solution was stirred at 65° C. for 10 min, then evaporated to dryness in vacuo to give pale yellow solid. The solid was dissolved in DMSO (1 mL), filtered and purified by reverse-phase HPLC to give the title compound as yellowish solid. LR-MS (API-ES): calculated for C$_{21}$H$_{15}$ClN$_2$O$_3$ 378.1, observed m/e 379.1 (M+H)$^+$ (R$_t$ 1.36 min).

Example 47

[5-(4-Hydroxymethyl-phenylethynyl)-1H-benzoimidazol-2-yloxy]-acetic acid

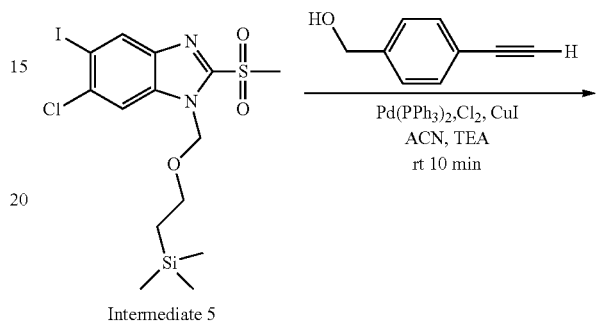

Intermediate 5

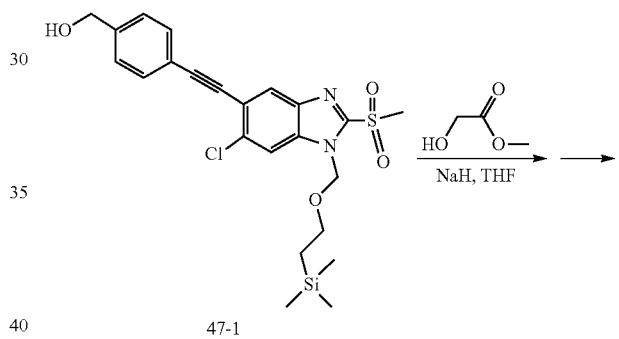

47-1

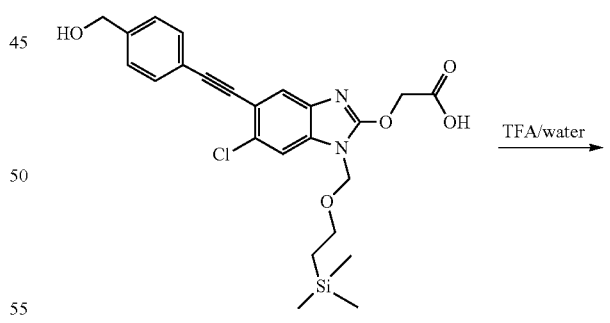

47-2

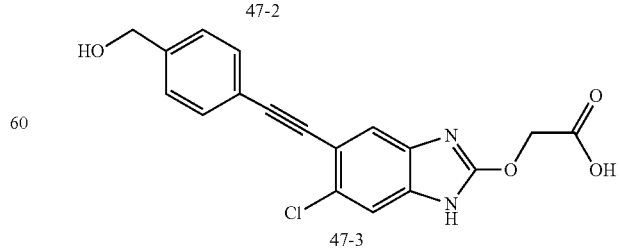

47-3

Step A. {4-[2-Methanesulfonyl-1-(2-trimethylsilanyl-ethoxymethyl)-1H-benzoimidazol-5-ylethynyl]-phenyl}-methanol (47-1)

A 4 mL vial equipped with a stirring bar was charged with copper iodide (1.0 mg, 5 mol %) and Pd(PPh$_3$)$_2$Cl$_2$ (2.0 mg, 2.5 mol %). A solution of 6-chloro-5-iodo-2-methanesulfonyl-1-(2-trimethylsilanyl-ethoxymethyl)-1H-benzoimidazole (Intermediate 5, 49.0 mg, 0.100 mmol) in ACN (1 mL) was added to the vial, followed by a solution of (4-ethynyl-phenyl)-methanol (26.0 mg, 0.200 mmol) in ACN (0.5 mL) and TEA (98 uL, 0.70 mmol). The resulting suspension was stirred at it for 10 min, during which time it gradually turned dark brown. The reaction mixture was than passed through a Thiol StratoSphere™ SPE cartridge (Polymer Labs). The resulting solution was evaporated to dryness in vacuo to give yellow oil. The oil was re-dissolved in ACN and passed through a short pad of silica. Evaporation of solvent provided the crude product as yellow oily solid which was used in the next step without further purification. LR-MS (API-ES): mixture of two N-SEM isomers, calculated C$_{23}$H$_{27}$ClN$_2$O$_4$SSi 490.1, observed m/e 491.0 (M+H)$^+$, 463.0, 433 (R$_t$ 3.25, 3.40 min).

Step B. [5-(4-Hydroxymethyl-phenylethynyl)-1-(2-trimethylsilanyl-ethoxymethyl)-1H-benzoimidazol-2-yloxy]-acetic acid (47-2)

A 20 mL scintillation vial equipped with a septum cap and a magnetic stirring bar was charged under N$_2$ with NaH (12.0 mg, 60% suspension in mineral oil, 0.30 mmol). A solution of hydroxyacetic acid methyl ester (54.0 mg, 0.60 mmol) in THF (1.0 mL) was added dropwise to the vial. Immediately after the addition was complete, a solution of {4-[2-methanesulfonyl-1-(2-trimethylsilanyl-ethoxymethyl)-1H-benzoimidazol-5-ylethynyl]-phenyl}-methanol (compound 47-1, 49.1 mg, 0.100 mmol) in THF (1 mL) was added. The resulting yellowish suspension was stirred at it for 5 min, then diluted with ACN (2 mL) and quenched by addition of water (2 mL). The resulting solution was stirred at it for 5 min, then an additional 15 min at 65° C. The solution was acidified with 5% aqueous HCl and extracted with EtOAc (three times, 3 mL). The organic layers were combined and washed with 5% aqueous HCl and water and evaporated to dryness in vacuo to give the crude product as yellowish solid. LR-MS (APT-ES): mixture of two N-SEM isomers, calculated for C$_{24}$H$_{27}$ClN$_2$O$_5$Si 486.2, observed m/e 487.0 (M+H)$^+$ (R$_t$ 3.09, 3.20 min). The crude product was used in the next step without further purification.

Step C. [5-(4-Hydroxymethyl-phenylethynyl)-1H-benzoimidazol-2-yloxy]-acetic acid (47-3)

In a 4 mL vial, [5-(4-hydroxymethyl-phenylethynyl)-1-(2-trimethylsilanyl-ethoxymethyl)-1H-benzoimidazol-2-yloxy]-acetic acid (compound 47-2, 48.7 mg, 0.100 mmol) was dissolved in 9:1 TFA/water (1 mL). The solution was stirred at rt for 45 min, then evaporated to dryness in vacuo to give brownish oil. The oil was dissolved in DMSO (1 mL), filtered and purified by reverse-phase HPLC to give the formate salt of the title compound as a yellowish solid. LR-MS (API-ES): calculated for C$_{18}$H$_{13}$ClN$_2$O$_4$ 356.1, observed m/e 357.0 (M+H)$^+$ (R$_t$ 1.84 min).

Example 48

(6-Chloro-5-phenylethynyl-1H-benzoimidazol-2-yloxy)-acetic acid

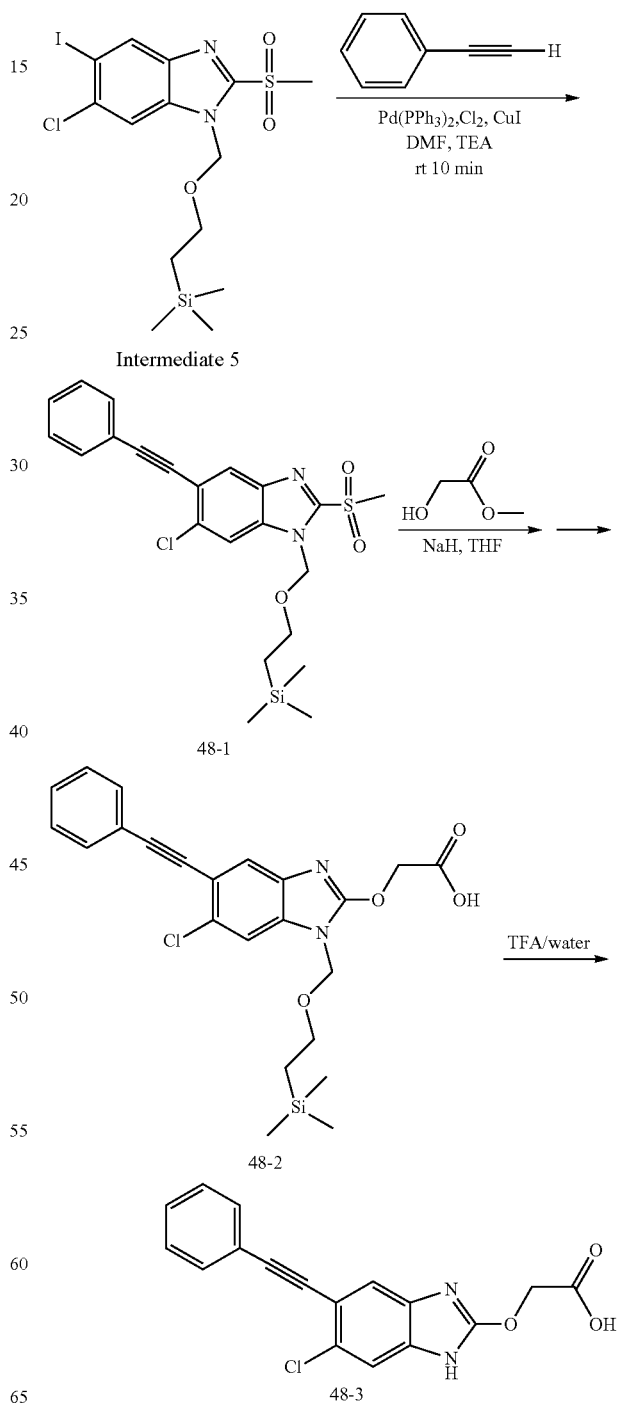

Step A. 6-Chloro-2-methanesulfonyl-5-phenylethynyl-1-(2-trimethylsilanyl-ethoxymethyl)-1H-benzoimidazole (48-1)

A 4 mL vial equipped with a stirring bar was charged with copper iodide (2.0 mg, 10 mol %), and Pd(PPh₃)₂Cl₂ (3.5 mg, 5 mol %). A solution of 6-chloro-5-iodo-2-methanesulfonyl-1-(2-trimethylsilanyl-ethoxymethyl)-1H-benzoimidazole (Intermediate 5, 49.0 mg, 0.100 mmol) in DMF (0.5 mL) was added to the vial, followed by a solution of ethynyl-benzene (20.0 mg, 0.200 mmol) in DMF (0.5 mL) and TEA (98 uL, 0.70 mmol). The resulting suspension was stirred at rt for 10 min, during which time it gradually turned brown. The solvent was then removed in vacuo to give brown oily solid, which was suspended in 1:1 EtOAc/MeOH (3 mL) and passed through a Thiol StratoSphere™ SPE cartridge (Polymer Labs). The resulting solution was evaporated to dryness in vacuo to give light yellow oil. LR-MS (API-ES): calculated $C_{22}H_{25}ClN_2O_3SSi$ 460.1, m/e (M+H)⁺ not observed, 433.0, 403 ($R_t$ 3.83 min).

Step B. [6-Chloro-5-phenylethynyl-1-(2-trimethylsilanyl-ethoxymethyl)-1H-benzoimidazol-2-yloxy]-acetic acid (48-2)

A 20 mL scintillation vial equipped with a septum cap and a magnetic stirring bar was charged under $N_2$ with NaH (10.5 mg, 60% suspension in mineral oil, 0.26 mmol). A solution of hydroxyacetic acid methyl ester (54.0 mg, 0.35 mmol) in THF (2.0 mL) was added dropwise to the vial. Immediately after the addition was complete, a solution of [6-chloro-5-phenylethynyl-1-(2-trimethylsilanyl-ethoxymethyl)-1H-benzoimidazol-2-yloxy]-acetic acid (compound 48-1, 80.0 mg, 0.173 mmol) in THF (1 mL) was added. The resulting yellowish suspension was stirred at rt for 10 min, then diluted by a dropwise addition of 1:1 ACN/water (2 mL). The resulting solution was stirred at rt for 1 h, and then evaporated to dryness in vacuo to give the crude product as brown oil. LR-MS (API-ES): mixture of two N-SEM isomers, calculated for $C_{23}H_{25}ClN_2O_4Si$ 456.1, observed m/e 457.0 (M+H)⁺ ($R_t$ 3.09, 3.20 min). The crude product was used in the next step without further purification.

Step C. (6-Chloro-5-phenylethynyl-1H-benzoimidazol-2-yloxy)-acetic acid (48-3)

In a 4 mL vial, [6-chloro-5-phenylethynyl-1-(2-trimethylsilanyl-ethoxymethyl)-1H-benzoimidazol-2-yloxy]-acetic acid (compound 48-2, 79.0 mg, 0.173 mmol) was dissolved in 9:1 TFA/water (3 mL) and stirred at 65° C. for 10 min. The solution was then evaporated to dryness in vacuo to give brownish oil, which was dissolved in DMSO (1 mL), filtered and purified by reverse-phase HPLC to give the title compound as a yellowish solid. LR-MS (API-ES): calculated for $C_{17}H_{11}ClN_2O_3$ 326.1, observed m/e 327.1 (M+H)⁺ ($R_t$ 1.25 min).

General Scheme 4

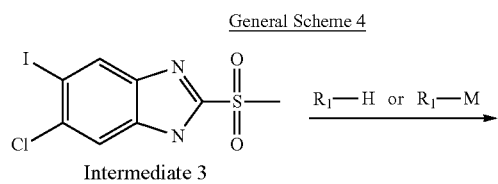

Intermediate 3

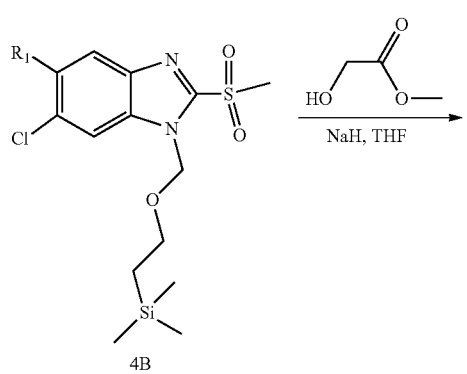

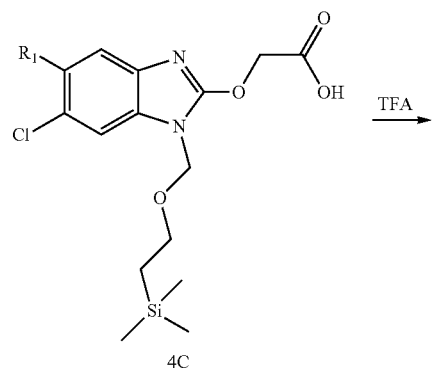

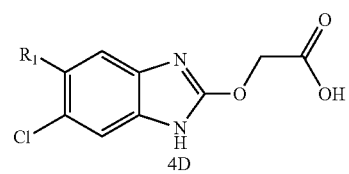

In General Scheme 4, Intermediate 3 is reacted with a boronic acid, boronate ester or stannane ($R^1$-M) in the presence of palladium tetrakistriphenylphosphine to afford compound 4A. Alternatively, Intermediate 3 is reacted with an acetylene ($R^1$—H) in the presence of copper (I) iodide and bis(triphenylphosphine)palladium (II) chloride to afford compound 4A. Subsequent protection with SEM-Cl followed by reaction of SEM protected reaction intermediate 4B with an alcohol, then hydrolysis of the product 4C affords the 2-substituted benzimidazole 4D.

Example 49

3-(6-Chloro-5-phenylethynyl-1H-benzoimidazol-2-yloxy)-2,2-dimethyl-propionic acid

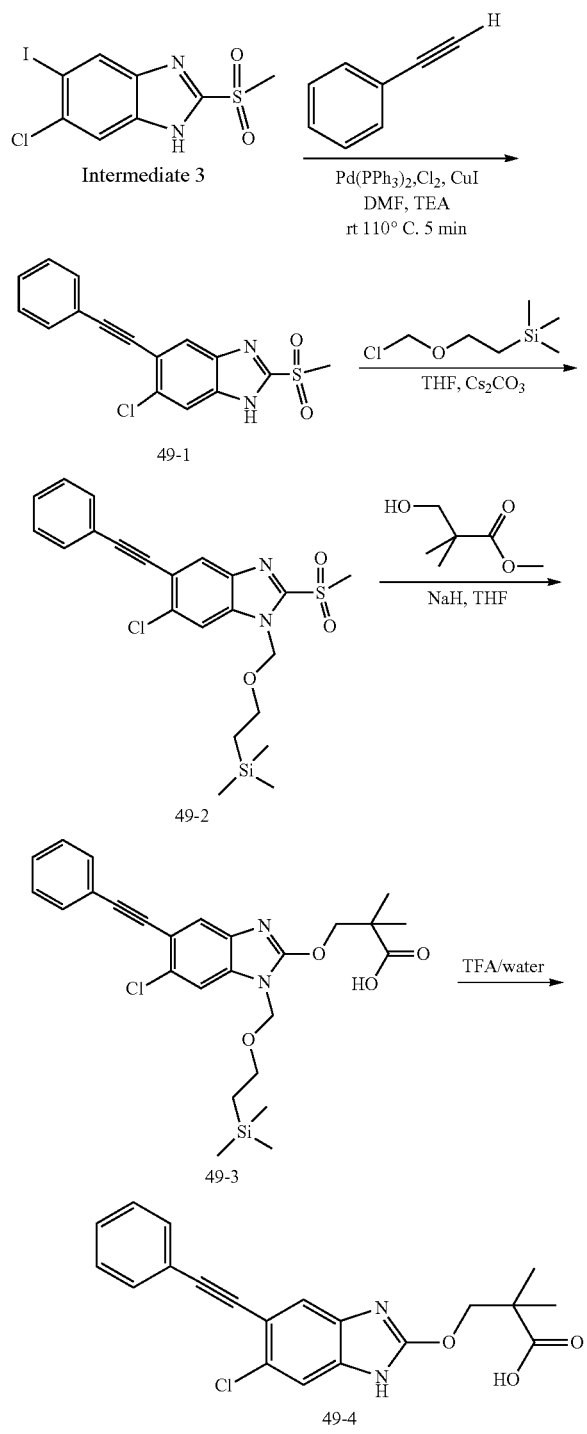

Step A. 6-Chloro-2-methanesulfonyl-5-phenylethynyl-1-(2-trimethylsilanyl-ethoxymethyl)-1H-benzoimidazole (49-1)

A 2 mL Biotage™ microwave vial was charged with copper iodide (5.7 mg, 10 mol %), and Pd(PPh$_3$)$_2$Cl$_2$ (10.5 mg, 5 mol %). A solution of 6-chloro-5-iodo-2-methanesulfonyl-1H-benzoimidazole (Intermediate 3, 107.0 mg, 0.300 mmol) in DMF (0.75 mL) was added to the vial, followed by a solution of ethynyl-benzene (61.0 mg, 0.600 mmol) in DMF (0.5 mL) and TEA (293 uL, 2.10 mmol). The resulting suspension was heated in a microwave synthesizer (Biotage Initiator™) at 110° C. for 5 min. The solvent was then removed in vacuo to give dark brown oil, which was suspended in 1:1 EtOAc/MeOH (3 mL), passed through a Thiol Strato-Sphere™ SPE cartridge (Polymer Labs). The resulting solution was evaporated to dryness in vacuo to give the crude product as a brown solid. LR-MS (API-ES): calculated for $C_{16}H_{11}ClN_2O_2S$ 330.0, observed m/e 331.0 (M+H)$^+$ ($R_t$ 3.10 min). The crude product was used in the next step without further purification.

Step B. 6-Chloro-2-methanesulfonyl-5-phenylethynyl-1-(2-trimethylsilanyl-ethoxymethyl)-1H-benzoimidazole (49-2)

A solution of SEM-Cl (75.0 mg, 0.45 mmol) in THF (2 mL) was added dropwise with stirring to an ice-bath (0° C.) cooled suspension of Cs$_2$CO$_3$ (195 mg, 0.600 mmol) in THF (3 mL) containing compound 49-1 (99.0 mg, 0.300 mmol). The resulting suspension was stirred at 0° C. for 30 min then allowed to warm up to rt, and stirred at rt for additional 30 min. The suspension was than diluted with water (8 mL) and extracted with EtOAc (5 mL, then 2 mL, twice). The organic layers were combined and evaporated to dryness in vacuo to give the crude product as yellowish oil. LR-MS (API-ES): mixture of two N-SEM isomers, calculated for $C_{22}H_{25}ClN_2O_3SSi$ 460.1, m/e (M+H)$^+$ not observed, 433, 403 (100%) ($R_t$ 3.83 min). The crude product was used in the next step without further purification.

Step C. 3-[6-Chloro-5-phenylethynyl-1-(2-trimethylsilanyl-ethoxymethyl)-1H-benzoimidazol-2-yloxy]-2,2-dimethyl-propionic acid (49-3)

A 20 mL scintillation vial equipped with a septum cap and a magnetic stirring bar was charged under N$_2$ with NaH (18.0 mg, 60% suspension in mineral oil, 0.45 mmol). In a separate vial, a solution of 3-hydroxy-2,2-dimethyl-propionic acid methyl ester (79.0 mg, 0.600 mmol) in THF (2.0 mL) was combined with a solution of compound 49-2 (138.0 mg, 0.300 mmol), and added dropwise to the 20 mL scintillation vial containing NaH. The resulting mixture was stirred at rt for 5 min, then cooled in a ice bath (0° C.) and quenched by a dropwise addition of water (6 mL). The mixture was allowed to warm up to rt and stirring was maintained for 5 min. The mixture was acidified with 5% aqueous HCl and extracted with EtOAc (three times, 3 mL). The organic layers were combined and evaporated to dryness in vacuo. The residue was dissolved in ACN (4 mL) and added to a vial containing 5% aqueous LiOH (1 mL). The resulting mixture was stirred at 65° C. for 1 h, then acidified with 5% aqueous HCl and extracted with EtOAc (three times, 3 mL). The organic layers were combined and evaporated to dryness in vacuo. The crude product was used in the next step without further purification.

LR-MS (API-ES): mixture of two N-SEM isomers, calculated for $C_{26}H_{31}ClN_2O_4Si$ 498.2, observed m/e 499.0 $(M+H)^+$ ($R_t$ 3.78. 3.87 min).

Step D. 3-(6-Chloro-5-phenylethynyl-1H-benzoimidazol-2-yloxy)-2,2-dimethyl-propionic acid (49-4)

In a 4 mL vial, compound 49-3 (86.0 mg, 0.173 mmol) was dissolved in 9:1 TFA/water (3 mL) and stirred at 65° C. for 10 min. The solution was then evaporated to dryness in vacuo to give oily residue, which was dissolved in DMSO (1 mL), filtered and purified by reverse-phase HPLC to give the formate salt of the title compound. LR-MS (API-ES): calculated for $C_{20}H_{17}ClN_2O_3$ 368.1, observed m/e 369.2 $(M+H)^+$ ($R_t$ 1.26 min).

Example 50

3-(6-Chloro-5-phenyl-1H-benzimidazol-2-yl)-propionic acid

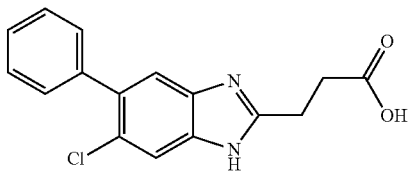 [SMILES: O=C(O)CCc1nc2cc(-c3ccccc3)c(Cl)cc2[nH]1]

3-(6-Chloro-5-phenyl-1H-benzimidazol-2-yl)-propionic acid

A 4 mL vial with a septum cap and a stirring bar was charged with phenylboronic acid (4.5 mg, 0.037 mmol) and Pd(PPh$_3$)$_4$ (2.0 mg, 5 mol %) and was purged briefly with N$_2$. A solution of 3-(5-bromo-6-chloro-1H-benzimidazol-2-yl)-propionic acid methyl ester (Intermediate 9, 10.0 mg, 0.032 mmol) in DME (200 uL) was added to the vial, followed 1M aqueous K$_2$CO$_3$ (100 uL). The resulting mixture was stirred at 85° C. for 10 h. The mixture was allowed to cool down to rt, and was partitioned with EtOAc (1 mL) and 10% aqueous AcOH (1 mL). The organic layer was separated and evaporated to dryness in vacuo. The resulting oily residue was dissolved in DMSO (1.0 mL), filtered and purified by reverse-phase HPLC to give the title compound. LR-MS (API-ES): calculated for $C_{16}H_{13}ClN_2O_2$ 300.0, observed m/e 301.0 $(M+H)^+$ ($R_t$ 2.42 min).

Example 51

3-(5-Biphenyl-4-yl-6-chloro-1H-benzimidazol-2-yl)-propionic acid

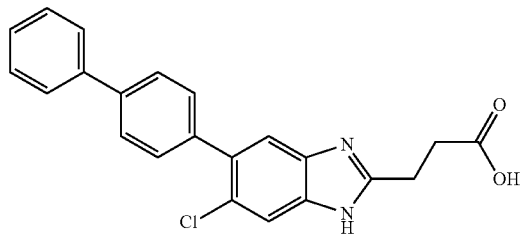 [SMILES: O=C(O)CCc1nc2cc(-c3ccc(-c4ccccc4)cc3)c(Cl)cc2[nH]1]

3-(5-Biphenyl-4-yl-6-chloro-1H-benzimidazol-2-yl)-propionic acid

The title compound was prepared by procedure described in Example 50 by substituting phenylboronic acid with biphenyl-4-boronic acid. LR-MS (APT-ES): calculated for $C_{22}H_{17}ClN_2O_2$ 376.1, observed m/e 377.0 $(M+H)^+$ ($R_t$ 3.02 min).

Example 52

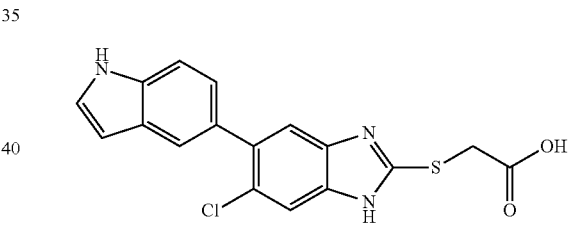

[6-Chloro-5-(1H-indol-5-yl)-1H-benzoimidazol-2-ylsulfanyl]acetic acid

A mixture of ethyl 2-(6-chloro-5-iodo-1H-benzo[d]imidazol-2-ylthio) acetate (Intermediate 8; 0.15 g, 0.38 mmol), 5-indoylboronic acid (0.091 g, 0.57 mmol), PdCl(dppf) (0.013 g, 0.019 mmol), K$_2$CO$_3$ (0.163 g, 1.2 mmol), 3 mL of toluene and 1 mL of H$_2$O was heated to 130° C. for 10 minutes using a microwave reactor. LCMS indicated incomplete reaction; therefore, the mixture was heated to 140° C. for 15 min using a microwave reactor. The crude mixture was diluted with 20 mL of 1:1 EtOAc:H$_2$O. The aqueous layer was collected and acidified to ~pH=1 with 1M HCl. Then the title compound was extracted using EtOAc. The organic fractions were combined, dried over MgSO$_4$ and concentrated in vacuo. This crude material was purified by HPLC using 30-80% acetonitrile-H$_2$O with 0.05% TFA and lyophilized to afford the title compound as white solid. $^1$H NMR (DMSO-d6) δ 11.17 (1H, s), 7.61 (1H, s), 7.55 (1H, s), 7.44 (1H, d, J=8.5 Hz), 7.399-7.39 (2H, m), 7.13 (1H, d, J=8.5), 6.47 (1H, s), 4.17 (2H, s); LRMS (API-ES) m/e for $C_{17}H_{12}ClN_3O_2S$ $(M+H)^+$, calcd 357.82, found 358.4. Anal. Calcd for $C_{17}H_{12}ClN_3O_2S+2.2H_2O+0.3$ TFA: C, 48.97; H, 3.90; N, 9.73. Found: C, 48.59; H, 3.54; N, 9.38.

Example 53

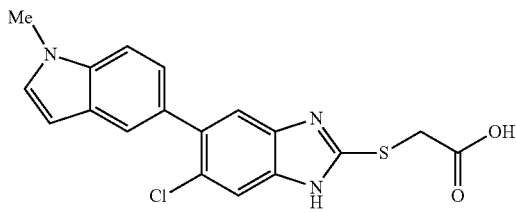 [SMILES: Cn1ccc2cc(-c3cc4nc(SCC(=O)O)[nH]c4cc3Cl)ccc21]

[6-Chloro-5-(1-methyl-indol-5-yl)-1H-benzoimidazol-2-ylsulfanyl]acetic acid

A mixture of ethyl 2-(6-chloro-5-iodo-1H-benzo[d]imidazol-2-ylthio)acetate (Intermediate 8; 0.15 g, 0.38 mmol), 1-methyl-5-indoylboronic acid (0.099 g, 0.57 mmol), PdCl(dppf) (0.013 g, 0.019 mmol), $K_2CO_3$ (0.163 g, 1.2 mmol), 3 mL of toluene and 1 mL of $H_2O$ was heated to 130° C. for 10 minutes using a microwave reactor. LCMS indicated complete reaction. The crude mixture was diluted with 20 mL of 1:1 EtOAc:$H_2O$. The aqueous layer was collected and acidified to ~pH=1 with 1M HCl. Then the title compound was extracted using EtOAc. The organic fractions were combined, dried over $MgSO_4$ and concentrated in vacuo. This crude material was purified by HPLC using 30-80% acetonitrile-$H_2O$ with 0.05% TFA and lyophilized to afford the title compound as an off-white solid. $^1$H NMR (DMSO-d6) δ 7.61 (1H, s), 7.56 (1H, s), 7.48 (1H, d, J=8.5 Hz), 7.39 (1H, s), 7.37 (1H, d, J=3 Hz), 7.20 (dd, J=8.5, 3.0 Hz), 6.46 (1H, s), 4.17 (2H, s), 3.52 (3H, s); LRMS (API-ES) m/e for $C_{18}H_{14}ClN_3O_2S$ (M+H)$^+$, calcd 371.85, found 372.1. Anal. Calcd for $C_{18}H_{14}ClN_3O_2S+2H_2O+0.5$ TFA: C, 49.09; H, 4.01; N, 9.04. Found: C, 49.33; H, 3.72; N, 8.76.

TABLE 6

Examples 54-86 in Table 6 were prepared following the procedures described in Examples 52 and 53 and using the appropriate starting materials.

| Example No. | Structure | LCMS (M + H)+ |
|---|---|---|
| 54 | 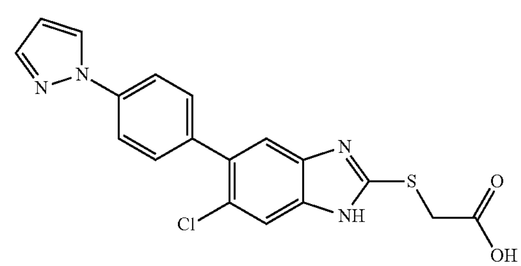 [SMILES: O=C(O)CSc1nc2cc(-c3ccc(-n4cccn4)cc3)c(Cl)cc2[nH]1] | 385.4 |
| 55 | 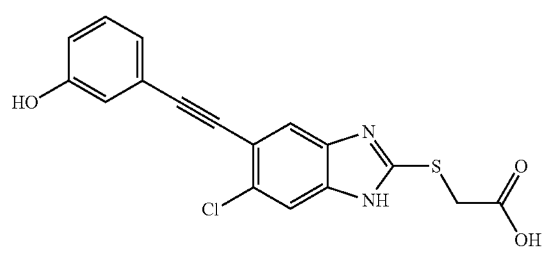 [SMILES: O=C(O)CSc1nc2cc(C#Cc3cccc(O)c3)c(Cl)cc2[nH]1] | 359.1 |
| 56 | 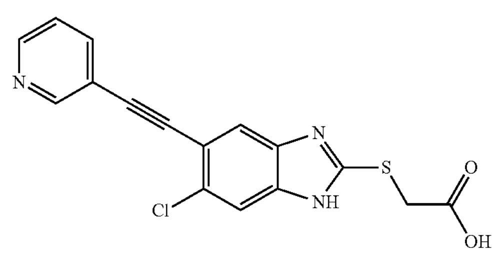 [SMILES: O=C(O)CSc1nc2cc(C#Cc3cccnc3)c(Cl)cc2[nH]1] | 344.1 |

TABLE 6-continued

Examples 54-86 in Table 6 were prepared following the procedures described in Examples 52 and 53 and using the appropriate starting materials.

| Example No. | Structure | LCMS (M + H)+ |
|---|---|---|
| 57 | 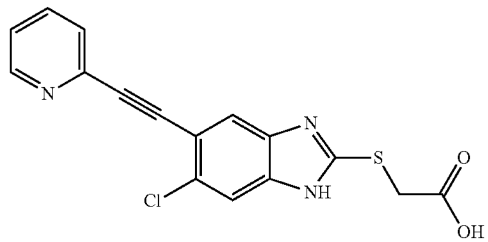 [SMILES: O=C(O)CSc1nc2cc(C#Cc3ccccn3)c(Cl)cc2[nH]1] | 344.1 |
| 58 | 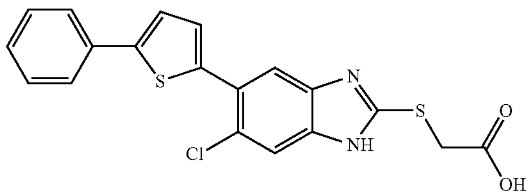 [SMILES: O=C(O)CSc1nc2cc(-c3ccc(-c4ccccc4)s3)c(Cl)cc2[nH]1] | 401.1 |
| 59 | 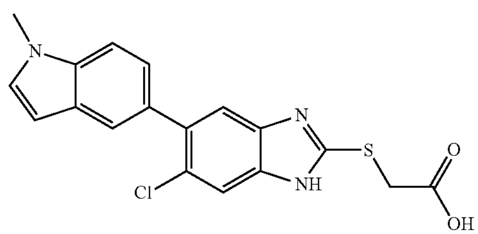 [SMILES: Cn1ccc2cc(-c3cc4nc(SCC(=O)O)[nH]c4cc3Cl)ccc21] | 372.1 |
| 60 | 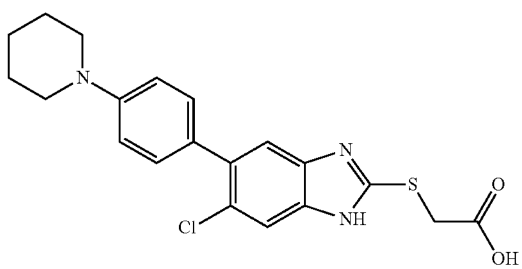 [SMILES: O=C(O)CSc1nc2cc(-c3ccc(N4CCCCC4)cc3)c(Cl)cc2[nH]1] | 402.1 |
| 61 | 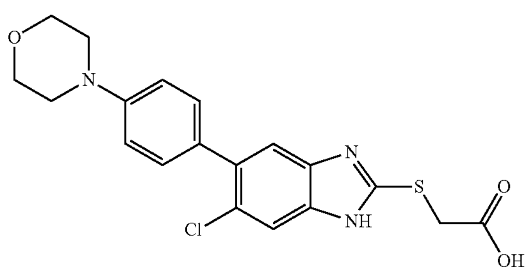 [SMILES: O=C(O)CSc1nc2cc(-c3ccc(N4CCOCC4)cc3)c(Cl)cc2[nH]1] | 404.4 |
| 62 | 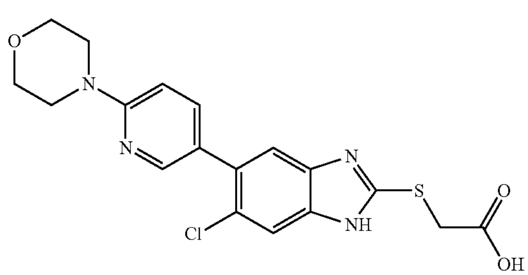 [SMILES: O=C(O)CSc1nc2cc(-c3ccc(N4CCOCC4)nc3)c(Cl)cc2[nH]1] | 405.4 |

TABLE 6-continued

Examples 54-86 in Table 6 were prepared following the procedures described in
Examples 52 and 53 and using the appropriate starting materials.

| Example No. | Structure | LCMS (M + H)+ |
|---|---|---|
| 63 | 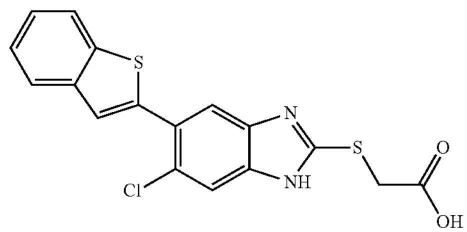 [SMILES: O=C(O)CSc1nc2cc(-c3cc4ccccc4s3)c(Cl)cc2[nH]1] | 375.1 |
| 64 | 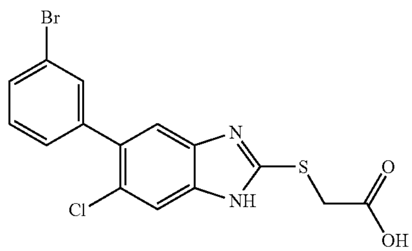 [SMILES: O=C(O)CSc1nc2cc(-c3cccc(Br)c3)c(Cl)cc2[nH]1] | 423.1 |
| 65 | 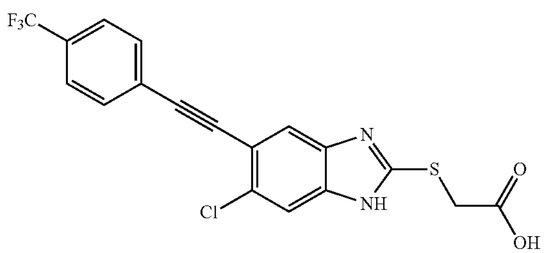 [SMILES: O=C(O)CSc1nc2cc(C#Cc3ccc(C(F)(F)F)cc3)c(Cl)cc2[nH]1] | 409.4 |
| 66 | 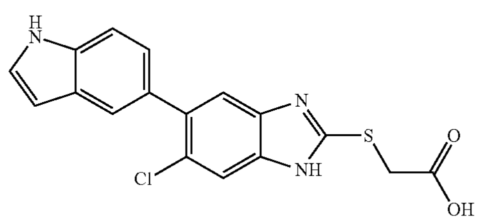 [SMILES: O=C(O)CSc1nc2cc(-c3ccc4[nH]ccc4c3)c(Cl)cc2[nH]1] | 358.4 |
| 67 | 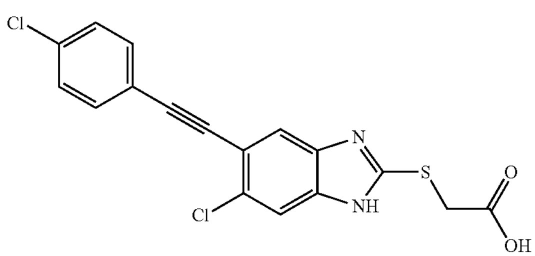 | 377.1 |
| 68 | 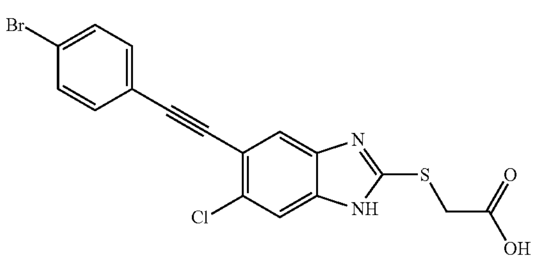 [SMILES: O=C(O)CSc1nc2cc(C#Cc3ccc(Cl)cc3)c(Cl)cc2[nH]1] | 423.1 |

TABLE 6-continued
Examples 54-86 in Table 6 were prepared following the procedures described in Examples 52 and 53 and using the appropriate starting materials.
| Example No. | Structure | LCMS (M + H)+ |
|---|---|---|
| 69 | 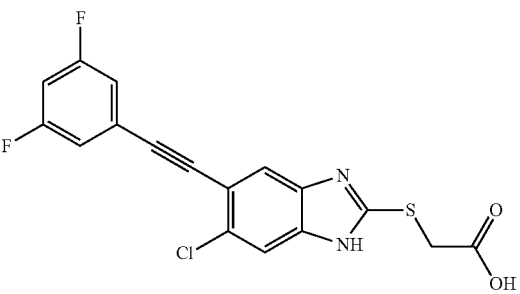 [SMILES: O=C(O)CSc1nc2cc(C#Cc3cc(F)cc(F)c3)c(Cl)cc2[nH]1] | 379.4 |
| 70 | 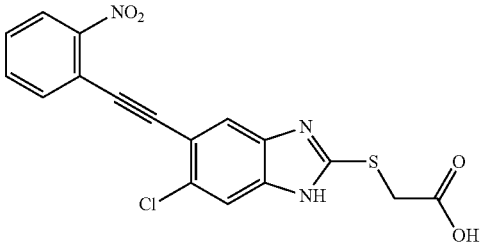 [SMILES: O=C(O)CSc1nc2cc(C#Cc3ccccc3[N+](=O)[O-])c(Cl)cc2[nH]1] | 388.1 |
| 71 | 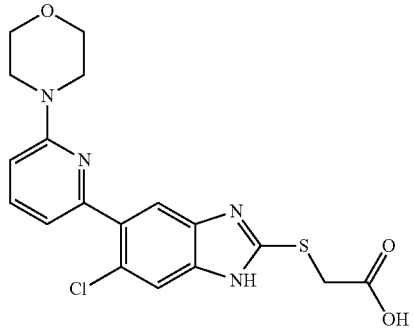 [SMILES: O=C(O)CSc1nc2cc(-c3cccc(N4CCOCC4)n3)c(Cl)cc2[nH]1] | 405.4 |
| 72 | 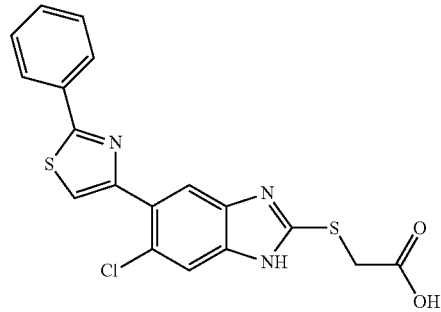 [SMILES: O=C(O)CSc1nc2cc(-c3csc(-c4ccccc4)n3)c(Cl)cc2[nH]1] | 402.1 |
| 73 | 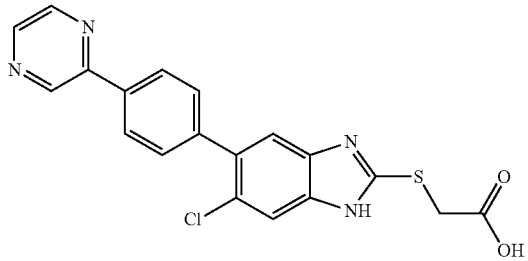 [SMILES: O=C(O)CSc1nc2cc(-c3ccc(-c4cnccn4)cc3)c(Cl)cc2[nH]1] | 397.1 |

TABLE 6-continued

Examples 54-86 in Table 6 were prepared following the procedures described in Examples 52 and 53 and using the appropriate starting materials.

| Example No. | Structure | LCMS (M + H)+ |
|---|---|---|
| 74 | 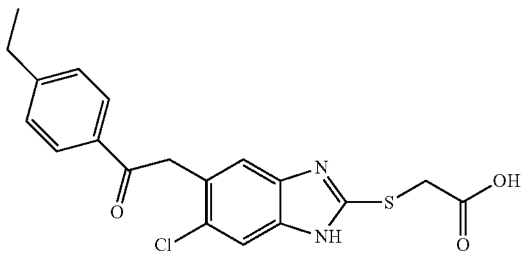 [SMILES: CCc1ccc(C(=O)Cc2cc3nc(SCC(=O)O)[nH]c3cc2Cl)cc1] | 389.4 |
| 75 | 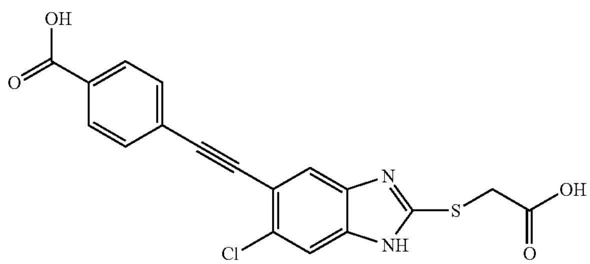 [SMILES: O=C(O)CSc1nc2cc(C#Cc3ccc(C(=O)O)cc3)c(Cl)cc2[nH]1] | 387.1 |
| 76 | 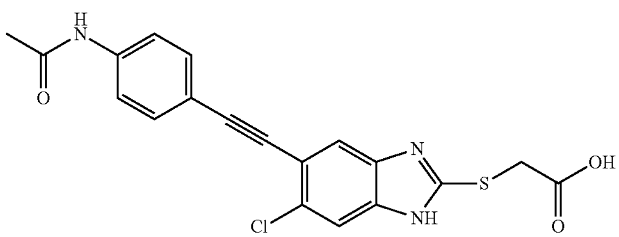 [SMILES: CC(=O)Nc1ccc(C#Cc2cc3nc(SCC(=O)O)[nH]c3cc2Cl)cc1] | 400.1 |
| 77 | 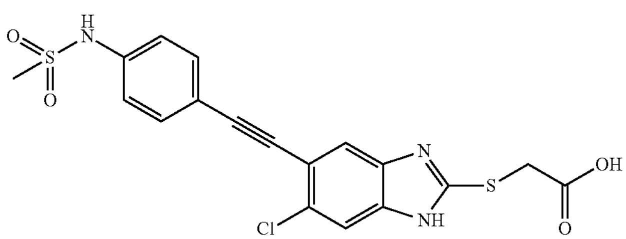 [SMILES: CS(=O)(=O)Nc1ccc(C#Cc2cc3nc(SCC(=O)O)[nH]c3cc2Cl)cc1] | 436.4 |
| 78 | 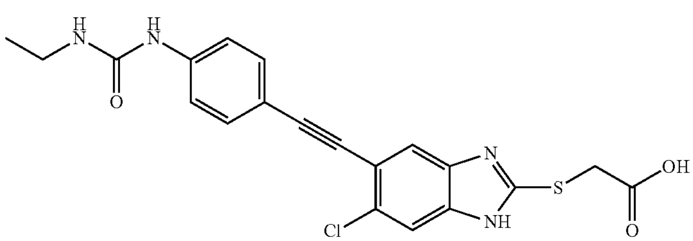 [SMILES: CCNC(=O)Nc1ccc(C#Cc2cc3nc(SCC(=O)O)[nH]c3cc2Cl)cc1] | 429.1 |
| 79 | 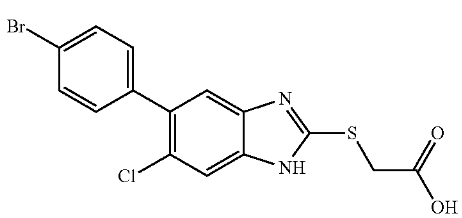 [SMILES: O=C(O)CSc1nc2cc(-c3ccc(Br)cc3)c(Cl)cc2[nH]1] | 398.9 |

TABLE 6-continued

Examples 54-86 in Table 6 were prepared following the procedures described in
Examples 52 and 53 and using the appropriate starting materials.

| Example No. | Structure | LCMS (M + H)+ |
| --- | --- | --- |
| 80 | 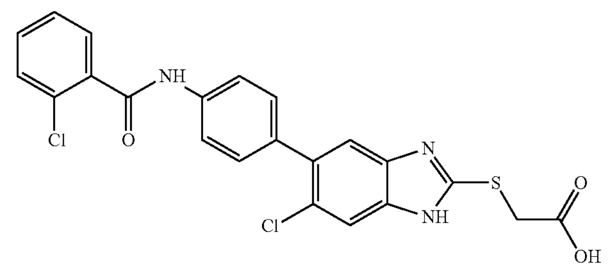 [SMILES: O=C(O)CSc1nc2cc(-c3ccc(NC(=O)c4ccccc4Cl)cc3)c(Cl)cc2[nH]1] | 374.4 |
| 81 | 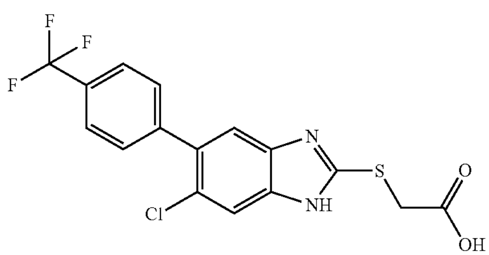 [SMILES: O=C(O)CSc1nc2cc(-c3ccc(C(F)(F)F)cc3)c(Cl)cc2[nH]1] | 387.1 |
| 82 | 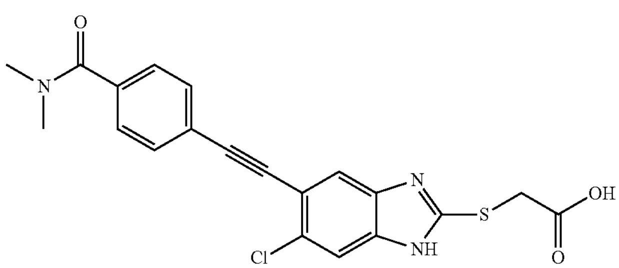 [SMILES: CN(C)C(=O)c1ccc(C#Cc2cc3nc(SCC(=O)O)[nH]c3cc2Cl)cc1] | 414.1 |
| 83 | 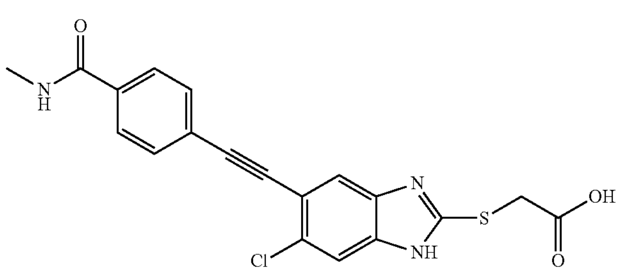 [SMILES: CNC(=O)c1ccc(C#Cc2cc3nc(SCC(=O)O)[nH]c3cc2Cl)cc1] | 400.1 |
| 84 | 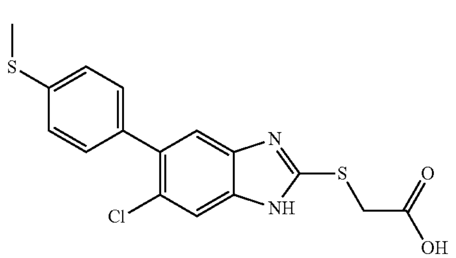 [SMILES: CSc1ccc(-c2cc3nc(SCC(=O)O)[nH]c3cc2Cl)cc1] | 365.4 |

TABLE 6-continued

Examples 54-86 in Table 6 were prepared following the procedures described in
Examples 52 and 53 and using the appropriate starting materials.

| Example No. | Structure | LCMS (M + H)+ |
|---|---|---|
| 85 | 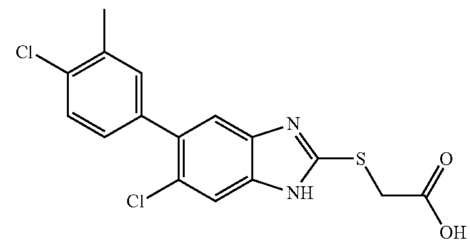 [SMILES: Cc1cc(-c2cc3nc(SCC(=O)O)[nH]c3cc2Cl)ccc1Cl] | 367.4 |
| 86 | 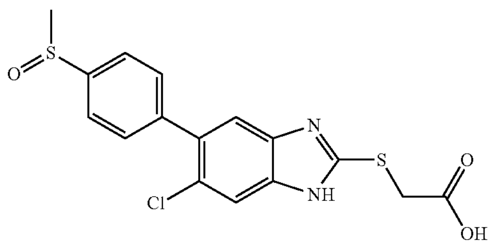 [SMILES: CS(=O)c1ccc(-c2cc3nc(SCC(=O)O)[nH]c3cc2Cl)cc1] | 381.4 |

Biological Example 1

AMPKSAMSF

In Vitro AMPK Activation Assay

The recombinant human AMPK complex 1 (containing α1β1γ1) was obtained from baculovirus expression system. Recombinant viruses were generated by cotransfection of AMPK/pBacPak9 clones with Baculogold baculovirus DNA (Pharmingen) in *spodoptera frugiperda* 21 cells according to the manufacturer's instructions. Each round of virus amplification was performed for 5 days in Grace's medium containing 10% serum. Virus that had been subjected to three rounds of amplification was used for all protein production procedures. To express the AMPK complex, sf21 cells were adapted to serum free medium (SF900 II, Invitrogen) by sequential dilution from serum containing stocks into SF900II medium and maintained in shaker flasks at 90 rpm at 27° C. The recombinant AMPK enzyme complex was produced by triple infection, one recombinant virus for each of the subunits, in sf21 cells under serum free conditions. Cells were infected in log phase, $1\times10^6$ cells/ml, at a multiplicity of infection of ~5. Cells were harvested by centrifugation at 10,000×g for 15 minutes after 72 hours of infection with viruses. The insect cell pellet from 2 liters of culture was resuspended in 50 ml lysis buffer (20 mM Tris-HCl, 50 mM NaCl, 50 mM NaF, 30 mM Na PPi, 0.25 M sucrose, 10 mM $ZnCl_2$, 2 mM DTT, 0.4 mg/ml digitonin) and subjected to two cycles of freeze-thaw lysis in a dry-ice ethanol bath. Insoluble material was removed by centrifugation at 10,000×g and the supernatant was fractionated with use of polyethylene glycol (PEG). The protein fraction precipitating between 2.5 and 6% PEG was used for further purification using a Blue-Sepharose step (Zhou et al, *J. Clin. Invest.* 108, 1167-1174, 2001).

The total in vitro AMPK activation assay volume is 50 μl in a 96-well plate. The reaction mixture contained 100 μM ATP (0.5 μCi $^{33}$P-ATP per reaction), and 50 μM SAMS (HMR-SAMSGLHLVKRR) in a buffer (20 mM HEPES, pH 7.0, 5 mM $MgCl_2$, 0.01% Brij35). The reaction was initiated with addition of the enzyme. After 30-minute incubation at 30° C., the reaction was stopped by addition of 80 μl 1% $H_3PO_4$. Aliquots (100 μl) were transferred to 96-well MultiScreen plates (MAPHNOB50; Millipore Corp., Bedford, Mass., USA). The plate was washed three times with 1% $H_3PO_4$ followed by detection in a Top-count. The counts per minute from the basal activity (the reaction without activator) was subtracted from each well and the data were expressed as % maximum AMP activation followed by $EC_{50}$ calculation. The % maximum AMP activation for selected compounds is provided in the table below.

The compounds of the present invention have greater than 40% maximum AMP activation of human AMPK complex 1 (containing α1β1γ1), and $EC_{50}$ values of less than 10 micromolar.

The compounds of Examples 1-86 were tested in the in vitro AMPK activation assay using recombinant human AMPK complex 1 (containing α1β1γ1) and found to have $EC_{50}$ values of less than 10 micromolar and greater than 40% maximum AMP activation. Preferred compounds of the present invention were found to have $EC_{50}$ values of less than 0.5 micromolar in the in vitro AMPK activation assay using recombinant human AMPK complex 1.

| Maximum AMP Activation for Selected Compounds | | |
|---|---|---|
| Example No. | % Maximum AMP Activation of human AMPK Complex 1 | $EC_{50}$ (nM) |
| 1 | 269 | 259 |
| 2 | 197 | 90 |
| 6 | 150 | 13 |
| 18 | 259 | 248 |
| 45 | 239 | 160 |
| 46 | 177 | 128 |
| 47 | 157 | 97 |

-continued

Maximum AMP Activation for Selected Compounds

| Example No. | % Maximum AMP Activation of human AMPK Complex 1 | $EC_{50}$ (nM) |
|---|---|---|
| 48 | 147 | 130 |
| 59 | 205 | 100 |
| 66 | 279 | 282 |

Biological Example 2

Inhibition of Fatty Acid Synthesis (FAS) by AMPK Activators in db/+Mice

To determine the effect of AMPK activators on Fatty Acid Synthesis (FAS) in the liver, the effect of oral pre-dosing of compounds on the amount of $^3H$ incorporated into hepatic triglyceride is determined as described by Sakurai T, Miyazawa S, Shindo Y, and T. Hashimoto (Biochim Biophys Acta. 1974 Sep. 19; 360 (3):275-88). Briefly, mice (db/+, Jackson Laboratory, Maine) are orally dosed with AMPK activators at time=−8 h. Then at time=−1 h, mice are injected with 0.5 ml of 0.15 M NaCl containing 0.2 mCi of $^3H$ water per 100 g of body weight. At time 0, mice are sacrificed via cervical dislocation and livers are harvested for FAS analysis. To analyze livers for FAS, samples of liver are heated at 90° C. for 5 hours in a 4 M KOH/50% ethanol solution. Then the alkaline hydrolysate of liver is extracted with hexane and acidified to a pH <2 with 10 M $H_2SO_4$. The fatty acids of liver are then extracted from acidified hydrolysate with additional hexane, dried down with a stream of warm air, then re-suspended in scintillation fluid, and counted on a beta counter. The amount of fatty acids synthesized per gram of liver is calculated based on the amount of $^3H$ incorporated into hepatic triglyceride. The amount of $^3H$ radiolabelled fatty acids synthesized in mice with treated with an AMPK activator is significantly less than the amount of $^3H$ radiolabelled fatty acids synthesized in the control mice.

Biological Example 3

In Vivo Study for Therapy with an AMPK Activator in Mice (Glucose Tolerance Test)

DIO mice are treated simultaneously with an effective dose of an AMPK-activated protein kinase activator.

Materials and Methods: Male C57BL/6NT mice (Taconic, 16-18 weeks old at the beginning of the drug administration) are used. Mice are given water and high fat diet D12492 (Research Diet Inc.) ad libitum. They are kept in an animal room which is maintained at 23±2 C temperature, 55±15% relative humidity and on a 12-hr light-dark cycle (7:00-19:00) during a quarantine and acclimatization period of 1 week. Animals are then administered vehicle (5 ml/kg of 0.5% methylcellulose in distilled water) by oral gavage twice-daily at 9 AM and 5 PM. After 9 days, stable body weight is observed. The following day (day −1), the mice are fasted for 4 hours and tail bled to determine the glucose and insulin levels. Animals are sorted into groups based on plasma glucose, insulin levels and body weight (n=8). The body weight and food in the hopper are recorded on day 0 before compound dosing is initiated. One of the groups is orally administered vehicle while the second group is administered an AMPK-activated protein kinase activator of the present invention at a dose of 30 mg/kg (5 ml/kg) twice-daily for 12 days by gavage. Body weight and food intake are measured every other day. On day 5, the animals are fasted 4 hours for measuring plasma glucose and insulin levels after morning dosing. At day 12, body weight and food intake are measured and animals receive their last morning dose. Mice again are fasted 4 hours, blood is collected at a set time point (t=0 min), and then challenged with dextrose orally (2 g/kg) Plasma glucose and insulin levels are determined from tail bleeds taken at 20 and 90 minutes after dextrose challenge. The plasma glucose and insulin excursion profile from t=0 to t=90 min is used to integrate an area under the curve (AUC) for each treatment. Percent inhibition values for each treatment are generated from the AUC data normalized to the C57BL/6NT mice feed with D7012. Preferred compounds of the present invention significantly reduce day 12 glucose and/or insulin AUC during the Oral Glucose Tolerance Test after an oral dose in the range of 0.1 to 100 mg/kg.

Biological Example 4

Acute Food Intake Studies in Diet Induced Obese (DIO) Mice: General Procedure

Adult DIO mice are used in these studies. After at least 2 days of acclimation to the vivarium conditions (controlled humidity and temperature, lights on for 12 hours out of 24 hours) food (D12492 (Research Diet Inc.) is removed from rodent cages. An AMPK activator of the present invention or the vehicle is administered orally, intraperitoneally, subcutaneously or intravenously before the return of a known amount of food to cage. The optimal interval between dosing and food presentation is based on the half-life of the compound based on when brain concentrations of the compound is the highest. Food remaining is measured at several intervals. Food intake is calculated as grams of food eaten per gram of body weight within each time interval and the appetite-suppressant effect of the AMPK activator is compared to the effect of the vehicle. The food intake of mice treated with an AMPK activator is significantly less than the food intake of control mice.

Biological Example 5

Chronic Weight Reduction Studies in Diet Induced Obese (DIO) Mice: General Procedure Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of structural formula I:

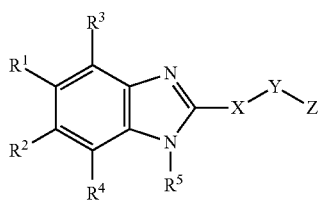

(I)

or a pharmaceutically acceptable salt thereof, wherein:
X is absent or selected from:
  (1) —S—,
  (2) —O—,
  (3) —NH—,
  (4) —C(O)—,
  (5) —NHC(O)—,
  (6) —C(O)NH—,
  (7) —NHSO$_2$—,
  (8) —SO$_2$NH—, and
  (9) —CO$_2$—,
wherein NH is unsubstituted or substituted with 1 substituent selected from: —C$_{1-6}$alkyl, —CO$_2$H, —CO$_2$C$_{1-6}$alkyl, —COC$_{1-6}$alkyl, phenyl and —CH$_2$-phenyl;
Y is selected from:
  (1) —CH$_2$—,
  (2) —CH$_2$—CH$_2$—,
  (3) —CH$_2$—CH$_2$—CH$_2$—,
  (4) —CHF—, and
  (5) —CF$_2$—,
wherein each CH$_2$ and CHF is unsubstituted or substituted with 1 or 2 substituents selected from Rb;
Z is selected from:
  (1) —CO$_2$H,
  (2) —C(O)NH$_2$,
  (3) tetrazole, and
  (4) dihydrooxadiazole,
wherein each dihydrooxadiazole and tetrazole is unsubstituted or substituted with 1, 2, or 3 substituents selected from R$^c$;
R$^1$ is independently selected from:
  1) —C$_{3-10}$cycloalkyl,
  2) —C$_{3-7}$cycloalkyl-aryl,
  3) —C$_{3-7}$cycloalkyl-heteroaryl,
  4) —C$_{4-10}$cycloalkenyl,
  5) —C$_{4-7}$cycloalkenyl-aryl,
  6) —C$_{4-7}$cycloalkenyl-heteroaryl,
  7) aryl,
  8) biphenyl,
  9) -heteroaryl,
  10) —C$_{2-6}$alkenyl-alkyl,
  11) —C$_{2-6}$alkenyl-aryl,
  12) —C$_{2-6}$alkenyl-heteroaryl,
  13) —C$_{2-6}$alkenyl-C$_{3-7}$cycloalkyl,
  14) —C$_{2-6}$alkenyl-C$_{3-7}$cycloalkenyl,
  15) —C$_{2-6}$alkenyl-C$_{2-7}$cycloheteroalkyl,
  16) —C$_{2-6}$alkenyl-C$_{2-7}$cycloheteroalkenyl,
  17) —C$_{2-6}$alkynyl-(CH$_2$)$_{1-3}$—O-aryl,
  18) —C$_{2-6}$alkynyl-alkyl,
  19) —C$_{2-6}$alkynyl-aryl,
  20) —C$_{2-6}$alkynyl-heteroaryl,
  21) —C$_{2-6}$alkynyl-C$_{3-7}$cycloalkyl,
  22) —C$_{2-6}$alkynyl-C$_{3-7}$cycloalkenyl,
  23) —C$_{2-6}$alkynyl-C$_{2-7}$cycloheteroalkyl,
  24) —C$_{2-6}$alkynyl-C$_{2-7}$cycloheteroalkenyl, and
  25) —(CH$_2$)$_p$C(O)phenyl,
wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each alkyl, alkenyl and alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$, and R$^2$ is selected from the group consisting of: halogen, —CN, —CF$_3$, —C$_{2-6}$alkenyl and —C$_{2-6}$alkynyl, wherein each alkenyl and alkynyl is unsubstituted or substituted with 1, 2 or 3 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$; or R$^2$ represents —C$_{1-6}$alkyl substituted with 1, 2 or 3 substituents selected from: halogen, CF$_3$, —OH, —NH$_2$, —OC$_{1-6}$alkyl, —NHC$_{1-6}$alkyl, and —N(C$_{1-6}$alkyl)$_2$;
R$^3$ is hydrogen;
R$^4$ is hydrogen;
R$^5$ is selected from:
  (1) hydrogen,
  (2) —C$_{1-6}$alkyl,
  (3) —CH$_2$CO$_2$H, and
  (4) —CH$_2$CO$_2$C$_{1-6}$alkyl;
each R$^a$ is independently selected from the group consisting of:
  (1) halogen,
  (2) oxo,
  (3) —(CH$_2$)$_m$OH,
  (4) —(CH$_2$)$_m$N(R$^j$)$_2$,
  (5) —(CH$_2$)$_m$NO$_2$,
  (6) —(CH$_2$)$_m$CN,
  (7) —C$_{1-6}$alkyl,
  (8) —(CH$_2$)$_m$CF$_3$,
  (9) —(CH$_2$)$_m$OCF$_3$,
  (10) —OCH$_2$OC$_{1-6}$alkyl,
  (11) —O-aryl,
  (12) —OCH$_2$-aryl,
  (13) —(CH$_2$)$_m$C(=N—OH)N(R$^j$)$_2$,
  (14) —(CH$_2$)$_m$OC$_{1-6}$alkyl,
  (15) —(CH$_2$)$_m$—O-aryl,
  (16) —(CH$_2$)$_m$SC$_{1-6}$alkyl,

(17) —(CH$_2$)$_m$S(O)C$_{1-6}$alkyl,
(18) —(CH$_2$)$_m$S(O)$_2$C$_{1-6}$alkyl,
(19) —(CH$_2$)$_m$NHS(O)$_2$C$_{1-6}$alkyl,
(20) —(CH$_2$)$_m$C(O)R$^f$,
(21) —(CH$_2$)$_m$C(O)N(R$^j$)$_2$,
(22) —(CH$_2$)$_m$N(R$^j$)C(O)R$^f$,
(23) —(CH$_2$)$_m$N(R$^j$)C(O)N(R$^j$)$_2$,
(24) —(CH$_2$)$_m$CO$_2$H,
(25) —(CH$_2$)$_m$OC(O)H,
(26) —(CH$_2$)$_m$CO$_2$R$^f$,
(27) —(CH$_2$)$_m$OC(O)R$_f$,
(28) —(CH$_2$)$_m$C$_{3-7}$cycloalkyl,
(29) —(CH$_2$)$_m$C$_{3-7}$cycloalkenyl,
(30) —(CH$_2$)$_m$C$_{2-6}$cycloheteroalkyl,
(31) —(CH$_2$)$_m$C$_{2-6}$cycloheteroalkenyl,
(32) —(CH$_2$)$_m$aryl, and
(33) —(CH$_2$)$_m$heteroaryl,
wherein each CH$_2$ is unsubstituted or substituted with 1 or 2 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and each alkyl, cycloalkyl, cycloalkenyl, cycloheteroalkyl, cycloheteroalkenyl, aryl and heteroaryl is unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$-phenyl, heteroaryl and CH$_2$heteroaryl;
each R$^b$ is independently selected from:
  (1) hydrogen,
  (2) —C$_{1-6}$alkyl,
  (3) halogen,
  (4) —OH,
  (5) —NO$_2$,
  (6) —NH$_2$,
  (7) —NH(C$_{1-6}$alkyl),
  (8) —N(C$_{1-6}$alkyl)$_2$,
  (9) —OC$_{1-6}$alkyl,
  (10) —CF$_3$,
  (11) —CN,
  (12) —SO$_2$C$_{1-6}$alkyl, and
  (13) —(CH$_2$)$_q$CON(R$^e$)$_2$,
wherein each CH$_2$ is unsubstituted or substituted with 1 or 2 halogens, and wherein each alkyl is unsubstituted or substituted with 1, 2 or 3 halogens;
each R$^c$ is independently selected from:
  (1) halogen,
  (2) oxo,
  (3) —(CH$_2$)$_r$OH,
  (4) —(CH$_2$)$_r$N(R$^e$)$_2$,
  (5) —(CH$_2$)$_r$CN,
  (6) —C$_{1-6}$alkyl,
  (7) —CF$_3$,
  (8) —C$_{1-6}$alkyl-OH,
  (9) —OCH$_2$OC$_{1-6}$alkyl,
  (10) —(CH$_2$)$_r$OC$_{1-6}$alkyl,
  (11) —OCH$_2$aryl,
  (12) —(CH$_2$)$_r$SC$_{1-6}$alkyl,
  (13) —(CH$_2$)$_r$C(O)R$^f$,
  (14) —(CH$_2$)$_r$C(O)N(R$^e$)$_2$,
  (15) —(CH$_2$)$_r$CO$_2$H,
  (16) —(CH$_2$)$_r$CO$_2$R$^f$,
  (17) —(CH$_2$)$_r$C$_{3-7}$cycloalkyl,
  (18) —(CH$_2$)$_r$C$_{2-6}$cycloheteroalkyl,
  (19) —(CH$_2$)$_r$aryl, and
  (20) —(CH$_2$)$_r$heteroaryl,
wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and each alkyl, cycloalkyl, cycloheteroalkyl, aryl and heteroaryl is unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C3$_{-7}$cycloalkyl and heteroaryl;
each R$^e$, R$^g$ and R$^h$ is independently selected from:
  (1) hydrogen, and
  (2) C$_{1-6}$alkyl,
wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;
each R$^j$ is independently selected from:
  (1) hydrogen,
  (2) C$_{1-6}$alkyl,
  (3) C$_{3-6}$cycloalkyl,
  (4) —C(O)R$^i$, and
  (5) —SO$_2$R$^i$,
wherein alkyl and cycloalkyl are unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;
each R$^f$ and R$^i$ is independently selected from:
  (1) C$_{1-6}$alkyl,
  (2) C$_{4-7}$cycloalkyl,
  (3) C$_{4-7}$cycloalkenyl,
  (4) C$_{3-7}$cycloheteroalkyl,
  (5) C$_{3-7}$cycloheteroalkenyl,
  (6) aryl, and
  (7) heteroaryl,
wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl;
n is 0, 1, 2, 3 or 4;
m is 0, 1, 2, 3 or 4;
p is 1;
q is 0, 1, 2, 3 or 4; and
r is 0, 1 or 2.

2. The compound according to claim 1, wherein X is absent or selected from: —S— and —O—, or a pharmaceutically acceptable salt thereof.

3. The compound according to claim 2, wherein X is selected from: —S— and —O—, or a pharmaceutically acceptable salt thereof.

4. The compound according to claim 3, wherein Y is selected from: —CH$_2$— and —CH$_2$—CH$_2$—, wherein each —CH$_2$ is unsubstituted or substituted with 1 or 2 substituents selected from Rb; or a pharmaceutically acceptable salt thereof.

5. The compound according to claim 4, wherein Y is —CH$_2$—, wherein CH$_2$ is unsubstituted or substituted with 1 or 2 substituents selected from R$^b$; or a pharmaceutically acceptable salt thereof.

6. The compound according to claim 5, wherein Z is —CO$_2$H; or a pharmaceutically acceptable salt thereof.

7. The compound according to claim 1, wherein $R^5$ is hydrogen; or a pharmaceutically acceptable salt thereof.

8. The compound according to claim 7, wherein $R^1$ is selected from:
  1) aryl,
  2) biphenyl,
  3) heteroaryl,
  4) —$C_{2-6}$alkynyl-$(CH_2)_{1-3}$—O-aryl,
  5) —$C_{2-6}$alkynyl-aryl,
  6) —$C_{2-6}$alkynyl-heteroaryl,
  7) —$C_{2-6}$alkynyl-$C_{3-7}$cycloalkyl,
  8) —$C_{2-6}$alkynyl-$C_{2-7}$cycloheteroalkyl, and
  9) —$(CH_2)_pC(O)$phenyl,
wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each alkynyl is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each cycloalkyl, cycloheteroalkyl, phenyl, aryl and heteroaryl is unsubstituted or substituted with 1, 2 or 3 substituents independently selected from $R^a$, and
$R^2$ is halogen; and
p is 1;
or a pharmaceutically acceptable salt thereof.

9. The compound according to claim 8, wherein each $R^a$ is independently selected from the group consisting of:
  (1) halogen,
  (2) —$(CH_2)_m$OH,
  (3) —$N(R^j)_2$,
  (4) —$NO_2$,
  (5) —CN,
  (6) —$C_{1-6}$alkyl,
  (7) —$CF_3$,
  (8) —O-aryl,
  (9) —$OCH_2$-aryl,
  (10) —$OC_{1-6}$alkyl,
  (11) —$SC_{1-6}$alkyl,
  (12) —$S(O)C_{1-6}$alkyl,
  (13) —$S(O)_2C_{1-6}$alkyl,
  (14) —$NHS(O)_2C_{1-6}$alkyl,
  (15) —$C(O)N(R^j)_2$,
  (16) —$(CH_2)_mN(R^j)C(O)R^f$,
  (17) —$N(R^j)C(O)N(R^j)_2$,
  (18) —$CO_2H$,
  (19) —$C_{2-6}$cycloheteroalkyl,
  (20) aryl, and
  (21) heteroaryl,
wherein each $CH_2$ is unsubstituted or substituted with 1 or 2 substituents selected from: oxo, —$(CH_2)_{0-3}$OH, —CN, —$NH_2$, —$NH(C_{1-6}$alkyl), —$N(C_{1-6}$alkyl$)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, and wherein alkyl, cycloheteroalkyl, aryl and heteroaryl are unsubstituted or substituted with 1, 2 or 3 substituents selected from: oxo, —$(CH_2)_{0-3}$OH, —CN, —$NH_2$, —$NH(C_{1-6}$alkyl), —$N(C_{1-6}$alkyl$)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl; or a pharmaceutically acceptable salt thereof.

10. The compound according to claim 1 of structural formula Ib:

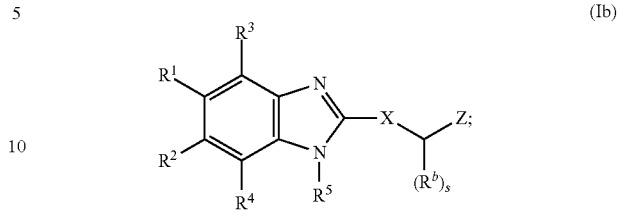

wherein:
$R^1$ is selected from:
  (1) phenyl,
  (2) biphenyl,
  (3) heteroaryl, and
  (4) —$C_2$alkynyl-phenyl,
wherein each phenyl and heteroaryl is unsubstituted or substituted with 1, 2 or 3 substituents independently selected from $R^a$;
$R^2$ is halogen;
$R^3$, $R^4$ and $R^5$ are hydrogen;
X is selected from: —S— and —O—;
Z is —$CO_2H$;
each $R^a$ is independently selected from the group consisting of:
  (1) —$(CH_2)_m$OH,
  (2) —$C_{1-6}$alkyl,
  (3) phenyl, and
  (4) heteroaryl,
wherein each alkyl, phenyl and heteroaryl is unsubstituted or substituted with 1, 2 or 3 substituents selected from: oxo, —$(CH_2)_{0-3}$OH, —CN, —$NH_2$, —$NH(C_{1-6}$alkyl), —$N(C_{1-6}$alkyl$)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl;
each $R^b$ is independently selected from: hydrogen, and —$C_{1-6}$alkyl, wherein each alkyl is unsubstituted or substituted with 1, 2 or 3 halogens; and
s is 0, 1 or 2;
or a pharmaceutically acceptable salt thereof.

11. The compound according to claim 10 selected from:

137
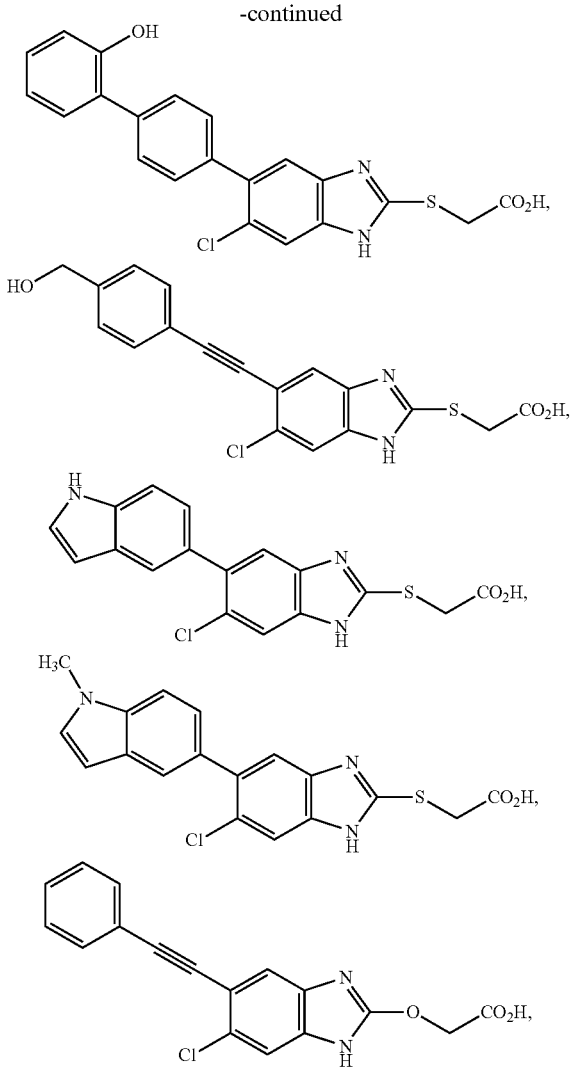
138
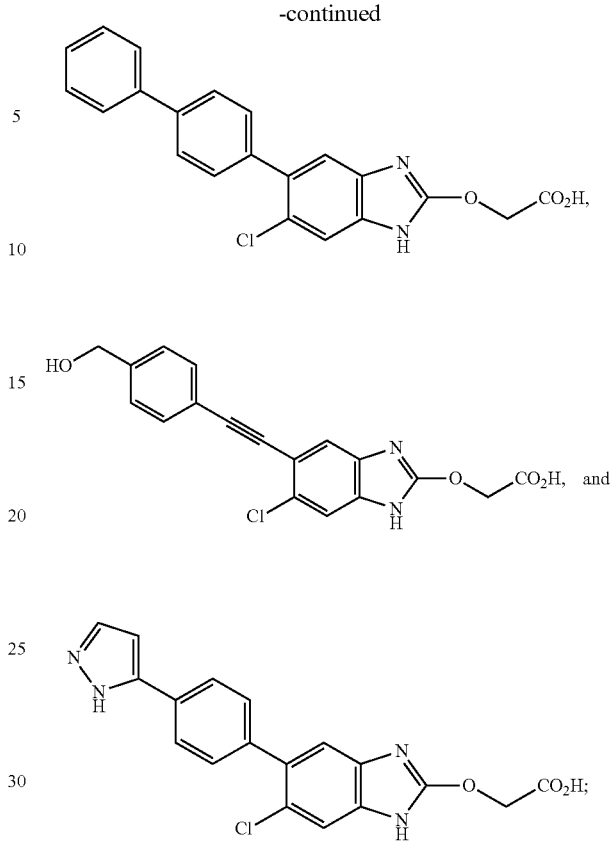
or a pharmaceutically acceptable salt thereof.
12. A composition comprising a compound according to claim 1 and a pharmaceutically acceptable carrier.
13. A composition comprising a compound according to claim 1, a compound selected from simvastatin, ezetimibe, taranabant and sitagliptin; and a pharmaceutically acceptable carrier.
* * * * *